United States Patent
Jiang et al.

(10) Patent No.: US 12,410,211 B2
(45) Date of Patent: Sep. 9, 2025

(54) V1A RECEPTOR PARTIAL AGONIST AND METHOD OF USE

(71) Applicant: PharmaIN Corporation, Bothell, WA (US)

(72) Inventors: Han Jiang, Burlingame, CA (US); Yao Yao, Seattle, WA (US); Gerardo M. Castillo, Bothell, WA (US); Akiko Nishimoto-Ashfield, Seattle, WA (US); Christian Ventocilla, San Francisco, CA (US); Elijah Bolotin, Bothell, WA (US)

(73) Assignee: PHARMAIN CORPORATION, Bothell, WA (US)

( * ) Notice: Subject to any disclaimer, the term of this patent is extended or adjusted under 35 U.S.C. 154(b) by 0 days.

(21) Appl. No.: 18/013,389

(22) PCT Filed: Jul. 16, 2021

(86) PCT No.: PCT/US2021/041998
§ 371 (c)(1),
(2) Date: Dec. 28, 2022

(87) PCT Pub. No.: WO2022/016064
PCT Pub. Date: Jan. 20, 2022

(65) Prior Publication Data
US 2023/0248800 A1 Aug. 10, 2023

Related U.S. Application Data

(60) Provisional application No. 63/053,340, filed on Jul. 17, 2020.

(51) Int. Cl.
| | | |
|---|---|---|
| *C07K 7/16* | (2006.01) | |
| *A61K 31/55* | (2006.01) | |
| *A61P 7/10* | (2006.01) | |
| *A61P 9/12* | (2006.01) | |

(52) U.S. Cl.
CPC ............... *C07K 7/16* (2013.01); *A61K 31/55* (2013.01); *A61P 7/10* (2018.01); *A61P 9/12* (2018.01)

(58) Field of Classification Search
None
See application file for complete search history.

(56) References Cited

U.S. PATENT DOCUMENTS

| | | |
|---|---|---|
| 9,657,078 B2 | 5/2017 | Castillo |
| 2004/0031072 A1 | 2/2004 | La Rosa et al. |
| 2014/0220057 A1 | 8/2014 | Okubo et al. |
| 2015/0126432 A1 | 5/2015 | Wisniewski et al. |
| 2016/0122386 A1 | 5/2016 | Wisniewski et al. |
| 2019/0083568 A1 | 3/2019 | Johnson et al. |

FOREIGN PATENT DOCUMENTS

| | | |
|---|---|---|
| CA | 1246055 A | 12/1988 |
| EP | 0037516 B1 | 9/1984 |
| JP | 2008-133229 A | 6/2008 |
| JP | 2015-518820 A | 7/2015 |
| WO | 2009/045309 A2 | 4/2009 |

OTHER PUBLICATIONS

Glavas et al. Vasopressin and Its Analogues: From Natural Hormones to Multitasking Peptides. Int. J. Mol. Sci. 2022, 23, 3068, 1-30 (Year: 2022).*
Boucheix et al. Selepressin, a New Via Receptor Agonist: Hemodynamic Comparison To Vasopressin in Dogs. Shock, vol. 39, No. 6, pp. 533Y538, 2013 (Year: 2013).*
Chan, W.Y. et al., "Discovery and design of novel and selective vasopressin and oxytocin agonists and antagonists: the role of bioassays," Experimental Physiology, vol. 85S; 7S-18S (2000).
Eriksen, P.L. et al., "Terlipressin for variceal bleeding induces large plasma sodium fluctuations in patients without cirrhosis," United European Gastroenterology Journal, vol. 6; No. 8; 1199-1205 (2018).
Gupta, J. et al., "Oxytocin-induced contractions within rat and rabbit ejaculatory tissues are mediated by vasopressin V1A receptors and not oxytocin receptors," British Journal of Pharmacology, vol. 155; 118-126 (2008).
Krag, A. et al., "Hyponatremia in Patients Treated With Terlipressin: Mechanisms and Implications for Clinical Practice," Hepatology, vol. 53; No. 1; 368-369 (2011).
Krag, A. et al., "Terlipressin Improves Renal Function in Patients with Cirrhosis and Ascites Without Hepatorenal Syndrome," Hepatology, vol. 46; 1863-1871 (2007).
Mitra, J. et al., "Vasopressin: Its current role in anesthetic practice," Indian Journal of Critical Care Medicine, vol. 15; Issue 2; 71-77 (2011).
Park, K.S. and Yoo, K.Y., "Role of vasopressin in current anesthetic practice," Korean J Anesthesiol, vol. 70; No. 3; 245-257 (2017).
Rihakova, L. et al., "VRQ397 (CRAVKY): a novel noncompetitive V2 receptor antagonist," Am J Physiol Regul Integr Comp Physiol, vol. 297; R1009-R1018 (2009).
Sima, M. et al., "Terlipressin Induced Severe Hyponatremia," Prague Medical Report, vol. 117; No. 1; 68-72 (2016).

(Continued)

*Primary Examiner* — Christina Bradley
(74) *Attorney, Agent, or Firm* — HAMILTON, BROOK, SMITH & REYNOLDS, P.C.

(57) ABSTRACT

The present disclosure provides novel V1a partial agonists for partially activating a V1a receptor. The partial V1a agonist has a therapeutic index of at least 20 (e.g., at least 30, at least 40, at least 50, at least 60, at least 70, at least 80, at least 90, at least 100). Also provided are method of treating liver fibrosis, cirrhosis, portal hypertension, ascites, esophageal varices, fundal varices, bleeding, arterial hypotension, and/or hepatorenal syndrome, including administering to a subject in need thereof a therapeutically effective dose of a composition including the V1a partial agonist(s) of the present disclosure, optionally in combination with a V2 antagonist.

25 Claims, 3 Drawing Sheets
Specification includes a Sequence Listing.

(56) References Cited

OTHER PUBLICATIONS

Sola, E. et al., "Hyponatremia in Patients Treated With Terlipressin for Severe Gastrointestinal Bleeding Due to Portal Hypertension," Hepatology, vol. 52; 1782-1790 (2010).
Yazawa, H. et al., "Oxytocin receptors expressed and coupled to Ca2 + signalling in a human vascular smooth muscle cell line," British Journal of Pharmacology, vol. 117; 799-804 (1996).
Von Dreele, P.H. et al., "Nuclear Magnetic Resonance Spectrum of Deamino-Lysine-Vasopressin in Aqueous Solution and Its Structural Implications," Proc. Natl. Acad. Sci., vol. 69; No. 11; 3322-3326 (1972).
Notification of Transmittal of the International Search Report and Written Opinion for International Application No. PCT/ US2021/ 041998, mailed Jan. 18, 2022.
Anonymous: "Ornipressin: a synthetic derivative of vasopressin", Aug. 19, 2018, XP093179124, Retrieved from the Internet: URL :https ://www.creative-peptides.com/article/ornipressin- a- synthetic - derivative- of -vasopressin-38.html.
Fernandez-Varo, G. et al., "Vasopressin la receptor partial agonism increases sodium excretion and reduces portal hypertension and ascites in cirrhotic rats", Hepatology, vol. 63, No. 1, Jan. 1, 2016, pp. 207-216.
Maurice Manning: "Impact of the Merrifield solid phase method on the design and synthesis of selective agonists and antagonists of oxytocin and vasopressin: A historical perspective", Biopolymers, vol. 90, No. 3, Jul. 3, 2007, pp. 203-212.
Rajekar, H. et al., "Terlipressin in hepatorenal syndrome: Evidence for present indications : Terlipressin in hepatorenal syndrome", Journal of Gastroenterology and Hepatology, vol. 26, Suppl. 1, Jan. 1, 2011, pp. 109-114.
Saito, M. et al., "1-Desamino-8-D-Arginine Vasopressin (DDAVP) as an Agonist on V1b Vasopressin Receptor," Biochemical Pharmacology, vol. 53; 1711-1717 (1997).
Supplementary European Search Report for EP Application No. 21842340.8, mailed Oct. 1, 2024; 17 pages.
Tsukamoto, I., "Recent patenting activities in the discovery and development of vasopressin V2 receptor agonists," Expert Opin. Ther. Patents, vol. 22; No. 6; 579-586 (2012).
Wis ' niewski, K. et al., "Discovery of Potent, Selective, and Short-Acting Peptidic V2 Receptor Agonists," Journal of Medicinal Chemistry, vol. 62; 4991-5005 (2019).
Wisniewski, K. et al., "New, potent, selective, and short-acting peptidic V1a receptor agonists," J. Med. Chem., vol. 54; 4388-4398 (2011).
Yea, C.M. et al., "New Benzylureas as a Novel Series of Potent, Nonpeptidic Vasopressin V2 Receptor Agonists," J. Med. Chem., vol. 51; 8124-8134 (2008).
Zhou, X. et al., "Terlipressin for the treatment of acute variceal bleeding", Medicine, vol. 97, No. 48, Nov. 1, 2018, pp. 1-11.
Kam et al., "Vasopressin and terlipressin: pharmacology and its clinical relevance", Anaesthesia, vol. 59, 2004, 9 pages.
Kimbrough et al., "Synthesis and Biological Properties of 1-Desamino-8-lysine-vasopressin", The Journal of Biological Chemistry, vol. 238, No. 4, Apr. 1963, pp. 1411-1414.
Pena et al., "Design and Synthesis of the First Selective Agonists for the Rat Vasopressin V1b Receptor: Based on Modifications of Deamino-[Cys 1]arginine Vasopressin at Positions 4 and 8†", J. Med. Chem., vol. 50, 2007, pp. 835-847.

\* cited by examiner

V1A RECEPTOR PARTIAL AGONIST AND METHOD OF USE

RELATED APPLICATIONS

This application is the U.S. National Stage of International Application No. PCT/US2021/041998, filed on Jul. 16, 2021, published in English, which claims the benefit of U.S. Patent Application No. 63/053,340, filed on Jul. 17, 2020. The entire teachings of the above applications are incorporated herein by reference.

STATEMENT OF GOVERNMENT LICENSE RIGHTS

This invention was made with Government support under DK103553 awarded by the National Institutes of Health. The Government has certain rights in the invention.

INCORPORATION BY REFERENCE OF MATERIAL IN ASCII TEXT FILE

This application incorporates by reference the Sequence Listing contained in the following ASCII text file:

a) File name: 61651022002_Sequence_Listing.txt; created Dec. 22, 2022, 20,064 Bytes in size.

BACKGROUND

Ascites is a serious complication of cirrhosis that occurs in about 50% of patients within 10 years after cirrhosis diagnosis and is associated with 50% mortality in 2 years. Ascites is a result of portal hypertension due to blockage of blood passage within the liver, resulting in an increase in nitric oxide, which leads to splanchnic arterial vasodilation that in turn increases incoming blood supply, which then results in more blood being trapped in the portal region to cause portal vein hypertension. The resulting nitric oxide-induced vasodilation is interpreted by the kidney as hypovolemia, and the kidney responds by retaining salt and water through the renin angiotensin aldosterone system (RAAS). The current standard treatment of ascites involves counteracting RAAS activity using diuretics to reduce fluid accumulation, and paracentesis to eliminate ascites fluid. However, this treatment does not improve the underlying pathophysiology and is only effective in the early disease stage when the peripheral blood volume and the overall salt contents in the body is still amenable to such a treatment. Moreover, this treatment becomes ineffective when the overall salt contents and blood volume are reduced to such low levels that the RAAS system is overactivated and shuts down the arterial blood supply to the kidney, leading to an increase in the potential for kidney failure and hepatorenal syndrome.

It is believed that vasoconstrictors in general and V1a agonists in particular appear to have a beneficial effect in decompensated cirrhosis without severe renal impairment and represent a potential treatment for cirrhosis complications including ascites. See Krag et al., Hepatology 2007; 46:1863-1871. Without wishing to be bound by theory, it is believed that vasoconstrictors reverse the arterial vasodilation, restores the arterial pressure, and reduces the splanchnic blood supply by vasoconstriction and thus reducing portal pressure; vasoconstrictors can further increase renal perfusion and filtration pressure and reverse the RAAS system response.

Vasopressin, also called antidiuretic hormone (ADH), is a hormone that is both a vasoconstrictor and an antidiuretic because of its action on both V1 and V2 receptors. Vasopressin is synthesized in the hypothalamus and travels down to the posterior pituitary to release into the circulatory system in response to extracellular fluid hypertonicity (hyperosmolality). In humans, vasopressin contains an arginine residue at amino acid position 8 and is called arginine vasopressin (AVP) or argipressin. In pigs, vasopressin contains a lysine residue instead of arginine at amino acid position 8 and is called lysine vasopressin (LVP). Terlipressin is a pig vasopressin with three additional glycine residues at the N-terminal and is referred to as tri-glycyl [8-lys] vasopressin. Terlipressin is believed to be an inactive prodrug of LVP that is rapidly converted to active LVP after administration, having similar action to AVP. Vasopressin is not protein-bound and has a volume of distribution of 140 ml/kg with a plasma half-life of 10 to 35 minutes, as it is rapidly metabolized by liver and kidney vasopressinases (35%) and finally excreted through the kidney (65%). LVP also has a short half-life of 50 minutes. See, Keun Suk Park and Kyung Yeon Yoo, Korean J Anesthesiol. 2017 June; 70(3): 245-257 and Jayanta K. Mitra et al., Indian J Crit Care Med. 2011 April-June; 15(2): 71-77. Vasopressin acts on V1 (also called V1a, present mainly in blood vessels), V2, V3 (also called V1b, present mainly in the central nervous system (CNS)), and oxytocin-type receptors (OTR). See, *Continuing Education in Anaesthesia Critical Care & Pain* 2008, 8(4): 134-137.

Vasopressin has two primary functions. First, vasopressin activates the V1 receptor (also called V1a) in smooth muscle, resulting in vasoconstriction and an attenuation of nitric oxide (NO) synthesis; resulting in increased peripheral vascular resistance that raises arterial blood pressure. Second, the activation of the V2 receptor by vasopressin in the kidney increases the reabsorption of solute-free water to reverse hypertonicity (i.e., more salt excretion relative to water). However, overactivation of V2 receptor can lead to low blood sodium concentration or hyponatremia. See Sima, M. et al., Prague Medical Report 2016, 117 (1):68-72; Sola E. et al., Hepatology 2010 52(5):1783-90; Krag et al., Hepatology 2011,53(1):367-369; Eriksen, P. L., et al., United European Gastroenterology Journal 2018, (8):1199-1205.

Because vasopressin can act on 3 different receptors (V1, V2, V3), a change in the balance of the activities on the three receptors can have dramatic physiological consequences. Minor structural modifications of vasopressin can result in a dramatic and unpredictable change in activity. For example, a change in the L-arginine residue of AVP to D-arginine and deamination of the N-terminus provides desmopressin, which has a 2-hour half-life and a more selective V2 agonist or antidiuretic effect compared to AVP and LVP. Desmopressin is therefore suited for use for the treatment of polyuria such as diabetes insipidus polyurea and nocturnal enuresis. Counterintuitively, even though modified vasopressins are called antidiuretic hormones, not all of them will have diuretic effect, which depends on the particular modifications to the peptide structure.

For example, terlipressin has limited V2 or anti-diuretic activity (only 3%, see www.medicines.org.uk/emc/product/2115/smpc/print) and its V1a pressor effect is useful in treating bleeding esophageal varices and hepatorenal syndrome. See, www.medsafe.govt.nz/profs/datasheet/g/GlypressinO1mgmlFerringinj.pdf. However, the use of terlipressin is currently limited to the acute care setting because of its short half-life. Furthermore, a large bolus dose to compensate for the short half-life of terlipressin causes severe hypertension and ischemia in many organs due to a very high $C_{max}$ (maximum blood concentration), which necessitates small and frequent intravenous (IV) bolus injections every 4 to 6 hours to avoid ischemic-inducing high blood concentrations of the terlipressin. Additionally, subcutaneous administration of terlipressin can result in high local concentration under the skin, resulting in injection site necrosis in addition to cutaneous necrosis in other parts of the body at high sustained dosing. Thus, although terlipressin has been available in Europe for the past twenty years, attempts to improve its pharmacokinetic properties and to increase its half-life (but with a $C_{max}$ that does not cause ischemia) have failed, often resulting in loss of receptor specificity and in some instances providing instead an antagonist or an inhibitor of target and non-target receptors. See, Rihakova, L. et al., VRQ397 (CRAVKY): a novel noncompetitive V2 receptor antagonist. Am J Physiol Regul Integr Comp Physiol, 2009. 297(4): p. R1009-18 (SEQ ID NO. 34); Gupta, J. et al., Oxytocin-induced contractions within rat and rabbit ejaculatory tissues are mediated by vasopressin V1a receptors and not oxytocin receptors. Br J Pharmacol, 2008. 155(1): p. 118-26; Chan, W. Y. et al., Discovery and design of novel and selective vasopressin and oxytocin agonists and antagonists: the role of bioassays. Exp Physiol, 2000. 85 Spec No: p. 7S-18S; Yea, C. M. et al., New benzylureas as a novel series of potent, nonpeptidic vasopressin V2 receptor agonists. J Med Chem, 2008. 51(24): p. 8124-34; Saito, M., A. Tahara, and T. Sugimoto, 1-desamino-8-D-arginine vasopressin (DDAVP) as an agonist on V1b vasopressin receptor. Biochem Pharmacol, 1997. 53(11): p. 1711-7 (SEQ ID NO. 35); Yazawa, H. et al., Oxytocin receptors expressed and coupled to Ca2+ signaling in a human vascular smooth muscle cell line. Br J Pharmacol, 1996. 117(5): p. 799-804; Tsukamoto, I., Recent patenting activities in the discovery and development of vasopressin V2 receptor agonists. Expert Opin Ther Pat, 2012. 22(6): p. 579-86; and Wisniewski, K., et al., Discovery of Potent, Selective, and Short-Acting Peptidic V2 Receptor Agonists. J Med Chem, 2019. 62(10): p. 4991-5005.

A V2 inhibitor (Tolvaptan) acting as an aquaretic (i.e., a diuretic without natriuresis) had been approved for the treatment of hypervolemic and euvolemic hyponatremia (i.e., serum sodium of 125 mEq/L or less marked hyponatremia), including patients with heart failure and Syndrome of Inappropriate Antidiuretic Hormone (SIADH). Because Tolvaptan is hepatotoxic, it is contraindicated for patient with cirrhosis, hepatorenal, and portal hypertension ascites. See, drug warning label for tolvaptan, available at www.accessdata.fda.gov/drugsatfda_docs/label/2018/204441lbl.pdf. Therefore, any innovation that will lower the dose of this medication to avoid hepatotoxicity while improving efficacy will contribute significantly to the long-sought desire to improve treatment of patients with cirrhosis, hepatorenal, and portal hypertension-induced ascites and varices.

There is a need for a V1a receptor agonist that avoids or minimizes the drawbacks or limitations of terlipressin. The V1a receptor agonist should target vascular hydrodynamic imbalance in general, such as blood pressure, blood volume, and electrolyte imbalance seen, for example, in cirrhosis, portal hypertension, bleeding, ascites, sepsis, and hepatorenal syndrome. The therapeutic agent can be 1) a V1a agonist that can be repeatedly administered subcutaneously without causing injection site necrosis, 2) a V1a agonist that limits its activity even at high dose (i.e., a partial agonist of V1a) such that it will not activate the receptor to its maximum potential, thereby limiting organ ischemia side effects (and thereby having very high therapeutic index), and/or 3) a V1a agonist that does not have significant V2 activity or antidiuretic activity in vivo. The present disclosure seeks to fulfill these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a composition, including a V1a partial agonist peptide of Formula (A)

(A)
[SEQ ID NOS. 1-2]
[Mpa-Tyr-Phe-Z-Asn-Cys-Pro-B(X)$_a$-Gly-NH$_2$]

or a pharmaceutically effective salt thereof,
wherein:
the Mpa and Cys residues are covalently connected with a disulfide bond,
Z is Hgn or Gln;
  wherein when Z is Hgn [SEQ ID NO. 1]:
    B is any one of L-Lys, D-Lys, L-Orn, D-Orn, L-Dab, D-Dab, L-Dap, or D-Dap, and
    X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is an integer from 0 to 10 (e.g., from 0 to 1, from 1 to 2, from 1 to 3, from 1 to 10, from 1 to 6, from 4 to 10, or from 6 to 10), or
    X is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is an integer from 1 to 3;
  wherein when Z is Gln [SEQ ID NO. 2]:
    B is any one of L-Lys, D-Lys, L-Orn, D-Orn, L-Dab, D-Dab, L-Dap, or D-Dap, and
    X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is an integer from 6 to 10, or
    X is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is an integer from 1 to 3; and
  wherein the composition has a therapeutic index of at least 20 (e.g., at least 30, at least 40, at least 50, at least 60, at least 70, at least 80, at least 90, or at least 100).

In another aspect, the present disclosure features a method of treating a subject, including administering to a subject in need thereof a therapeutically effective dose of a pharmaceutical composition of Formula (A), and optionally in combination with a V2 antagonist administered within 1 to 8 hours, preferably 1 to 3 hours, before or after administration of a therapeutically effective dose of a V2 antagonist, preferably before administration of a therapeutically effective dose of the V2 antagonist.

In another aspect, the present disclosure features a method of treating a subject, including administering to a subject in need thereof a therapeutically effective dose of a pharmaceutical composition including a peptide of Formula (B), administered within 1 to 8 hours, preferably 1 to 3 hours, before or after administration of a therapeutically effective dose of a V2 antagonist, preferably after administration of a therapeutically effective dose of the V2 antagonist, wherein the peptide of Formula (B) is a V1a agonist peptide of Formula (B)

(B)
[SEQ ID NOS. 3-4]
[X'-Tyr-Phe-Gln-Asn-Cys-Pro-Lys(Z)$_d$-Gly-NH$_2$]

or a pharmaceutically acceptable salt thereof,
wherein:
X is (U)$_c$-Cys or Mpa,
wherein when X is (U)$_c$-Cys [SEQ ID NO. 3],
the 2 Cys residues are covalently connected with a disulfide bond;
U is an amino acid residue and at each occurrence, is independently selected from Gly, L-Ala, D-Ala, L-Lys, D-Lys, L-Orn, D-Orn, L-Glu, D-Glu, L-Asp, and D-Asp, and
c is an integer of from 0 to 10;
Z is absent; and
d is a number of Z and is 0, and
wherein when X' is Mpa [SEQ ID NO. 4],
the Mpa and Cys residues are covalently connected with a disulfide bond,
Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and
d is an integer from 0 to 5.

In some embodiments, the subject has a condition selected from liver fibrosis, cirrhosis, portal hypertension, ascites, esophageal varices, fundal varices, bleeding, arterial hypotension, hepatorenal syndrome, and any combination thereof; or wherein the subject has liver fibrosis; or wherein the subject has cirrhosis; or wherein the subject has portal hypertension; or wherein the subject has esophageal varices; or wherein the subject has fundal varices; or wherein the subject has bleeding varices; or wherein the subject has arterial hypotension; or wherein the subject has hepatorenal syndrome.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
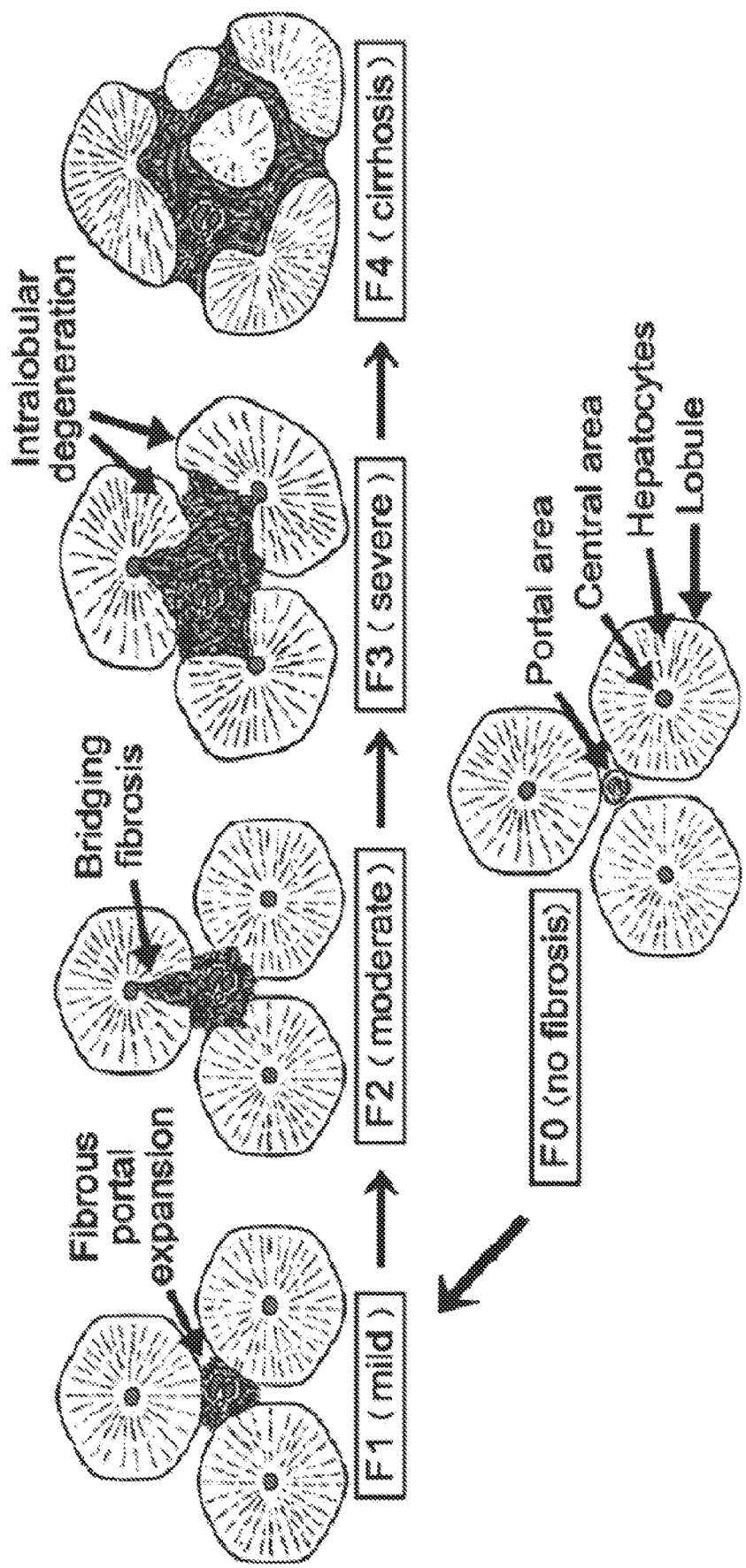
FIG. 1 is an illustration of the stages of liver fibrosis and cirrhosis.

The present disclosure describes compositions including a V1a partial agonist peptide of Formula (A)

(A)
[SEQ ID NOS. 1-2]
[Mpa-Tyr-Phe-Z-Asn-Cys-Pro-B(X)$_a$-Gly-NH$_2$]

or a pharmaceutically effective salt thereof,
wherein:
the Mpa and Cys residues are covalently connected with a disulfide bond,
Z is Hgn or Gln;
wherein when Z is Hgn [SEQ ID NO. 1]:
B is any one of L-Lys, D-Lys, L-Orn, D-Orn, L-Dab, D-Dab, L-Dap, or D-Dap, and
X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is a number of X and is an integer from 0 to 10 (e.g., from 0 to 1, from 1 to 2, from 1 to 3, from 1 to 10, from 1 to 6, from 4 to 10, or from 6 to 10), or
X at each occurrence is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is the number of X and is an integer from 1 to 3;
wherein when Z is Gln [SEQ ID NO. 2]:
B is any one of L-Lys, D-Lys, L-Orn, D-Orn, L-Dab, D-Dab, L-Dap, or D-Dap, and
X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is the number of X and is an integer from 6 to 10, or
X at each occurrence is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is the number of X and is an integer from 1 to 3; and
wherein the composition has a therapeutic index of at least 20 (e.g., at least 30, at least 40, at least 50, at least 60, at least 70, at least 80, at least 90, or at least 100).

A V2 antagonist can be administered within 1 to 8 hours, preferably 1 to 3 hours, before or after administration of the V1a partial agonist peptide(s) of the present disclosure, preferably before administration of the V1a partial agonist peptide(s).

In some embodiments, the present disclosure features a method of treating a subject, including administering to a subject in need thereof a therapeutically effective dose of a pharmaceutical composition of (i) or (ii), administered within 1 to 8 hours, preferably 1 to 3 hours, before or after administration of a therapeutically effective dose of a V2 antagonist, preferably after administration of a therapeutically effective dose of the V2 antagonist wherein (i) and (ii) are as defined below:

(i) a therapeutically effective dose of a pharmaceutical composition including a V1a agonist peptide of Formula (III)

(III)
[SEQ ID NO. 7]
[(U)$_c$-Cys-Tyr-Phe-Gln-Asn-Cys-Pro-Lys-Gly-NH$_2$]

or a pharmaceutically effective salt thereof,
wherein:
the 2 Cys residues are covalently connected with a disulfide bond,
U is an amino acid residue and at each occurrence, is independently selected from Gly, L-Ala, D-Ala, L-Lys, D-Lys, L-Orn, D-Orn, L-Glu, D-Glu, L-Asp, and D-Asp, and
c is a number of U and is an integer of from 0 to 10;
(ii) a therapeutically effective dose of a pharmaceutical composition including a V1a agonist peptide of Formula (IV)

(IV)
[SEQ ID NO. 4]
[Mpa-Tyr-Phe-Gln-Asn-Cys-Pro-Lys(Z)$_d$-Gly-NH$_2$]

or a pharmaceutically effective salt thereof,
wherein:
the Mpa and Cys residues are covalently connected with a disulfide bond,
Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and
d is a number of Z and is an integer from 0 to 5,
wherein the subject has a condition selected from liver fibrosis, cirrhosis, portal hypertension, ascites, esophageal varices, fundal varices, bleeding, arterial hypotension, hepatorenal syndrome, and any combination thereof; or
wherein the subject has liver fibrosis; or
wherein the subject has cirrhosis; or
wherein the subject has portal hypertension; or
wherein the subject has esophageal varices; or
wherein the subject has fundal varices; or
wherein the subject has bleeding varices; or
wherein the subject has arterial hypotension; or
wherein the subject has hepatorenal syndrome.

Definitions

At various places in the present specification, substituents of compounds of the disclosure are disclosed in groups or in ranges. It is specifically intended that the disclosure include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

As used herein, the term "polymer" refers to a macromolecule formed chiefly or entirely of many similar repeating units covalently bonded together. The term polymer includes cellulose derivatives, poly(ethylene glycol) (PEG), methoxy poly(ethylene glycol) (MPEG), poly(lactic-co-glycolic acid), and poly(N-vinyl pyrrolidone) and derivatives thereof. These polymers can be branched or linear. As used herein, a polymer can be attached to peptides, protein or a linker group by amide, ester, ether, thioether, thioester, or carbamate bond or by linkers containing one of those bonds. Polymer can also be grafted with each other for make a protected graft co-polymer excipient that, when mixed with an active pharmaceutical ingredient, can enhance pharmacokinetic and pharmacodynamics performance of active pharmaceutical ingredient by extending its presence in the blood or plasma after administration in vivo.

The term "amino acids" as used herein are organic compounds with molecular weight of less than 500 Da that contain amino (—NH$_2$) and carboxyl (—COOH) functional groups, along with a side chain (R group) specific to each amino acid. The key elements of an amino acid are carbon (C), hydrogen (H), oxygen (O), and nitrogen (N), although other elements are found in the side chains of certain amino acids. About 500 naturally occurring amino acids are known as of 1983 (though only 20 appear in the mammalian genetic code, these 20 amino acids are also referred to herein as "natural amino acids")). Amino acids can be alpha amino acids, where the amino group is bonded directly to the alpha carbon. Amino acids can be non-alpha amino acid, where the primary amino group is linked to a carbon other than the alpha position. The alpha carbon is the carbon directly adjacent to the carboxyl group. The amino acids can form building blocks of proteins and can have chiral carbons such that the amino acid can be of D or L optical isomers.

Three-letter codes for amino acids and/or peptide residues are used herein, except for non-alpha primary amino group-containing fatty acid moieties, which are described below. For example, alanine is Ala, arginine is Arg, asparagine is Asn, aspartic acid is Asp, cysteine is Cys, diaminobutyric acid is Dab, diaminopimelic acid is Dap, glutamic acid is Glu, glutamine is Gln, glycine is Gly, histidine is His, homoglutamine is Hgn, isoleucine is Ile, leucine is Leu, lysine is Lys, mercaptopropionic acid is Mpa, methionine is Met, Ornithine is Orn, phenylalanine is Phe, proline is Pro, serine is Ser, threonine is Thr, tryptophan is Trp, tyrosine is Tyr, valine is Val. As used herein, the codes for amino acids denote L-amino acids, unless otherwise indicated by "D-" prior to the code (e.g., D-Arg, etc.).

When one letter codes for amino acids are used herein, alanine is A, arginine is R, asparagine is N, aspartic acid is D, cysteine is C, glutamic acid is E, glutamine is Q, homoglutamine is homoQ, glycine is G, histidine is H, isoleucine is I, leucine is L, lysine is K, methionine is M, phenylalanine is F, proline is P, serine is S, threonine is T, tryptophan is W, tyrosine is Y, valine is V. For the purpose of the present application, the one letter codes for amino acids includes L and/or D amino acid stereoisomers.

It is understood that when the amino acids combine to form a peptide, the amino acids are referred to as amino acid residues where the elements of water are removed. Furthermore, where the present disclosure refers to an amino acid in a peptide sequence, it is understood to be an amino acid residue.

As used herein, the term "residue" refers to a divalent moiety obtained upon the removal of hydrogen from the alpha amino group and the hydroxyl group from the carboxyl group of an alpha-amino acid.

The term "derivative" or "analog" as used herein includes compounds whose core structures are the same as, or closely resemble that of, a parent compound, but which have a chemical or physical modification, such as different or additional groups; the term includes co-polymers of parent compounds that can be linked to other atoms or molecules. The term also includes a peptide or protein with at least at least 80% (e.g., at least 85%, at least 90%, at least 95%, or at least 98%) sequence identity with the parent peptide or protein. The term also includes a peptide with additional groups attached to it, such as additional label or tag, compared to the parent peptide. The term also includes a polymer with additional group attached to it, such as alkoxy or methoxy group, compared to the parent polymer.

As used herein, an "addition derivative" or "expansion derivative" refers to a peptide derivative where the main backbone amino acid sequence for a peptide remains the same, but the addition of extra functional groups and/or amino acid residue to the main amino acid sequence using one or more reactive moieties in the main amino acid sequence provides the addition derivative or the expansion derivative. The addition derivative or expansion derivative is different from a truncation and/or substitution peptide derivative where one or more amino acid residues in the main backbone amino acid sequence of the peptide have been removed and/or replaced by different functional groups and/or amino acids, respectively.

As used herein, the term "fatty acid" is molecule having a carboxyl group covalently bound to an alkyl chain, the fatty acid having 3-16 or more carbon units. In some embodiments, the fatty acid includes $C_{3-12}$ carbon units (e.g., $C_{3-6}$, $C_{3-10}$, $C_{4-12}$, $C_{4-6}$, $C_{4-10}$, $C_{6-10}$, $C_{8-10}$, or $C_{10-12}$ carbon units), including the carbon from the carboxyl group. The fatty acid can be functionalized with a non-alpha primary amino group, the functionalized fatty acid can be obtained from fatty acids or carboxyl amines. The fatty acid can be saturated or unsaturated. Examples of fatty acids includes caprylic acid, capric acid, lauric acid, myristic acid, palmitic acid, stearic acid, arachidic acid, behemic acid, and/or lignoceric acid.

As used herein, "non-alpha primary amino group-containing fatty acid" is a is a fatty acid containing a primary amino group linked to a carbon atom that is not at the alpha position relative to the carboxyl group and the amino group is not acylated. For example, beta-amino propanoic (propionic) acid is a non-alpha primary amino group-containing fatty acid with 3 carbon units, 4-amino butanoic(butyric) acid is an non-alpha primary amino group-containing fatty acid with 4 carbon units, 5-amino pentanoic (valeric) acid is an non-alpha primary amino group-containing fatty acid with 5 carbon units, 6-amino hexanoic (caproic) acid is an non-alpha primary amino group-containing fatty acid with 6 carbon units, 7-amino heptanoic (enanthic) acid is an non-alpha primary amino group-containing fatty acid with 7 carbon units, 8-amino octanoic (caprylic) acid is an non-alpha primary amino group-containing fatty acid with 8 carbon units, 9-amino nonanoic (pelargonic) acid is an non-alpha primary amino group-containing fatty acid with 9 carbon units, 10-amino decanoic (capric) acid is an non-alpha primary amino group-containing fatty acid with 10 carbon units, 11-amino undecanoic (undecylic) acid is an non-alpha primary amino group-containing fatty acid with 11 carbon units, 12-amino dodecanoic (lauric) acid is an non-alpha primary amino group-containing fatty acid with 12 carbon units, 13-amino tridecanoic (tridecylic) acid is an non-alpha primary amino group-containing fatty acid with 13 carbon units, 14-amino tetradecanoic (myristic) acid is an non-alpha primary amino group-containing fatty acid with 14 carbon units, 15-amino pentadecanoic (pentadecylic) acid is an non-alpha primary amino group-containing fatty acid with 15 carbon units, 16-amino palmitic acid is an non-alpha primary amino group-containing fatty acid with 16 carbon units, etc. The non-alpha primary amino group-containing fatty acid can be covalently bound to a peptide sequence at its N-terminus via the carboxyl group, or at its C-terminus via the amino group. When covalently bound to the peptide sequence or to another molecule, the non-alpha primary amino group-containing fatty acid residue is referred to as "a moiety derived from a non-alpha primary amino group-containing fatty acid."

As used herein, the term "fatty acid ester" refers to a long aliphatic chain (saturated or unsaturated) having a —C(=O)O— moiety at an end of the chain.

As used herein, the term "fatty acid amide" refers to a long aliphatic chain (saturated or unsaturated) having a —C(=O)NR— moiety at an end of the chain.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "fibrosis" or "liver fibrosis" refers to scarring of the liver, and the term "cirrhosis" refers to extensive scarring or fibrosis of the liver such that a significant number of lobules are surrounded by fibrous collagen scar tissue due to bridging together of several portal and central areas. Referring to FIG. 1, hepatic fibrosis in chronic hepatitis is graded according to the five stages (0-4) of the METAVIR scoring system (1994). With this score, F0 represents no fibrosis; F1 (mild fibrosis), having fibrous expansion of portal areas without septa; F2 (moderate fibrosis), where fibrous septa extend to form occasional bridges between adjacent vascular structures, including portal to portal and/or portal to central bridges; F3 (severe fibrosis), having numerous bridges or septa without cirrhosis (thick collagen scar bridging portal area and central area); and F4 (cirrhosis), where the tissue has nodules surrounded completely by fibrosis (e.g., significant number of lobules having turned into nodules surrounded by fibrous collagen scar). See, lipid peroxidation in hepatic fibrosis by Ichiro Shimizu et al., Lipid Peroxidation in Hepatic Fibrosis, published Aug. 29th 2012; DOI: 10.5772/46180, www.intechopen.com/books/lipid-peroxidation/lipid-peroxidation-in-hepatic-fibrosis, incorporated herein by reference in its entirety. Without wishing to be bound by theory, it is believed that cirrhosis of the liver is caused by many factors, including chronic heavy alcohol consumption, chronic hepatitis B or hepatitis C, buildup of fat in the liver, buildup of iron, cystic fibrosis, buildup of copper, poorly formed bile ducts, autoimmune diseases of the liver, bile duct injuries, liver infections, and/or taking certain medications, such as methotrexate.

As used herein, the term "compensated cirrhosis" refers to a cirrhosis that does not have clinical symptoms, such as varices and/or ascites, and the liver is still properly functioning.

As used herein, the term "decompensated cirrhosis" refers to a cirrhosis that is in an advanced stage, when liver scarring becomes so severe that the liver cannot function properly. Clinically, this is characterized by one or more ascites, varices with and without bleeding, jaundice, fatigue, weight loss, easy bleeding and bruising, ascites, swollen legs, confusion, slurred speech, drowsiness, hepatic encephalopathy, nausea and loss of appetite, spider veins, redness on the palms of the hands, shrinking testicles and breast growth in men, and/or unexplained itchiness. Serum bilirubin, creatinine, and international normalized ratio for prothrombin time (INR) are used to model for end-stage liver disease (MELD) score that ranges from 6 to 40 and is the most commonly used diagnostic tool for advanced liver disease. A MELD score=3.78×ln[serum bilirubin (mg/dL)]+11.2×ln[INR]+9.57×ln[serum creatinine (mg/dL)]+6.43.

As used herein, the term "mean arterial pressure" or "MAP" refers to ⅓ the difference between systolic (SBP) and diastolic pressure (DBP) plus DBP (i.e., MAP=1/3 (SBP−DBP)+DBP).

As used herein, the term "hypotension" refers to low blood pressure, for example, when the pressure of the blood pushing against the wall of the artery walls is low, or when the systolic pressure is less than 90 mm Hg and/or diastolic pressure is less than 60 mm Hg. Hypotension can be caused by relaxation of smooth muscle surrounding the blood vessels that increases vessel diameter.

As used herein, the term "portal vein" refers to blood vessels that transport the blood coming from the esophagus, stomach, spleen, pancreas, small intestine, and/or colon to the liver.

As used herein, the term "portal hypertension" or "portal vein hypertension" refers to a high portal vein pressure, for example, when the pressure of the blood pushing against the wall of the portal vein increases due to resistance or blockade of blood flow passing through the liver (e.g., blockade can be due to liver cirrhosis). Portal vein hypertension or portal hypertension can occur concurrently with reduced mean arterial pressure or MAP. A portal vein hypertension can be characterized by a hepatic venous pressure gradient (HVPG) that is above 5 mm Hg (e.g., above 7 mm Hg, above 10 mm Hg, or above 15 mm Hg). Clinically significant portal hypertension (CSPH) is defined as an HVPG of 10 mm Hg and above.

As used herein, the term "hepatic vein pressure gradient" or HVPG represents a clinical measurement of the pressure gradient between the wedged hepatic venous pressure (WHVP) and the free hepatic venous pressures (FHVP) and is an estimate of the pressure gradient between the portal vein and the inferior vena cava. HVPG is determined by inserting an inflatable catheter (inserted through antecubital, femoral, or right jugular veins) in a hepatic vein and measuring the pressure prior to inflation which is the FHVP. The WHVP is measured by inflation of the balloon catheter at the right hepatic vein to occlude the flow, followed by measurement of the pressure of proximal static blood (which is reflective of pressure in the sinusoids). Subsequently, the HVPG is determined by subtracting the FHVP from the WHVP (i.e., HVPG=WHVP−FHVP). WHVP in fact slightly underestimates portal pressure due to sinusoidal equilibration in patients without cirrhosis, but the difference between the two is clinically insignificant. In patients with cirrhotic livers, inter-sinusoidal communication is disrupted such that sinusoidal pressure equilibrium cannot be maintained, and thus WHVP is a far more accurate measure of portal venous pressure catheter and has been the standard approach for estimating portal venous pressure. An HVPG of ≥5 mm Hg defines portal hypertension, and if the measurement exceeds 10 mm Hg it is called clinically significant portal hypertension. Above 12 mm Hg, variceal bleeding can occur at any time, leading to a life-threatening emergency.

As used herein, the term "ascites" refers to an abnormal buildup of fluid in the abdomen (e.g., 25 ml or greater), commonly caused by cirrhosis. The fluid is an ideal medium for bacterial growth that leads to spontaneous bacterial peritonitis.

As used herein, the term "refractory ascites" refers to ascites that does not recede or that recurs shortly after therapeutic paracentesis, despite sodium restriction and diuretic treatment. To date, there is no approved medical therapy specifically for refractory ascites. As used herein, the term "paracentesis" refers to the perforation of a cavity (peritoneal) of the body with a hollow needle to remove fluid (or gas).

As used herein, the term "varices" refers to enlarged or swollen or dilated blood vessels caused by portal hypertension that can be life-threatening when present in the esophagus or stomach fundus. Varices cause no symptoms unless they rupture and bleed, in which case they present a life-threatening event that requires immediate medical attention. As used herein "esophageal varices" refers to abnormally enlarged veins in the esophagus that develop when normal venous blood flow to the liver is blocked by a clot or cirrhosis. Such varices can be life-threatening if they break open and bleed. The esophagus is the tube that connects the throat to the stomach. When enlarged veins occur on the lining of the esophagus, they are called esophageal varices.

As use herein, the term "gastric varices" refers to dilated submucosal veins in the stomach, which can be a life-threatening cause of bleeding in the upper gastrointestinal tract. They are most commonly found in patients with portal hypertension, or elevated pressure in the portal vein system, which may be a complication of cirrhosis. As used herein, the term "fundal varices" refers to a gastric varices in the fundal region of the stomach.

As used herein, the term "hepatorenal syndrome" or "HRS" refers to a type of progressive kidney failure seen in people with severe liver damage, most often caused by cirrhosis, and is an extremely serious condition and almost always fatal. As the kidneys stop functioning, toxins begin to build up in the body. Eventually, this leads to liver failure. There are two forms of HRS: type 1 HRS (median survival of 2 weeks, with 100% fatality in 8-10 weeks without liver transplant) is associated with rapid kidney failure and an accumulation of creatinine; type 2 HRS (median survival of 6 months) is associated with more gradual kidney damage. Type 2 HRS generally progresses more slowly. Symptoms are generally subtler and is associated portal hypertension and ascites development or beginning of ascites development. Type 2 HRS is treated with diuretics and salt restriction but eventually these patients develop a diuretic-resistant ascites where the kidneys are unable to excrete sufficient sodium to clear the fluid even with the use of diuretic medications. Most individuals with type 2 HRS have diuretic-resistant ascites before they develop deterioration in kidney function.

As used herein, the term "V1a partial agonist" refers to a therapeutic agent (e.g., a peptide) that bind to V1a receptor but have only partial efficacy at the receptor relative to a full agonist. For the purpose of the present disclosure, arginine vasopressin is a full agonist and is also known in the art as such. A partial agonist displays both agonistic and antagonistic effects and in the presence of a full agonist, the partial agonist acts as an antagonist and competes with the full agonist for the same receptor and thereby reducing the ability of the full agonist to produce its maximum effect. A V1a partial agonist causes partial vasoconstriction by acting on the smooth muscle lining of peripheral arterial vessels, resulting in an increase in blood pressure. Partial vasoconstriction minimizes the risk of ischemia while allowing the blood pressure to be increased; partial vasoconstriction can also reduce the supply of blood to the splanchnic region, which in addition to cirrhosis contributes to portal hypertension. In vivo, a full agonist at a high dose has a higher risk of complete closure of vessels resulting in loss of tissue oxygenation or tissue ischemia. A partial agonist can be demonstrated by measuring maximum activity (such a calcium influx) of a test agonist at a saturating concentration in cell culture and comparing the maximum activity to that of arginine vasopressin under the same conditions. To ensure that saturating concentration is attained during measurement, multiple concentrations of the test agonist is used until saturation has been demonstrated (evident from an approximate s-shaped saturation curve). The saturating concentration of a full agonist can be done in parallel and/or in a similar manner. A full agonist can be the reference 100% signal at saturation and a partial agonist has less than 100% signal at saturation (e.g., 80%, 60%, 50%, 40%, 20%, or 10%). This determination also provides effective concentration at 50% saturation or EC50 which is the concentration needed for half maximal binding to the receptor. This procedure is well known in the art and described in several examples in the present application.

As used herein, the term "therapeutic index" (TI; also referred to as therapeutic ratio) is a quantitative measure of the relative safety of a drug. For the purpose of the present disclosure, the TI is the ratio where the numerator is the highest dose that does not cause lethargy or adverse effect (no observed adverse effect level or NOAEL), relative to a control; and the denominator is the highest dose that does not cause observable peripheral vasoconstriction (no observed effect level or NOEL), compared to untreated control (i.e., the TI is the NOAEL/NOEL ratio). For the purpose of the present application, lethargy is a lack of energy and/or sleepiness which is visually observed in rats as a lack of mobility, such as a lack of mobility even in the presence of human activity. For the purpose of present specification, peripheral vasoconstriction is visually observed by a paleness of the extremities (e.g., skin of hands, feet, ears, and lips). In rats, peripheral vasoconstriction is determined by a side-by-side comparison of ear paleness in treated subjects (e.g., Sprague Dawley rats, a white rat with easily visualizable changes in redness/paleness) vs. untreated control subjects. The V1a agonist (or partial agonist) with a high therapeutic index will have a better safety profile than that with a low therapeutic index by providing a wider margin of safety for dosing during the treatment of the disease. This NOAEL/NOEL ratio, being a quantitative measure of the relative safety, is a comparison of the amount of a therapeutic agent that causes the therapeutic effect (useful effect, vasoconstriction for the purpose of the present specification) to the amount that causes toxicity. A V1a agonist that causes severe vasoconstriction will affect not only the peripheral vessels, with several layer of smooth muscles, but also other vessels present in other organs (e.g., heart, lungs, kidney, brain) and this will result in observed lethargy and eventually ataxia. A partial agonist is less likely to reach such an extreme level of vasoconstriction and is believed to have a higher therapeutic index.

As used herein, the term "V2 antagonist" refers to therapeutic agents that bind to V2 receptor and inhibit its function. Because inhibition of V2 receptor results in an increased production of low salt urine, the V2 antagonist is also called an aquaretic. One example of a V2 antagonist is Tolvaptan which competitively and selectively binds to V2 receptor without activating the V2 receptor, and which decreases the likelihood of native V2 receptor agonist to bind and activate the receptor to cause water reabsorption from glomerular filtrate to the blood. Thus, a V2 antagonist causes reduction in water content of the blood and in turn the blood volume.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" or "therapeutically effective dose" used interchangeably, refers to the amount of a therapeutic agent (i.e., drug, or therapeutic agent composition) that elicits the biological or medicinal response that is being sought in a tissue, system, animal, individual or human by a researcher, veterinarian, medical doctor, or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition, or disorder; and (3) ameliorating the disease; for example, ameliorating a disease, condition or disorder in an individual who is experiencing or displaying the pathology or symptomatology of the disease, condition, or disorder (i.e., reversing the pathology and/or symptomatology) such as decreasing the severity of disease, prolonging survival time, or preventing death.

As used herein, the term "treatment" refers to a procedure performed after diagnosis of the condition.

As used herein, the term "mitigation" refers a procedure that is performed to prevent, or decrease the likelihood, of an anticipated injury or disease.

As used herein, the term "healthy subject" refers to individual (human and/or mammalian animals) who are participant in a research study with no significant health related issues.

As used herein, a "bolus", "bolus dose" or "bolus administration" refers to a single dose of a drug or other substance given or administered over a short period of time, for example, less than 10 minutes (e.g., less than 8 minutes, less than 5 minutes, less than 3 minutes, or less than 1 minute). Administration includes one of: injection in any part of the body (including but not limited to blood vessels, subcutaneous, intrathecal, or intradermal), enterally (e.g., orally, as a dosage form), inhalation (e.g., by intratracheal inhalation administration, where a subject is exposed to high aerosol concentrations so that the active pharmaceutical ingredient is deposited directly in the lower respiratory tract), or nasally (e.g., as an aerosol, liquid, or powder). For the purpose of the present disclosure, a bolus administration is distinguished from infusion administration that usually takes 30 minutes or longer to complete.

As used herein, an "administration" also called "route of administration" refers to the location in the body in which a pharmacological agent is given or applied to a subject. Examples: Enteral/gastrointestinal which is delivered through the gastrointestinal tract that includes the whole digestive system from mouth to the rectum including oral, rectal, sublingual, and buccal. Parenteral which is delivered through the by routes other than the gastrointestinal tract such as intravenous, subcutaneous, subdermal, intramuscular, intraperitoneal, intrapleural, intranasal, etc.

As used herein, the term "subcutaneous administration," "s.c.", "s.c. administration," "SC," or "SC administration" refers to a delivery of drug, usually in liquid form, directly into the fatty tissues just beneath the skin. The delivery is usually carried out by direct injection. These injections are shallower than those injected into muscle tissues. Providers often use subcutaneous injections for medications that are suitable for absorption into the bloodstream slowly and steadily, As used herein, the term "intravenous administration," "IV administration," or "IV injection" refers to a delivery of drug, typically in liquid form, directly into a vein of an animal or human. The delivery methods are usually by direct injection. The intravenous route of administration can be used both for injections, using a syringe at higher pressures; as well as for infusions, for example, using the pressure supplied by gravity.

As used herein, the term "intramuscular administration," "IM administration," or "IM injection" refers to an intramuscular delivery of drug, usually in liquid form, directly into the muscles of an animal or human. The delivery is usually by direct injection. This allows the medication to be absorbed into the bloodstream quickly. In some instances, a person may also self-administer an IM injection. In some embodiments, IM injections can be used instead of intravenous injections, for example, when certain therapeutic agents are irritating to veins, or when a suitable vein cannot be located.

As used herein, the term "nasal administration" refers to a delivery of a therapeutic agent (e.g., in form of gel, liquid, aerosol, gas, or powder) by topical application, dropping as a liquid, insufflation (or blown or sprayed), into the nose of an animal or a human. This form of administration can be used, depending on the formulation, for example, to deliver a therapeutic agent to the nasal cavity or the lungs (depending on the device used), and/or may not be absorbed systemically (purely local administration), and/or may be totally absorbed systemically (purely systemic), and/or more frequently partially absorbed (both local and systemic). Nasal sprays can include locally acting drugs such as decongestants for cold and allergy treatment, whose systemic effects are typically minimal. Examples of systemically active drugs available as nasal sprays include, for example, migraine drugs, nicotine replacement, and hormone treatments.

As used herein, the term "parenteral" or "non-gastrointestinal" administration refers to a route of administration that is not through enteral or gastrointestinal routes. Examples of parenteral administration include subcutaneous (under the skin), intravenous (into a vein), intra-arterial (into an artery), intramuscular (into a muscle), intraperitoneal (infusion or injection into the peritoneum), inhalation (e.g., by intratracheal inhalation administration, where a subject is exposed to high aerosol concentrations of the active pharmaceutical ingredient such that the active pharmaceutical ingredient is deposited directly in the lower respiratory tract), nasal administration (through the nose), sublingual and buccal medication, intrathecal (into the spinal canal), intracerebral (into the cerebrum), intracerebroventricular (into the cerebral ventricles), intradermal (into the skin itself), or any other administration routes not involving the gastrointestinal tract. As used herein, the term "enteral" means administration to any region of the alimentary tract and including mouth (oral), pharynx (throat), esophagus, stomach, small intestine, large intestine, rectum, and anus or through an artificial opening in any of these regions.

As used herein, the term "enteral" refers to administration to any region of the alimentary tract and including mouth (oral), pharynx (throat), esophagus, stomach, small intestine, large intestine, rectum, anus, and/or through an artificial opening in any of these regions.

As used herein, the term "oral administration" also abbreviated as "P.O." refers to a route of administration where a substance is taken through the mouth and includes drinking, swallowing, sublingual (dissolved/absorbed under the tongue), buccal (dissolved/absorbed inside the cheek), and sublabial (dissolved/absorbed under the lip) routes of administration.

As used herein, the term "therapeutic agent," "drug," or "active pharmaceutical ingredient" refers to a substance or a molecule capable of producing a curative effect in a disease state.

As used herein, the term "formulation" and "pharmaceutical formulation" are used interchangeably and refer to a final medicinal product with an active drug(s) together with various inactive chemical substances, excipients, and/or buffer. In some embodiments, the formulation can take a dosage form such as a tablet, a linctus, an ointment, or an injectable liquid for administration into a subject.

As used herein, the term "excipient" refers to a substance or ingredient that is mixed with an active drug(s) or active pharmaceutical ingredient to provide, for example, long-term stabilization; to bulk up formulations (thus often referred to as "bulking agents", "fillers", or "diluents"); and/or to confer a therapeutic enhancement to the active pharmaceutical ingredient in the final dosage form, such as to facilitate drug absorption and/or potency/dose, to reduce viscosity, to enhance solubility, and/or to prolong the action or presence of the active pharmaceutical ingredient in the blood. The selection of suitable excipients can depend upon the route of administration and the dosage form, the active pharmaceutical ingredient, and other factors. The excipient can include, for example, sugar, amino acid, buffer, antioxidant, chelating agent, solvent, or vehicle, and/or a complex polymer that binds and stabilizes an active pharmaceutical ingredient in vitro and/or in vivo. Examples of such and other additives are found in "Handbook of Pharmaceutical Excipients"; Ed. A. H. Kibbe, 3rd Ed., American Pharmaceutical Association, USA and Pharmaceutical Press UK, 2000, incorporated herein by reference in its entirety.

As used herein, a "liquid" is a substance which flows freely at room temperature, such that its shape changes but its volume retains constant, e.g., as would water or an oil.

As used herein, "room temperature" denotes a typical ambient indoor temperature of about 25° C.

Unless defined otherwise, any feature within any aspect or embodiment of the disclosure may be combined with any feature within any other aspect or embodiment of the invention, and such combination are encompassed in the present disclosure. This also applies, but not exclusively, to endpoints of ranges disclosed herein. For instance, if a given substance is disclosed as existing in a composition in a concentration range of X-Y % or A-B %, the present disclosure is to be understood as explicitly disclosing not only the ranges X-Y % and A-B %, but also the ranges X-B %, A-Y % and, in as far as numerically possible, Y-A % and B-X %. Each of these ranges, and range combinations, are contemplated, and are to be understood as being directly and unambiguously disclosed in the present application.

Unless stated otherwise, the designation of a range in the present application using a hyphen ("-") separating two bracketing values X and Y, or two bracketing ratios, is to be understood as meaning and disclosing the specified range in which both endpoint values X and Y are included. The same applies to a range expressed as "from X to Y". Accordingly, the expressions of ranges as "X-Y", "of X to Y", "from X to Y", "of X-Y" and "from X-Y" are to be understood equivalently as meaning and disclosing a range encompassing the end value X, all values (including decimals) between X and Y, as well as the end value Y.

As used herein the term "about" when referring to a particular value, e.g., an endpoint or endpoints of a range, encompasses and discloses, in addition to the specifically recited value itself, a certain variation around that specifically recited value. Such a variation may for example arise from normal measurement variability, e.g., in the weighing or apportioning of various substances by methods known to the skilled person. The term "about" shall be understood as encompassing and disclosing a range of variability above and below an indicated specific value, said percentage values being relative to the specific recited value itself, as follows: The term "about" may encompass and disclose variability of ±5.0%. The term "about" may encompass and disclose variability of ±4.5%. The term "about" may encompass and disclose variability of ±4.0%. The term "about" may encompass and disclose variability of ±3.5%. The term "about" may encompass and disclose variability of ±3.0%. The term "about" may encompass and disclose variability of ±2.5%. The term "about" may encompass and disclose variability of ±2.0%. The term "about" may encompass and disclose variability of ±1.5%. The term "about" may encompass and disclose variability of ±1.0%. The term "about" may encompass and disclose variability of ±0.5%. The term "about", in reference to the particular recited value, may encompass and disclose that exact particular value itself, irrespective of any explicit mention that this exact particular value is included; even in the absence of an explicit indication that the term "about" includes the particular exact recited value, this exact particular value is still included in the range of variation created by the term "about", and is therefore disclosed in the present application. Unless stated otherwise, where the term "about" is recited before the first endpoint of a numerical range, but not before the second endpoint of that range, this term, and the variability it implies in scope and disclosure, refers to both the first endpoint of the range and the second endpoint of the range. For instance, a recited range of "about X to Y" should be read as "about X to about Y". The same applies for a recited range of ratios. For instance, a recited range of weight ratios of "about X:Y-A:B" should be read as a weight ratio of "(about X):(about Y)-(about A):(about B)".

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the FIGURES should not be viewed as limiting. It should be understood that other embodiments may include more or less of each element shown in a given FIGURE. Further, some of the illustrated elements may be combined or omitted. Yet further, an example embodiment may include elements that are not illustrated in the FIGURES.

Compositions

The present disclosure features a composition, including:
a V1a partial agonist peptide of Formula (A)

(A)  [SEQ ID NOS. 1-2]
[Mpa-Tyr-Phe-Z-Asn-Cys-Pro-B(X)$_a$-Gly-NH$_2$]

or a pharmaceutically effective salt thereof, wherein:

the Mpa and Cys residues are covalently connected with a disulfide bond,

Z is Hgn or Gln;

wherein when Z is Hgn [SEQ ID NO. 1], the peptide of Formula (A) is a peptide of Formula (I):

(I)  [SEQ ID NO. 1]
[Mpa-Tyr-Phe-Hgn-Asn-Cys-Pro-B(X)$_a$-Gly-NH$_2$]

wherein:

B is any one of L-Lys, D-Lys, L-Orn, D-Orn, L-Dab, D-Dab, L-Dap, or D-Dap, and

X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is an integer from 0 to 10 (e.g., from 0 to 1, from 1 to 2, from 1 to 3, from 1 to 10, from 1 to 6, from 4 to 10, or from 6 to 10), or X at each occurrence is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is an integer from 1 to 3;

wherein when Z is Gln [SEQ ID NO. 2], the peptide of Formula (A) is a peptide of Formula (II):

(II)  [SEQ ID NO. 2]
[Mpa-Tyr-Phe-Gln-Asn-Cys-Pro-B(X)$_a$-Gly-NH$_2$]

wherein:

B is any one of L-Lys, D-Lys, L-Orn, D-Orn, L-Dab, D-Dab, L-Dap, or D-Dap, and

X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is an integer from 6 to 10, or X at each occurrence is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is an integer from 1 to 3; and wherein the composition has a therapeutic index of at least 20 (e.g., at least 30, at least 40, at least 50, at least 60, at least 70, at least 80, at least 90, or at least 100).

In some embodiments, Z is Hgn and B is Lys, X is optionally Gly, and a is 0, 1, 2, 3, 4, 5, 6, 7, 8, 9, or 10. In some embodiments, Z is Hgn, X is Gly, and a is 6, 7, 8, 9, or 10. In some embodiments, Z is Gln, X is Gly, and a is 6, 7, 8, 9, or 10.

In some embodiments, the present disclosure features a peptide of Formula (I)

(I)
[SEQ ID NO. 1]
[Mpa-Tyr-Phe-Hgn-Asn-Cys-Pro-B(X)$_a$-Gly-NH$_2$]

or a pharmaceutically effective salt thereof, wherein:

the Mpa and Cys residues are covalently connected with a disulfide bond;

B is any one of L-Lys, D-Lys, L-Orn, D-Orn, L-Dab, D-Dab, L-Dap, or D-Dap;

X is an amino acid residue, and at each occurrence, is independently selected from Gly, L-Ala, D-Ala, L-Lys, D-Lys, L-Orn, D-Orn, L-Glu, D-Glu, L-Asp, and D-Asp, and a is an integer from 0 to 10; or X is a moiety derived from a non-alpha primary amino group-containing C$_{3-12}$ fatty acid, and a is an integer from 1 to 3.

In some embodiments, in Formula (A) or Formula (I), X, at each occurrence, is independently selected from Gly, Ala, Lys, Orn, Glu, and Asp.

In some embodiments, in Formula (A) or Formula (I), X, at each occurrence, is independently selected from Gly, Ala, Lys, In some embodiments, in Formula (I), when X is an amino acid residue as defined in any of the embodiments above, and a can be an integer from 0 to 10, from 0 to 1, from 1 to 2, from 2 to 3, from 3 to 4, from 4 to 5, from 1 to 4, from 1 to 6, from 1 to 10, from 2 to 3, from 3 to 4, from 4 to 5, from 4 to 10, from 5 to 6, from 6 to 8, from 6 to 10, or from 8 to 10.

In some embodiments, in Formula (A) or Formula (I), when X, at each occurrence, is a moiety derived from a non-alpha primary amino group-containing fatty acid, the fatty acid be a C$_{3-12}$ fatty acid, a C$_{3-6}$ fatty acid, a C$_{3-10}$ fatty acid, a C$_{4-12}$ fatty acid, a C$_{4-6}$ fatty acid, a C$_{4-10}$ fatty acid, a C$_{6-10}$ fatty acid, a C$_{8-10}$ fatty acid, or a C$_{10-12}$ fatty acid.

In some embodiments, when X, at each occurrence, is a moiety derived from a non-alpha primary amino group-containing C$_{3-12}$ fatty acid, a is 1, 2 or 3 (e.g., 1 or 2, 2 or 3, or 1 or 3).

In some embodiments, in Formula (I), B is L-Lys. In some embodiments, in Formula (I), B is D-Lys. In some embodiments, in Formula (I), B is L-Orn. In some embodiments, in Formula (I), B is D-Orn. In some embodiments, in Formula (I), B is L-Dab. In some embodiments, in Formula (I), B is D-Dab. In some embodiments, in Formula (I), B is L-Dap. In some embodiments, in Formula (I), B is D-Dap.

In some embodiments, in the compound of Formula (A) or Formula (I), B is Lys and X includes Lys.

In some embodiments, in the peptide of Formula (I), B is L-Lys, X is Gly, and a is 1, 2, 3, 4, 5, 6, 7, 8, 9, or 10.

In some embodiments, in the peptide of Formula (I), B is D-Lys, X is Gly, and a is 1, 2, 3, 4, 5, 6, 7, 8, 9, or 10.

In some embodiments, in the peptide of Formula (I), B is L-Dap, X is Gly, and a is 1, 2, 3, 4, 5, 6, 7, 8, 9, or 10.

In some embodiments, in the peptide of Formula (I), B is D-Dap, X is Gly, and a is 1, 2, 3, 4, 5, 6, 7, 8, 9, or 10.

In some embodiments, in the peptide of Formula (I), B is L-Orn, X is Gly, and a is 1, 2, 3, 4, 5, 6, 7, 8, 9, or 10.

In some embodiments, in the peptide of Formula (I), B is D-Orn, X is Gly, and a is 1, 2, 3, 4, 5, 6, 7, 8, 9, or 10.

In some embodiments, in the peptide of Formula (I), B is L-Dab, X is Gly, and a is 1, 2, 3, 4, 5, 6, 7, 8, 9, or 10.

In some embodiments, in the peptide of Formula (I), B is D-Dab, X is Gly, and a is 1, 2, 3, 4, 5, 6, 7, 8, 9, or 10.

In some embodiments, in the peptide of Formula (I), B is Lys, and a is 0.

In some embodiments, in the peptide of Formula (I), B is Lys, X is Gly, and a is 1.

In some embodiments, in the peptide of Formula (I), B is Lys, X is Gly, and a is 2.

In some embodiments, in the peptide of Formula (I), B is Lys, X is Gly, and a is 3.

In some embodiments, in the peptide of Formula (I), B is Lys, X is Gly, and a is 4.

In some embodiments, in the peptide of Formula (I), B is Lys, X is Gly, and a is 5.

In some embodiments, in the peptide of Formula (A) or Formula (I), B is Lys, X is Gly, and a is 6.

In some embodiments, in the peptide of Formula (A) or Formula (I), B is Lys, X is Gly, and a is 7.

In some embodiments, in the peptide of Formula (A) or Formula (I), B is Lys, X is Gly, and a is 8.

In some embodiments, in the peptide of Formula (A) or Formula (I), B is Lys, X is Gly, and a is 9.

In some embodiments, in the peptide of Formula (A) or Formula (I), B is Lys, X is Gly, and a is 10.

In some embodiments, in the peptide of Formula (I), B is D-Lys, and a is 0.

In some embodiments, in the peptide of Formula (I), B is D-Lys, X is Gly, and a is 1.

In some embodiments, in the peptide of Formula (I), B is D-Lys, X is Gly, and a is 2.

In some embodiments, in the peptide of Formula (I), is D-Lys, X is Gly, and a is 3.

In some embodiments, in the peptide of Formula (I), B is D-Lys, X is Gly, and a is 4.

In some embodiments, in the peptide of Formula (I), B is D-Lys, X is Gly, and a is 5.

In some embodiments, in the peptide of Formula (A) or Formula (I), B is D-Lys, X is Gly, and a is 6.

In some embodiments, in the peptide of Formula (A) or Formula (I), B is D-Lys, X is Gly, and a is 7.

In some embodiments, in the peptide of Formula (A) or Formula (I), B is D-Lys, X is Gly, and a is 8.

In some embodiments, in the peptide of Formula (A) or Formula (I), B is D-Lys, X is Gly, and a is 9.

In some embodiments, in the peptide of Formula (A) or Formula (I), B is D-Lys, X is Gly, and a is 10.

In some embodiments, in the peptide of Formula (I), B is Orn, and a is 0.

In some embodiments, in the peptide of Formula (I), B is Orn, X is Gly, and a is 1.

In some embodiments, in the peptide of Formula (I), B is Orn, X is Gly, and a is 2.

In some embodiments, in the peptide of Formula (I), B is Orn, X is Gly, and a is 3.

In some embodiments, in the peptide of Formula (I), B is Orn, X is Gly, and a is 4.

In some embodiments, in the peptide of Formula (I), B is Orn, X is Gly, and a is 5.

In some embodiments, in the peptide of Formula (A) or Formula (I), B is Orn, X is Gly, and a is 6.

In some embodiments, in the peptide of Formula (A) or Formula (I), B is Orn, X is Gly, and a is 7.

In some embodiments, in the peptide of Formula (A) or Formula (I), B is Orn, X is Gly, and a is 8.

In some embodiments, in the peptide of Formula (A) or Formula (I), B is Orn, X is Gly, and a is 9.

In some embodiments, in the peptide of Formula (A) or Formula (I), B is Orn, X is Gly, and a is 10.

In some embodiments, in the peptide of Formula (I), B is D-Orn, and a is 0.

In some embodiments, in the peptide of Formula (I), B is D-Orn, X is Gly, and a is 1.

In some embodiments, in the peptide of Formula (I), B is D-Orn, X is Gly, and a is 2.

In some embodiments, in the peptide of Formula (I), B is D-Orn, X is Gly, and a is 3.

In some embodiments, in the peptide of Formula (I), B is D-Orn, X is Gly, and a is 4.

In some embodiments, in the peptide of Formula (I), B is D-Orn, X is Gly, and a is 5.

In some embodiments, in the peptide of Formula (A) or Formula (I), B is D-Orn, X is Gly, and a is 6.

In some embodiments, in the peptide of Formula (A) or Formula (I), B is D-Orn, X is Gly, and a is 7.

In some embodiments, in the peptide of Formula (A) or Formula (I), B is D-Orn, X is Gly, and a is 8.

In some embodiments, in the peptide of Formula (A) or Formula (I), B is D-Orn, X is Gly, and a is 9.

In some embodiments, in the peptide of Formula (A) or Formula (I), B is D-Orn, X is Gly, and a is 10.

In some embodiments, in the peptide of Formula (I), B is Dap, and a is 0.

In some embodiments, in the peptide of Formula (I), B is Dap, X is Gly, and a is 1.

In some embodiments, in the peptide of Formula (I), B is Dap, X is Gly, and a is 2.

In some embodiments, in the peptide of Formula (I), B is Dap, X is Gly, and a is 3.

In some embodiments, in the peptide of Formula (I), B is Dap, X is Gly, and a is 4.

In some embodiments, in the peptide of Formula (I), B is Dap, X is Gly, and a is 5.

In some embodiments, in the peptide of Formula (A) or Formula (I), B is Dap, X is Gly, and a is 6.

In some embodiments, in the peptide of Formula (A) or Formula (I), B is Dap, X is Gly, and a is 7.

In some embodiments, in the peptide of Formula (A) or Formula (I), B is Dap, X is Gly, and a is 8.

In some embodiments, in the peptide of Formula (A) or Formula (I), B is Dap, X is Gly, and a is 9.

In some embodiments, in the peptide of Formula (A) or Formula (I), B is Dap, X is Gly, and a is 10.

In some embodiments, in the peptide of Formula (I), B is D-Dap, and a is 0.

In some embodiments, in the peptide of Formula (I), B is D-Dap, X is Gly, and a is 1.

In some embodiments, in the peptide of Formula (I), B is D-Dap, X is Gly, and a is 2.

In some embodiments, in the peptide of Formula (I), B is D-Dap, X is Gly, and a is 3.

In some embodiments, in the peptide of Formula (I), B is D-Dap, X is Gly, and a is 4.

In some embodiments, in the peptide of Formula (I), B is D-Dap, X is Gly, and a is 5.

In some embodiments, in the peptide of Formula (A) or Formula (I), B is D-Dap, X is Gly, and a is 6.

In some embodiments, in the peptide of Formula (A) or Formula (I), B is D-Dap, X is Gly, and a is 7.

In some embodiments, in the peptide of Formula (A) or Formula (I), B is D-Dap, X is Gly, and a is 8.

In some embodiments, in the peptide of Formula (A) or Formula (I), B is D-Dap, X is Gly, and a is 9.

In some embodiments, in the peptide of Formula (A) or Formula (I), B is D-Dap, X is Gly, and a is 10.

In some embodiments, in the peptide of Formula (I), B is Dab, and a is 0.

In some embodiments, in the peptide of Formula (I), B is Dab, X is Gly, and a is 1.

In some embodiments, in the peptide of Formula (I), B is Dab, X is Gly, and a is 2.

In some embodiments, in the peptide of Formula (I), B is Dab, X is Gly, and a is 3.

In some embodiments, in the peptide of Formula (I), B is Dab, X is Gly, and a is 4.

In some embodiments, in the peptide of Formula (I), B is Dab, X is Gly, and a is 5.

In some embodiments, in the peptide of Formula (A) or Formula (I), B is Dab, X is Gly, and a is 6.

In some embodiments, in the peptide of Formula (A) or Formula (I), B is Dab, X is Gly, and a is 7.

In some embodiments, in the peptide of Formula (A) or Formula (I), B is Dab, X is Gly, and a is 8.

In some embodiments, in the peptide of Formula (A) or Formula (I), B is Dab, X is Gly, and a is 9.

In some embodiments, in the peptide of Formula (A) or Formula (I), B is Dab, X is Gly, and a is 10.

In some embodiments, in the peptide of Formula (I), B is D-Dab, and a is 0.

In some embodiments, in the peptide of Formula (I), B is D-Dab, X is Gly, and a is 1.

In some embodiments, in the peptide of Formula (I), B is D-Dab, X is Gly, and a is 2.

In some embodiments, in the peptide of Formula (I), B is D-Dab, X is Gly, and a is 3.

In some embodiments, in the peptide of Formula (I), B is D-Dab, X is Gly, and a is 4.

In some embodiments, in the peptide of Formula (I), B is D-Dab, X is Gly, and a is 5.

In some embodiments, in the peptide of Formula (A) or Formula (I), B is D-Dab, X is Gly, and a is 6.

In some embodiments, in the peptide of Formula (A) or Formula (I), B is D-Dab, X is Gly, and a is 7.

In some embodiments, in the peptide of Formula (A) or Formula (I), B is D-Dab, X is Gly, and a is 8.

In some embodiments, in the peptide of Formula (A) or Formula (I), B is D-Dab, X is Gly, and a is 9.

In some embodiments, in the peptide of Formula (A) or Formula (I), B is D-Dab, X is Gly, and a is 10.

In some embodiments, in the peptide of Formula (A) or Formula (I), a is not 0.

In some embodiments, in the peptide of Formula (A) or Formula (I), B is Lys, X, at each occurrence, is a moiety derived from a non-alpha primary amino group-containing $C_3$-$C_{12}$ fatty acid (e.g., $C_3$-$C_6$, $C_4$-$C_{10}$, $C_6$-$C_{10}$, $C_8$-$C_{10}$, or $C_{10}$-$C_{12}$ fatty acid) and a is 1.

In some embodiments, in the peptide of Formula (A) or Formula (I), B is Lys, X is a moiety derived from a non-alpha primary amino group-containing $C_{12}$ fatty acid, and a is 1.

In some embodiments, in the peptide of Formula (A) or Formula (I), B is Lys, X is a moiety derived from a non-alpha primary amino group-containing $C_{10}$ fatty acid, and a is 1.

In some embodiments, in the peptide of Formula (A) or Formula (I), B is Lys, X is a moiety derived from a non-alpha primary amino group-containing $C_8$ fatty acid, and a is 1.

In some embodiments, in the peptide of Formula (A) or Formula (I), B is Lys, X is a moiety derived from a non-alpha primary amino group-containing $C_6$ fatty acid, and a is 1.

In some embodiments, in the peptide of Formula (A) or Formula (I), B is Lys, X is a moiety derived from a non-alpha primary amino group-containing $C_6$ fatty acid, and a is 2.

In some embodiments, in the peptide of Formula (A) or Formula (I), B is Lys, X is a moiety derived from a non-alpha primary amino group-containing $C_4$ fatty acid, and a is 1.

In some embodiments, in the peptide of Formula (A) or Formula (I), B is Lys, X is a moiety derived from a non-alpha primary amino group-containing $C_4$ fatty acid, and a is 2.

In some embodiments, in the peptide of Formula (A) or Formula (I), B is Lys, X is a moiety derived from a non-alpha primary amino group-containing $C_4$ fatty acid, and a is 3.

In some embodiments, in the peptide of Formula (A) or Formula (I), B is Lys, X is a moiety derived from a non-alpha primary amino group-containing $C_3$ fatty acid, and a is 1.

In some embodiments, in the peptide of Formula (A) or Formula (I), B is Lys, X is a moiety derived from a non-alpha primary amino group-containing $C_3$ fatty acid, and a is 2.

In some embodiments, in the peptide of Formula (A) or Formula (I), B is Lys, X is a moiety derived from a non-alpha primary amino group-containing $C_3$ fatty acid, and a is 3.

In some embodiments, in the peptide of Formula (A) or Formula (I), B is Lys, and X is a moiety derived from a non-alpha primary amino group-containing fatty acid selected from beta amino propanoic (propionic) acid, 4-amino butanoic(butyric) acid, 5-amino pentanoic (valeric) acid, 6-amino hexanoic (caproic) acid, 7-amino heptanoic (enanthic) acid, 8-amino octanoic(caprylic) acid, 9-amino nonanoic(pelargonic) acid, 10-amino decanoic (capric) acid, 11-amino undecanoic(undecylic) acid, and 12-amino dodecanoic (lauric) acid.

In some embodiments, unless B is defined differently in the embodiments of Formula (A) or Formula (I) above, B is Lys.

The peptide of Formula (A) or Formula (I) can be a V1a partial agonist. The V1a partial agonist partially activates a V1a receptor.

The composition including a peptide of Formula (A) or Formula (I), in any of the above-mentioned embodiments, can have a therapeutic index of at least 20 (e.g., at least 30, at least 40, at least 50, at least 60, at least 70, at least 80, at least 90, or at least 100. The peptide of Formula (A) or Formula (I) has specificity for the V1a receptor.

The amino acid sequence $(X)_a$ can provide the ability to tune the solubility and/or the stability properties of the peptide of Formula (A) and/or Formula (I), so that the peptide can be tailored to suit the intended route of administration and the desired solubility, while maintaining a therapeutic index of at least 20 (e.g., at least 30, at least 40, at least 50, at least 60, at least 70, at least 80, at least 90, at least 100) without altering the partial V1a agonist properties. The therapeutic index is defined herein as the ratio NOAEL/NOEL. The stability of formulation can be measured, for example, by those skilled of ordinary skill in the art using established chromatography protocols. The solubility can be readily measured by those skilled in the art by centrifugation or filtration of a given formulation followed by chromatographic analysis of the supernatant solution or the filtrate. To ascertain the partial V1a agonist properties, the partial agonistic activity can be measured as described in the Examples below, both in vitro and in vivo. Furthermore, it is believed that the amino acid sequence for $(X)_a$ can provide a therapeutic agent that degrades slowly over time in vivo while releasing similarly active degradation intermediates that possess partial agonist activity. Thus, the compositions of the present disclosure can provide a prolonged partial V1a agonist presence in the blood over a sustained period of time.

The present disclosure also describes a peptide of Formula (II):

(II)
[SEQ ID NO. 2]
[Mpa-Tyr-Phe-Gln-Asn-Cys-Pro-B(X)$_a$-Gly-NH$_2$]

or a pharmaceutically effective salt thereof, wherein:

the Mpa and Cys residues are covalently connected with a disulfide bond,

B is any one of L-Lys, D-Lys, L-Orn, D-Orn, L-Dab, D-Dab, L-Dap, or D-Dap,

X is an amino acid residue and at each occurrence, is independently selected from Gly, L-Ala, D-Ala, L-Lys, D-Lys, L-Orn, D-Orn, L-Glu, D-Glu, L-Asp, and D-Asp, and a is an integer from 6 to 10; or X, at each occurrence, is a moiety derived from a non-alpha primary amino group-containing $C_{3-12}$ fatty acid and a is an integer from 1 to 3.

The peptide of Formula (II) can have a therapeutic index of at least 20 (e.g., at least 30, at least 40, at least 50, at least 60, at least 70, at least 80, at least 90, or at least 100). The peptide can be a V1a partial agonist.

In some embodiments, in peptide of Formula (II), when X is an amino acid residue, a can be an integer of from 3 to 4, from 4 to 6, from 4 to 8, from 4 to 10, from 4 to 12, from 6 to 10, from 8 to 10, or from 10 to 12.

In some embodiments, in the peptide of Formula (II), X is Gly, and a is 6, 7, 8, 9, and/or 10.

In some embodiments, in the peptide of Formula (II), X, at each occurrence, is a moiety derived from a non-alpha primary amino group-containing a $C_3$-$C_{12}$ fatty acid (e.g., $C_4$-$C_{12}$, $C_4$-$C_6$, $C_4$-$C_{10}$, $C_3$-$C_6$, $C_6$-$C_{10}$, $C_8$-$C_{10}$, or $C_{10}$-$C_{12}$ fatty acid).

In some embodiments, in the peptide of Formula (II), X is non-alpha primary amine containing 12 carbon fatty acid, and a is 1.

In some embodiments, in the peptide of Formula (II), X is a moiety derived from a non-alpha primary amino group-containing $C_{10}$ fatty acid, and a is 1.

In some embodiments, in the peptide of Formula (II), X is a moiety derived from a non-alpha primary amino group-containing $C_8$ fatty acid, and a is 1.

In some embodiments, in the peptide of Formula (II), X is a moiety derived from a non-alpha primary amino group-containing $C_6$ fatty acid, and a is 1.

In some embodiments, in the peptide of Formula (II), X is a moiety derived from a non-alpha primary amino group-containing $C_6$ fatty acid, and a is 2.

In some embodiments, in the peptide of Formula (II), Z is a moiety derived from a non-alpha primary amino group-containing $C_4$ fatty acid, and a is 1.

In some embodiments, in the peptide of Formula (II), X is a moiety derived from a non-alpha primary amino group-containing $C_4$ fatty acid, and a is 2.

In some embodiments, in the peptide of Formula (II), X is a moiety derived from a non-alpha primary amino group-containing $C_4$ fatty acid, and a is 3.

In some embodiments, in the peptide of Formula (II), X is a moiety derived from a non-alpha primary amino group-containing $C_3$ fatty acid, and a is 1.

In some embodiments, in the peptide of Formula (II), X is a moiety derived from a non-alpha primary amino group-containing $C_3$ fatty acid, and a is 2.

In some embodiments, in the peptide of Formula (II), X is a moiety derived from a non-alpha primary amino group-containing $C_3$ fatty acid, and a is 3.

In some embodiments, in the peptide of Formula (II), X is a moiety derived from a non-alpha primary amino group-containing fatty acid selected from beta amino propanoic (propionic) acid, 4-amino butanoic(butyric) acid, 5-amino pentanoic (valeric) acid, 6-amino hexanoic (caproic) acid, 7-amino heptanoic (enanthic) acid, 8-amino octanoic (caprylic) acid, 9-amino nonanoic(pelargonic) acid, 10-amino decanoic (capric) acid, 11-amino undecanoic(undecylic) acid, and 12-amino dodecanoic (lauric) acid; and a is from 1 to 3.

In some embodiments, the peptide of Formula (II) does not include a $(X)_a$ moiety where X is Gly and a is 1, 2, or 3. In some embodiments, the peptide of Formula (II) does not include a $(X)_a$ moiety where X is Gly and a is 1, 2, 3, 4, or 5. In some embodiments, the peptide of Formula (II) does not include a $(X)_a$ moiety where X is Gly, L- or D-Ala, L- or D-Val, L- or D-Leu, L- or D Pro, L- or D Trp, L- or D Tyr, and/or L- or D-Phe, and a is 1, 2, or 3. In some embodiments, the peptide of Formula (II) does not include a $(X)_a$ moiety where X is Gly, L-Ala, L-Val, L-Leu, L-Pro, L-Trp, L-Tyr, and/or L-Phe, and a is 1, 2, or 3. In some embodiments, the peptide of Formula (II) does not include a $(X)_a$ moiety where X is Gly, L- or D-Ala, L- or D-Val, L- or D-Leu, L- or D Pro, L- or D Trp, L- or D Tyr, and/or L- or D-Phe, and a is 1, 2, 3, 4, or 5. In some embodiments, the peptide of Formula (II) does not include a $(X)_a$ moiety where X is Gly, L-Ala, L-Val, L-Leu, L-Pro, L-Trp, L-Tyr, and/or L-Phe, and a is 1, 2, 3, 4, or 5.

In some embodiments, unless B is defined differently in the embodiments of Formula (II) above, B is Lys.

The peptide of Formula (II) can be a V1a partial agonist. The V1a partial agonist partially activates a V1a receptor.

The amino acid sequence for $(X)_a$ can provide the ability to tune the solubility and/or the stability properties of the peptide of Formula (II), so that the peptide can be tailored to suit the intended route of administration and the desired solubility, while maintaining a therapeutic index of at least 20 (e.g., at least 30, at least 40, at least 50, at least 60, at least 70, at least 80, at least 90, at least 100) without altering the partial V1a agonist properties. The therapeutic index is defined herein as the ratio NOAEL/NOEL. The stability of formulation and the solubility measurements are as described above. To ascertain the partial V1a agonist properties, the partial agonistic activity can be measured as described in the Examples below, both in vitro and in vivo. Furthermore, it is believed that the amino acid sequence for $(X)_a$ can provide a therapeutic agent that degrades slowly over time in vivo while releasing similarly active degradation intermediates that possess partial agonist activity. By having $(X)_a$ where a is 6-10 in formula II, surprisingly, the V1a partial agonist activity can be prolonged. Thus, the compositions of the present disclosure can provide a prolonged partial V1a agonist presence in the blood over a sustained period of time.

In some embodiments, the V1a partial agonist of the compositions of the present disclosure includes a peptide of Formula (I), wherein X is Gly; and/or a peptide of Formula (II), wherein B is Lys, and X is Gly, and/or a pharmaceutically acceptable salt thereof.

In some embodiments, the V1a partial agonist of the compositions of the present disclosure includes a peptide of Formula (I), wherein X is Gly and a is 6; and/or a peptide of Formula (II), wherein B is Lys, X is Gly, and a is 6, and/or a pharmaceutically acceptable salt thereof.

In some embodiments, the V1a partial agonist of the compositions of the present disclosure includes a peptide of Formula (I), wherein X is Gly and a is 7; and/or a peptide of Formula (II), wherein B is Lys, X is Gly, and a is 7, and/or a pharmaceutically acceptable salt thereof.

In some embodiments, the V1a partial agonist of the compositions of the present disclosure includes a peptide of Formula (I), wherein X is Gly and a is 8; and/or a peptide of Formula (II), wherein B is Lys, X is Gly, and a is 8, and/or a pharmaceutically acceptable salt thereof.

In some embodiments, the V1a partial agonist of the compositions of the present disclosure includes a peptide of Formula (I), wherein X is Gly and a is 9; and/or a peptide of Formula (II), wherein B is Lys, X is Gly, and a is 9, and/or a pharmaceutically acceptable salt thereof.

In some embodiments, the V1a partial agonist of the compositions of the present disclosure includes a peptide of Formula (I), wherein X is Gly and a is 10; and/or a peptide of Formula (II), wherein B is Lys, X is Gly, and a is 10, and/or a pharmaceutically acceptable salt thereof.

In some embodiments, a pharmaceutical composition for partially activating V1a receptor includes the aforementioned peptide of Formula (I), Formula (II), and/or a pharmaceutically acceptable salt thereof; and a pharmaceutically acceptable excipient(s) and/or buffer. The buffer can have an optimal buffering pH of between 3.5 and 6.5, such as a citrate buffer, acetate buffer, succinate buffer, and/or histidine buffer. The buffer concentration can be less than 100 mM (e.g., less than 90 mM, less than 75 mM, less than 60 mM, less than 45 mM, less than 30 mM, less than 15 mM, less than 10 mM, or less than 5 mM).

The present disclosure further features a use of a peptide of Formula (B), (B)
[SEQ ID NOS. 7 and 4]
[X'-Tyr-Phe-Gln-Asn-Cys-Pro-Lys(Z)$_d$-Gly-NH$_2$]

or a pharmaceutically acceptable salt thereof,
wherein:
X' is $(U)_c$-Cys or Mpa,
wherein when X' is $(U)_c$-Cys and $(Z)_d$ is absent [SEQ ID NO. 7], the peptide of Formula (B) is a peptide of Formula (III)

(III)
[SEQ ID NO. 7]
[(U)$_c$-Cys-Tyr-Phe-Gln-Asn-Cys-Pro-Lys-Gly-NH$_2$]

wherein
the 2 Cys residues are covalently connected with a disulfide bond,
U is an amino acid residue and at each occurrence, is independently selected from Gly, L-Ala, D-Ala, L-Lys, D-Lys, L-Orn, D-Orn, L-Glu, D-Glu, L-Asp, and D-Asp, and c is the number of U and is an integer of from 0 to 10; and
wherein when X' is Mpa [SEQ ID NO. 4], the peptide of Formula (B) is a peptide of Formula (IV)

(IV)

[SEQ ID NO. 4]

[Mpa-Tyr-Phe-Gln-Asn-Cys-Pro-Lys(Z)$_d$-Gly-NH$_2$]

wherein the Mpa and Cys residues are covalently connected with a disulfide bond, Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and d is the number of Z and is an integer from 0 to 5.

In some embodiments, the peptides of Formula (III) or (IV) can be full or partial V1a agonists, but the activity can be modulated when used with a V2 antagonist.

In some embodiments, the peptide of Formula (B) is a peptide of Formula (III), (III)

[SEQ ID NO. 7]

[(U)$_c$-Cys-Tyr-Phe-Gln-Asn-Cys-Pro-Lys-Gly-NH$_2$]

or a pharmaceutically effective salt thereof, wherein:

the 2 Cys residues are covalently connected with a disulfide bond,

U is an amino acid residue and at each occurrence, is independently selected from Gly, L-Ala, D-Ala, L-Lys, D-Lys, L-Orn, D-Orn, L-Glu, D-Glu, L-Asp, and D-Asp, and c is a number of amino acid residue(s) U and is an integer of from 0 to 10 (e.g., from 1 to 10, from 4 to 10, or from 6 to 10). The peptide can be a V1a agonist.

In some embodiments, the peptide of Formula (III) can behave as a full or a partial V1a agonist, when used with a V2 antagonist.

In some embodiments, for the peptide of Formula (III), c is not 0. In some embodiments, one or both of the termini of the peptide of Formula (III) do not include an alkyl group (e.g., an alkyl group having 3 to 36 carbon units). In some embodiments, one or both of the termini of the peptide of Formula (III) do not include an alkyl group having 3 to 36 carbon units, nitrilotriacetic acid, imido diacetic acid, or one or more histidine residue. In some embodiments, the peptide of Formula (III) does not include a peptide where U is Gly and/or His, and c is an integer from 1-6, the peptide optionally including a terminal alkyl group. In some embodiments, (U)$_c$ in the peptide of formula (III) does not include Leu, Phe, Tyr, Trp, Pro, Gly-Gly, Leu-Leu, Gly-Pro, sarcosyl-Gly, and/or Gly-Gly-Gly.

In some embodiments, the peptide of Formula (B) is a peptide of Formula (IV), (IV)

[SEQ ID NO. 4]

[Mpa-Tyr-Phe-Gln-Asn-Cys-Pro-Lys(Z)$_d$-Gly-NH$_2$]

or a pharmaceutically effective salt thereof, wherein:

the Mpa and Cys residues are covalently connected with a disulfide bond,

Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and d is a number of amino acid residue(s) Z and is an integer from 0 to 5. The peptide can be a V1a agonist.

In some embodiments, the peptide of Formula (IV) can behave as a full or a partial V1a agonist, when used with a V2 antagonist. In some embodiments, the compositions of the present disclosure include a pharmaceutically acceptable salt of a peptide of Formula (I), Formula (II), Formula (III), Formula (IV).

In some embodiments, any one of the aforementioned compositions can be in the form of a pharmaceutical formulation, the pharmaceutical formulation including a peptide of Formula (I), Formula (II), Formula (III), Formula (IV), and/or a pharmaceutically acceptable salt thereof, and can further optionally include one or more pharmaceutically acceptable excipient(s) and/or a buffer. As an example, the compositions can optionally include a buffer having an optimal buffering pH of between 3.5 and 6.5, such as a citrate buffer, acetate buffer, succinate buffer, and/or histidine buffer. The buffer salt concentration can be less than 100 mM (e.g., less than 90 mM, less than 75 mM, less than 60 mM, less than 45 mM, less than 30 mM, less than 15 mM, less than 10 mM, or less than 5 mM).

Methods of Treatment

In some embodiments, the present disclosure provides a method of treating a subject having one or more of the following conditions: liver fibrosis, cirrhosis, portal hypertension, ascites, varices (e.g., esophageal varices, gastric varices), bleeding (e.g., variceal bleeding), arterial hypotension, and/or hepatorenal syndrome, by administering a therapeutically effective dose of a pharmaceutical composition including a peptide of any embodiments of Formula (I) or Formula (II) as described in the section entitled "Compositions" above, and/or a pharmaceutically acceptable salt thereof. For example, the subject can have hypotension where the mean arterial pressure is below 95 mm Hg (e.g., below 90 mm Hg, below 85 mm Hg, below 80 mm Hg, below 75 mm Hg, or below 70 mm Hg). As another example, the subject can have cirrhosis and a mean arterial pressure below 95 mm Hg (e.g., below 90 mm Hg, below 85 mm Hg, below 80 mm Hg, below 75 mm Hg, below 70 mm Hg). In some embodiments, the subject has liver fibrosis. In certain embodiments, the subject has cirrhosis. In some embodiments, the subject has portal hypertension. In certain embodiments, the subject has ascites. In some embodiments, the subject has esophageal varices. In certain embodiments, the subject has gastric varices. In some embodiments, the subject has variceal bleeding. In some embodiments, the subject has mean arterial pressure below 95 mm Hg (e.g., below 90 mm Hg, below 85 mm Hg, below 80 mm Hg, below 75 mm Hg, or below 70 mm Hg).

As discussed above, the pharmaceutical composition can further include pharmaceutically acceptable excipient(s) and/or a buffer having an optimal buffering pH of between 3.5 and 6.5, such as a citrate buffer, acetate buffer, succinate buffer, and/or histidine buffer. The buffer salt concentration can be less than 100 mM (e.g., less than 90 mM, less than 75 mM, less than 60 mM, less than 45 mM, less than 30 mM, less than 15 mM, less than 10 mM, or less than 5 mM).

In some embodiments, the present disclosure features a method of treating a subject with one or more of the following conditions: liver fibrosis, cirrhosis, portal hypertension, ascites, esophageal varices, gastric varices, bleeding, arterial hypotension, and/or hepatorenal syndrome, including administering a therapeutically effective dose of a pharmaceutical composition including any of the aforementioned embodiments of peptide of Formula (I), wherein B is Lys, and/or a pharmaceutically acceptable salt thereof, and further optionally including a pharmaceutically acceptable excipient and/or buffer.

In some embodiments, the present disclosure provides a method of treating a subject with one or more of the following conditions: liver fibrosis, cirrhosis, portal hypertension, ascites, esophageal varices, gastric varices, bleeding, arterial hypotension, and hepatorenal syndrome, including administering a therapeutically effective dose of a pharmaceutical composition including the aforementioned embodiments of peptide of Formula (I), wherein B is Lys and X is Gly, and/or a pharmaceutically acceptable salt thereof, and further optionally including a pharmaceutically acceptable excipient and/or buffer.

In some embodiments, the present disclosure provides a method of treating a subject with one or more of the following conditions: liver fibrosis, cirrhosis, portal hypertension, ascites, esophageal varices, gastric varices, bleeding, arterial hypotension, and hepatorenal syndrome, including administering a therapeutically effective dose of a pharmaceutical composition including the aforementioned peptide of Formula (I), wherein B is Lys, X is Gly, and a is 6, and/or a pharmaceutically acceptable salt thereof, and further optionally including a pharmaceutically acceptable excipient and/or buffer.

In some embodiments, the present disclosure provides a method of treating a subject with one or more of the following conditions: liver fibrosis, cirrhosis, portal hypertension, ascites, esophageal varices, gastric varices, bleeding, arterial hypotension, and hepatorenal syndrome, including administering a therapeutically effective dose of a pharmaceutical composition including the aforementioned peptide of Formula (I), wherein B is Lys, X is moiety derived from a non-alpha primary amino group-containing $C_{12}$ fatty acid, and a is 1, and/or a pharmaceutically acceptable salt thereof, and further optionally including a pharmaceutically acceptable excipient and/or buffer.

For example, a method of treating a subject with one or more of the following conditions: liver fibrosis, cirrhosis, portal hypertension, ascites, esophageal varices, gastric varices, bleeding, arterial hypotension, and hepatorenal syndrome, can include administering a therapeutically effective dose of a pharmaceutical composition including any embodiment of the aforementioned peptide of Formula (I), for example, wherein B is Lys, X is non-alpha primary amine containing fatty acid with 10 carbon unit, and a is 1, and/or a pharmaceutically acceptable salt thereof, wherein B is Lys, X is non-alpha primary amine containing fatty acid with 8 carbon unit, and a is 1, and/or a pharmaceutically acceptable salt thereof, wherein B is Lys, X is non-alpha primary amine containing fatty acid with 6 carbon unit, and a is 1, and/or a pharmaceutically acceptable salt thereof, wherein B is Lys, X is non-alpha primary amine containing fatty acid with 6 carbon unit, and a is 2, and/or a pharmaceutically acceptable salt thereof, wherein B is Lys, X is non-alpha primary amine containing fatty acid with 4 carbon unit, and a is 1, and/or a pharmaceutically acceptable salt thereof, wherein B is Lys, X is non-alpha primary amine containing fatty acid with 4 carbon unit, and a is 2, and/or a pharmaceutically acceptable salt thereof, wherein B is Lys, X is non-alpha primary amine containing fatty acid with 4 carbon unit, and a is 3, and/or a pharmaceutically acceptable salt thereof, wherein B is Lys, X is non-alpha primary amine containing fatty acid with 3 carbon unit, and a is 1, and/or a pharmaceutically acceptable salt thereof, wherein B is Lys, X is non-alpha primary amine containing fatty acid with 3 carbon unit, and a is 2, and/or a pharmaceutically acceptable salt thereof, and/or wherein B is Lys, X is non-alpha primary amine containing fatty acid with 3 carbon unit, and a is 3, and/or a pharmaceutically acceptable salt thereof, and each pharmaceutical composition further optionally includes a pharmaceutically acceptable excipient and/or buffer.

In some embodiments, a method of treating a subject having a mean arterial pressure below 95 mm Hg (e.g., below 90 mm Hg, below 85 mm Hg, below 80 mm Hg, below 75 mm Hg, or below 70 mm Hg); a method of treating a subject with cirrhosis and with mean arterial pressure below 95 mm Hg (e.g., below 90 mm Hg, below 85 mm Hg, below 80 mm Hg, below 75 mm Hg, or below 70 mm Hg); a method of treating a subject with cirrhosis; a subject with portal hypertension; a method of treating a subject with ascites; a method of treating a subject with esophageal varices; a method of treating a subject with gastric varices; a method of treating a subject with variceal bleeding; or a method of treating a subject with hepatorenal syndrome can each independently include administering a therapeutically effective dose of a pharmaceutical composition including:

the peptide of Formula (I) as described above, for example, wherein B is Lys and a is 0, or X is Gly and a is an integer of from 1 to 10 (e.g., preferably a is 6), and/or a pharmaceutically acceptable salt thereof; or the peptide of Formula (II) as described above, for example, wherein:
B is Lys, X is Gly and a is 6, 7, 8, 9, or 10, and/or a pharmaceutically acceptable salt thereof; or
the peptide of Formula (A) as described above, for example, wherein B is Lys, and
X is a moiety derived from a non-alpha primary amino group-containing $C_{12}$ fatty acid and a is 1, or
X is a moiety derived from a non-alpha primary amino group-containing $C_{10}$ fatty acid and a is 1, or
X is a moiety derived from a non-alpha primary amino group-containing $C_8$ fatty acid and a is 1, or
X is a moiety derived from a non-alpha primary amino group-containing $C_6$ fatty acid and a is 1, or
X is a moiety derived from a non-alpha primary amino group-containing $C_6$ fatty acid and a is 2, or
X is a moiety derived from a non-alpha primary amino group-containing $C_4$ fatty acid and a is 1, or
X is a moiety derived from a non-alpha primary amino group-containing $C_4$ fatty acid and a is 2, or
X is a moiety derived from a non-alpha primary amino group-containing $C_4$ fatty acid and a is 3, or
X is a moiety derived from a non-alpha primary amino group-containing $C_3$ fatty acid and a is 1, or
X is a moiety derived from a non-alpha primary amino group-containing $C_3$ fatty acid and a is 2, or
X is a moiety derived from a non-alpha primary amino group-containing $C_3$ fatty acid and a is 3; and/or
a pharmaceutically acceptable salt thereof, and wherein each pharmaceutical composition further optionally includes a pharmaceutically acceptable excipient and/or buffer.

In some embodiments, a method of treating a subject with hepatorenal syndrome includes administering a therapeutically effective dose of a pharmaceutical composition including the aforementioned peptide Formula (A), wherein X is a moiety derived from 12-amino dodecanoic (lauric) acid and a is 1; and/or a pharmaceutically acceptable salt thereof, and further optionally including a pharmaceutically acceptable excipient and/or buffer. In some embodiments, when the peptide of Formula (A) is a peptide of Formula (II), B is additionally Lys.

In some embodiments, a method of treating a subject with hepatorenal syndrome includes administering a therapeutically effective dose of a pharmaceutical composition including the aforementioned peptide of Formula (A), wherein X is a moiety derived from 8-amino octanoic(caprylic) acid and a is 1; and/or a pharmaceutically acceptable salt thereof, and further optionally including a pharmaceutically acceptable excipient and/or buffer. In some embodiments, when the peptide of Formula (A) is a peptide of Formula (II), B is additionally Lys.

In some embodiments, a method of treating a subject with hepatorenal syndrome includes administering a therapeutically effective dose of a pharmaceutical composition including the aforementioned peptide of Formula (A), wherein X is a moiety derived from 6-amino hexanoic(caproic) acid and a is 1; and/or a pharmaceutically acceptable salt thereof, and further optionally including a pharmaceutically acceptable excipient and/or buffer. In some embodiments, when the peptide of Formula (A) is a peptide of Formula (II), B is additionally Lys.

In some embodiments, a method of treating a subject with hepatorenal syndrome includes administering a therapeutically effective dose of a pharmaceutical composition including the aforementioned peptide of Formula (A), wherein X is a moiety derived from 4-amino butanoic(butyric) acid and a is 1; and/or a pharmaceutically acceptable salt thereof, and further optionally including a pharmaceutically acceptable excipient and/or buffer. In some embodiments, when the peptide of Formula (A) is a peptide of Formula (II), B is additionally Lys.

In some embodiments, a method of treating a subject with hepatorenal syndrome includes administering a therapeutically effective dose of a pharmaceutical composition including the aforementioned peptide of Formula (A), wherein X is a moiety derived from beta-amino propanoic (propionic) acid and a is 1; and/or a pharmaceutically acceptable salt thereof, and further optionally including a pharmaceutically acceptable excipient and/or buffer. In some embodiments, when the peptide of Formula (A) is a peptide of Formula (II), B is additionally Lys.

In some embodiments, in any of the aforementioned methods of treating a subject, the pharmaceutical composition is administered by an enteral route (e.g., oral, including drinking, swallowing, sublingual, buccal, and/or sublabial; and/or rectal/anal route).

In some embodiments, in any of the aforementioned methods of treating a subject, the pharmaceutical composition is administered by a parenteral route (e.g., an intravenous, subcutaneous, subdermal, intramuscular, intraperitoneal, intrapleural, and/or intranasal route).

In some embodiments, in any of the aforementioned methods of treating a subject, the pharmaceutical composition is administered as a bolus dose. For example, the pharmaceutical composition can be administered as an intravenous bolus dose and/or as a subcutaneous bolus dose. In certain embodiments, the pharmaceutical composition is administered as an intravenous bolus dose.

In some embodiments, in any of the aforementioned methods of treating a subject, the pharmaceutical composition is administered by intravenous infusion. For example, the pharmaceutical composition can be administered intravenously as a subcutaneous bolus.

In some embodiments, for any of the aforementioned methods of treating a subject, the dose is less than 500 nmol/Kg/day (e.g., less than 450 nmol/Kg/day, less than 300 nmol/Kg/day, less than 250 nmol/Kg/day, less than 200 nmol/Kg/day, less than 175 nmol/Kg/day, less than 150 nmol/Kg/day, less than 125 nmol/Kg/day, or less than 100 nmol/Kg/day); preferably less than 200 nmol/Kg/day (e.g., less than 175 nmol/Kg/day, less than 150 nmol/Kg/day, less than 125 nmol/Kg/day, less than 100 nmol/Kg/day, less than 90 nmol/Kg/day, less than 80 nmol/Kg/day, less than 70 nmol/Kg/day, or less than 50 nmol/Kg/day); more preferably less than 100 nmol/Kg/day (e.g., less than 90 nmol/Kg/day, less than 80 nmol/Kg/day, less than 60 nmol/Kg/day, less than 50 nmol/Kg/day, less than 40 nmol/Kg/day, less than 30 nmol/Kg/day, less than 20 nmol/Kg/day, or less than 10 nmol/Kg/day). In some embodiments, the dose limit can depend on whether the subject is also undergoing other drug treatment for the same or different indications, the mean arterial blood pressure, drug(s) that affects vascular volume, overall organ perfusion, and/or presence of ischemia.

In some embodiments, for any of the aforementioned methods of treating a subject, the dose can be less than 150 nmol/Kg/day (e.g., less than 140 nmol/Kg/day, less than 130 nmol/Kg/day, less than 120 nmol/Kg/day, less than 110 nmol/Kg/day, less than 100 nmol/Kg/day, less than 90 nmol/Kg/day, less than 80 nmol/Kg/day, less than 70 nmol/Kg/day, or less than 50 nmol/Kg/day).

In certain embodiments, for any of the aforementioned methods of treating a subject, the dose is less than 100 nmol/Kg/day (e.g., less than 90 nmol/Kg/day, less than 80 nmol/Kg/day, less than 70 nmol/Kg/day, less than 60 nmol/Kg/day, less than 50 nmol/Kg/day, less than 40 nmol/Kg/day, less than 30 nmol/Kg/day, less than 20 nmol/Kg/day, or less than 10 nmol/Kg/day).

In some embodiments, for any of the aforementioned methods of treating a subject, the frequency of administration is no more than three times a day (e.g., once every 8 hours, once every 12 hours, or once every 24 hours).

In some embodiments, for any of the aforementioned methods of treating a subject, the administration occurs only during daylight hours of between 6:00 and 18:00 at a frequency of once every 4 to 6 hours, and the administration does not occur at night between 18:00 and 6:00.

In some embodiments, for any of the aforementioned methods of treating a subject, the methods can further include administrating a V2 antagonist/inhibitor. The V2 antagonist can be administered between 1 to 8 hours (preferably within 1 to 3 hours), before or after (preferably before) administration of the V1a partial agonist. In some embodiments, the V2 antagonist includes, for example, mozavaptan, tolvaptan, tolvaptan phosphate ester, satavaptan, lixivaptan, conivaptan, RWJ-351647, VP-343, VP-393, [PmP1, D-Ile2, Ile4, Arg8, Ala9] vasopressin, [PmP1, D-Ile2, Ile4, Arg8] vasopressin, and/or [PmP1, D-Ile2, Ile4, Arg8, Ala9] vasopressin-(1-8)-OH. The V1a partial agonist can be administrated at a dose of from 1 nmol/Kg to 250 nmol/Kg (e.g., from 1 nmol/Kg to 150 nmol/Kg, or from 1 nmol/Kg to 75 nmol/Kg). In certain embodiments, when the V2 antagonist is tolvaptan, the tolvaptan is administrated parenterally at a dose of from 1 µg/kg to 300 µg/kg (e.g., from 1 µg/kg to 200 µg/kg, or from 1 µg/kg to 100 µg/kg).

In some embodiments, for any of the aforementioned methods of treating a subject, the subject suffers from ascites (e.g., refractory ascites).

In some embodiments, the present disclosure provides a method of treating a subject having liver fibrosis, cirrhosis, portal hypertension, ascites, esophageal varices, fundal varices, bleeding, mean arterial pressure less than 95 mmHg, hepatorenal syndrome, or any combination thereof, or wherein the subject has liver fibrosis; or wherein the subject has cirrhosis; or wherein the subject has portal hypertension; or wherein the subject has esophageal varices; or wherein the subject has fundal varices; or wherein the subject has bleeding varices; or wherein the subject has cirrhosis with mean arterial pressure less than 95 mm Hg; or wherein the subject has hepatorenal syndrome; the method includes step (i) or step (ii) below, administered within 1 to 8 hours (e.g., preferably within 1 to 3 hours), before or after (e.g., preferably after), administration of a therapeutically effective dose of V2 antagonist, wherein:

step (i) comprises administering to the subject a therapeutically effective dose of a pharmaceutical composition including a peptide of Formula (III)

(III)
[SEQ ID NO. 7]
[(U)$_c$-Cys-Tyr-Phe-Gln-Asn-Cys-Pro-Lys-Gly-NH$_2$]

or a pharmaceutically effective salt thereof, wherein the 2 Cys residues are covalently connected with a disulfide bond, U is an amino acid residue and at each occurrence, is independently selected from Gly, L-Ala, D-Ala, L-Lys, D-Lys, L-Orn, D-Orn, L-Glu, D-Glu, L-Asp, and D-Asp, and c is a number of amino acid residue(s) U and is an integer of from 0 to 10;

step (ii) comprises administering to the subject a therapeutically effective dose of a pharmaceutical composition including a peptide of Formula (IV)

(IV)
[SEQ ID NO. 4]
[Mpa-Tyr-Phe-Gln-Asn-Cys-Pro-Lys(Z)$_d$-Gly-NH$_2$]

or a pharmaceutically effective salt thereof, wherein the Mpa and Cys residues are covalently connected with a disulfide bond, Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and d is a number of amino acid residue(s) Z and is an integer from 0 to 5.

In some embodiments, when the V2 antagonist is administered, the V2 antagonist is mozavaptan, tolvaptan, tolvaptan phosphate ester, satavaptan, lixivaptan, conivaptan, RWJ-351647, VP-343, VP-393, [PmP1, D-Ile2, Ile4, Arg8, Ala9] vasopressin, [PmP1, D-Ile2, Ile4, Arg8] vasopressin, and/or [PmP1, D-Ile2, Ile4, Arg8, Ala9] vasopressin-(1-8)-OH.

In some embodiments, the V2 antagonist is tolvaptan. The tolvaptan can be administered at a dose from 1 to 300 µg/Kg (e.g., from 1 µg/Kg to 200 µg/Kg, or from 1 µg/Kg to 100 µg/Kg).

Embodiments of peptides of Formula (III) are as discussed above. For example, in some embodiments, for the peptide of Formula (III), c is not 0. In some embodiments, one or both of the termini of the peptide of Formula (III) do not include an alkyl group (e.g., an alkyl group having 3 to 36 carbon units). In some embodiments, one or both of the termini of the peptide of Formula (III) do not include an alkyl group having 3 to 36 carbon units, nitrilotriacetic acid, imido diacetic acid, or one or more histidine residue. In some embodiments, the peptide of Formula (III) does not include a peptide where U is Gly and/or His, and c is an integer from 1-6, the peptide optionally including a terminal alkyl group. In some embodiments, (U)$_c$ in the peptide of formula (III) does not include Leu, Phe, Tyr, Trp, Pro, Gly-Gly, Leu-Leu, Gly-Pro, sarcosyl-Gly, and/or Gly-Gly-Gly.

In some embodiments, the method of treating a subject with liver fibrosis, cirrhosis, portal hypertension, ascites, esophageal varices, fundal varices, bleeding, mean arterial pressure less than 95 mm Hg, hepatorenal syndrome, or any combination thereof, includes administering a therapeutically effective dose of a pharmaceutical composition including a V1a agonist administered within 1 to 8 hours (e.g., preferably within 1 to 3 hours), either before or after (e.g., preferably after) administration of a therapeutically effective dose of V2 antagonist, wherein the V1a agonist includes a peptide of Formula (IV):

(IV)
[SEQ ID NO. 4]
[Mpa-Tyr-Phe-Gln-Asn-Cys-Pro-Lys(Z)$_d$-Gly-NH$_2$]

or a pharmaceutically effective salt thereof, wherein the Mpa and Cys residues are covalently connected with a disulfide bond, Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and d is a number of amino acid residue(s) Z and is an integer from 0 to 5; and wherein the V2 antagonist is mozavaptan, tolvaptan, tolvaptan phosphate ester, satavaptan, lixivaptan, conivaptan, RWJ-351647, VP-343, VP-393, [PmP1, D-Ile2, Ile4, Arg8, Ala9] vasopressin, [PmP1, D-Ile2, Ile4, Arg8] vasopressin, and/or [PmP1, D-Ile2, Ile4, Arg8, Ala9] vasopressin-(1-8)-OH.

In some embodiments, a method of treating a subject with liver fibrosis, cirrhosis, portal hypertension, ascites, esophageal varices, fundal varices, bleeding, mean arterial pressure less than 95 mm Hg, hepatorenal syndrome, or any combination thereof, includes administering a therapeutically effective dose of a pharmaceutical composition including a V1a agonist and followed 2 to 8 hours later by administration of a therapeutically effective dose of V2 antagonist, wherein the V1a agonist includes a peptide of Formula (III):

(III)
[SEQ ID NO. 7]
[(U)$_c$-Cys-Tyr-Phe-Gln-Asn-Cys-Pro-Lys-Gly-NH$_2$]

or a pharmaceutically effective salt thereof, wherein the 2 Cys residues are covalently connected with a disulfide bond, U is an amino acid residue and at each occurrence, is independently selected from Gly, L-Ala, D-Ala, L-Lys, D-Lys, L-Orn, D-Orn, L-Glu, D-Glu, L-Asp, and D-Asp, and c is a number of amino acid residue(s) U and is an integer of from 0 to 10; and wherein the V2 antagonist is mozavaptan, tolvaptan, tolvaptan phosphate ester, satavaptan, lixivaptan, conivaptan, RWJ-351647, VP-343, VP-393, [PmP1, D-Ile2, Ile4, Arg8, Ala9] vasopressin, [PmP1, D-Ile2, Ile4, Arg8] vasopressin, and/or [PmP1, D-Ile2, Ile4, Arg8, Ala9] vasopressin-(1-8)-OH.

In some embodiments, the method of treating a subject with liver fibrosis, cirrhosis, portal hypertension, ascites, esophageal varices, fundal varices, bleeding, mean arterial pressure less than 95 mm Hg, hepatorenal syndrome, or any combination thereof, includes administering a therapeutically effective dose of a pharmaceutical composition including a V1a agonist and followed 2 to 8 hours later by a parenteral administration of tolvaptan at a dose from 1 to 300 µg/Kg (e.g., from 1 µg/Kg to 200 µg/Kg, or from 1 µg/Kg to 100 µg/Kg), wherein the V1a agonist includes a peptide of Formula (IV):

(IV)
[SEQ ID NO. 4]
[Mpa-Tyr-Phe-Gln-Asn-Cys-Pro-Lys(Z)$_d$-Gly-NH$_2$]

or a pharmaceutically effective salt thereof, wherein the Mpa and Cys residues are covalently connected with a disulfide bond, Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and d is a number of amino acid residue(s) Z and is an integer from 0 to 5.

In some embodiments, the present disclosure provides a method of treating a subject with liver fibrosis, cirrhosis, portal hypertension, ascites, esophageal varices, fundal varices, bleeding, mean arterial pressure less than 95 mm Hg, hepatorenal syndrome, or any combination thereof, includes administering a therapeutically effective dose of a pharmaceutical composition including a V1a agonist and followed 2 to 8 hours later by a parenteral administration of tolvaptan at a dose from 1 to 300 µg/Kg (e.g., from 1 µg/Kg to 200 µg/Kg, or from 1 µg/Kg to 100 µg/Kg), wherein the V1a agonist includes a peptide of Formula (III):

(III)
[SEQ ID NO. 7]
[(U)$_c$-Cys-Tyr-Phe-Gln-Asn-Cys-Pro-Lys-Gly-NH$_2$]

or a pharmaceutically effective salt thereof, wherein the 2 Cys residues are covalently connected with a disulfide bond, U is an amino acid residue and at each occurrence, is independently selected from Gly, L-Ala, D-Ala, L-Lys, D-Lys, L-Orn, D-Orn, L-Glu, D-Glu, L-Asp, and D-Asp, and c is a number of amino acid residue(s) U and is an integer of from 0 to 10.

In any of the aforementioned methods, the administration can be oral and/or parenteral. In certain embodiments, the administration is parenteral administration, such as subcutaneous or intravenous administration. In certain embodiments, the parenteral administration is subcutaneous administration.

EXAMPLES

Example 1: Peptide Synthesis for Peptides of Formula (I)

Formula (I) peptides were synthesized by solid phase peptide synthesis (SPPS) with Rink Amide Resin—ProTide (0.59 mmol/g) as the starting solid support (CEM, Matthews, NC) in an Automated Microwave Peptide Synthesizer (LibertyBlue HT12, CEM, Matthews, NC). Fmoc protected amino acids were used including Fmoc-Gly-OH (Combi-Blocks, San Diego, CA), Fmoc-Lys(dde)-OH (Combi-Blocks, San Diego, CA), Fmoc-Pro-OH (Combi-Blocks, San Diego, CA), Fmoc-Cys(Mmt)-OH, Fmoc-Asn (Trt)-OH (Combi-Blocks, San Diego, CA), Fmoc-HomoGln (Trt)-OH (BLDPharm, Shanghai, China), Fmoc-Phe-OH (Combi-Blocks, San Diego, CA), Fmoc-Tyr(tBu)-OH (Combi-Blocks, San Diego, CA), Fmoc-12-Ado-OH (Combi-Blocks, San Diego, CA), MPA(Mmt)-OH (GL Biochem, Shanghai, China), Fmoc-L-Dab(Dde)-OH (BLDPharm, Shanghai, China), Fmoc-D-Dab(Dde)-OH (BLDPharm, Shanghai, China), Fmoc-L-Dap(Dde)-OH (BLDPharm, Shanghai, China), Fmoc-D-Dap(Dde)-OH (BLDPharm, Shanghai, China), Fmoc-L-Orn(Dde)-OH (BLDPharm, Shanghai, China), Fmoc-D-Orn(Dde)-OH (BLDPharm, Shanghai, China), Fmoc-D-Lys(Dde)-OH (BLDPharm, Shanghai, China), Fmoc-L-Ala-OH (BLDPharm, Shanghai, China), Fmoc-D-Ala-OH (BLDPharm, Shanghai, China), Fmoc-L-Glu(OtBu)-OH (BLDPharm, Shanghai, China), Fmoc-D-Glu(OtBu)-OH (BLDPharm, Shanghai, China), Fmoc-L-Asp(OtBu)-OH (BLDPharm, Shanghai, China), Fmoc-D-Asp(OtBu)-OH (BLDPharm, Shanghai, China), Fmoc-L-Lys(Boc)-OH (BLDPharm, Shanghai, China), Fmoc-D-Lys(Boc)-OH (BLDPharm, Shanghai, China), Fmoc-L-Orn(Boc)-OH (BLDPharm, Shanghai, China), Fmoc-D-Orn(Boc)-OH (BLDPharm, Shanghai, China), and Fmoc-Gly-Gly-OH (BLDPharm, Shanghai, China). Each amino acid was anchored sequentially onto the peptide resin using Fmoc chemistry, so that the linear protected peptide on resin was achieved. Next, the Dde-protected side chain of Lys (or B) was selectively deprotected in 2% hydrazine in DMF, followed by Fmoc chemistry again, leading to the protected branched peptide on resin. Then, the Mmt-protected side chains of cysteine and 3-mercaptopropionic acid were selectively deprotected in 2% TFA in DCM, followed by on resin disulfide bond formation using N-chlorosuccinimide. The cyclized crude peptide was obtained by acidolysis with trifluoroacetic acid in the presence of carbocation scavengers and ether precipitation. Finally, the peptide was purified and characterized by reversed phase HPLC (1260 Infinity II Preparative LC Systems, Santa Clara, CA) using the following method:

TABLE 1

| Preparative HPLC parameters Method: Preparative HPLC | |
|---|---|
| Parameter | Value |
| Injection Volume | 4.5 mL |
| Flow Rate | 35.0 mL/min |
| Mobile Phase A | Acetonitrile (can), 0.1% trifluoroacetic acid (TFA) |
| Mobile Phase B | 10% ACN, 0.1% TFA in water |
| Column | Waters XBridge, Prep C18 5 µm OBD, 30 × 150 mm, P/N 186003284 |
| Guard Column Holder | 30 mm Prep Guard Holder, P/N 186006912 |
| Guard Column | Waters XBridge, Prep C18 5 µm, 30 × 10 mm guard cartridge, P/N 186006893 |
| Column Temperature | Ambient temperature |
| Detection | 280 nm |
| Run Time | 19 minutes |

TABLE 1-continued

Gradient

| Time (minutes) | % A | % B |
| --- | --- | --- |
| 0.0 | 0 | 100 |
| 1.0 | 0 | 100 |
| 12.8 | 22 | 78 |
| 13.1 | 89 | 11 |
| 15.5 | 89 | 11 |
| 15.6 | 0 | 100 |
| 19.0 | 0 | 100 |

Then the fractions were collected and lyophilized as a white powder. The mass of the peptide was determined using Agilent LCMS system (6100 Series Single Quadrupole LC/MS, Santa Clara, CA) by the following gradient conditions:

TABLE 2A

Analytical HPLC/MS parameters.
Method: Analytical HPLC/MS

| | |
| --- | --- |
| Injection Volume | Variable |
| Flow Rate | 1.0 mL/min |
| Mobile Phase A | Water, 0.5% acetic acid |
| Mobile Phase B | ACN, 0.5% acetic acid |
| Column | Waters XBridge, Prep C18 5 µm OBD, 4.6 × 100 mm, P/N 186003115 |
| Guard Column | Waters XBridge C18 VanGuard Cartridge, 130Å, 5 µm, 3.9 mm × 5 mm, P/N 186007771 |
| Column Temperature | Ambient temperature |
| Detection | 220 nm |
| Run Time | 11 minutes |

Gradient

| Time (minutes) | % A | % B |
| --- | --- | --- |
| 0.0 | 90 | 10 |
| 1.0 | 90 | 10 |
| 6.0 | 40 | 60 |
| 6.5 | 10 | 90 |
| 8.0 | 10 | 90 |
| 8.5 | 90 | 10 |
| 11.0 | 90 | 10 |

LC-MS

| Parameter | Value |
| --- | --- |
| Mode | Positive |
| Ion Source | API-ES |
| Capillary Voltage | 4000 V |
| Mass Range | 100 to 2000 D |
| Fragmentor | 80 |
| Gain | 1.00 |
| Speed | 2600 µL/sec |

TABLE 2B

Additional analytical HPLC/MS parameters.
Method: Analytical HPLC

| | |
| --- | --- |
| Injection Volume | 5 µL |
| Flow Rate | 0.5 mL/min |
| Mobile Phase A | Water, 0.1% trifluoroacetic acid |
| Mobile Phase B | ACN, 0.1% trifluoroacetic acid |
| Column | Waters XSelect Peptide CSH C18, 130Å, 3.5 µm, 2.1 mm × 150 mm, P/N 186006952 |
| Column Temperature | 60° C. |
| Detection | 220 nm |
| Run Time | 52 minutes |

Gradient

| Time (minutes) | % A | % B |
| --- | --- | --- |
| 0.0 | 95 | 5 |
| 5.0 | 95 | 5 |
| 35.0 | 70 | 30 |
| 45.5 | 10 | 90 |
| 46.0 | 10 | 90 |
| 46.1 | 95 | 5 |
| 52.0 | 95 | 5 |

A peptide having the sequence [Mpa-Tyr-Phe-Hgn-Asn-Cys-Pro-B(X)$_a$-Gly [SEQ ID NO. 8]; having a disulfide bond between Mpa and Cys] with TFA salt; wherein B is Lys, X is a Gly residue, and a is 1 was synthesized and purified using the general method described in the present Example. HPLC analysis of this peptide shows a retention time of 21.615 mins and a purity was 92%. The empirical formula was $C_{49}H_{69}N_{13}O_{13}S_2$ and the theoretical monoisotopic weight was 1111.5. The mass found in the LCMS was [M+H]$^+$ was 1112.5 using the method described herein.

A peptide having the sequence [Mpa-Tyr-Phe-Hgn-Asn-Cys-Pro-B(X)$_a$-Gly [SEQ ID NO. 9]; having a disulfide bond between Mpa and Cys] with TFA salt; wherein B is Lys, wherein X is Gly, and a is 2 was synthesized and purified using the general method described in the present Example. HPLC analysis of this peptide shows a peak having a retention time of 21.515 mins and at 94% purity. The empirical formula was $C_{51}H_{72}N_{14}O_{14}S_2$ and the theoretical monoisotopic weight was 1168.5. The mass found in the LCMS [M+H]$^+$ was 1169.5 using the method described herein.

A peptide having the sequence [Mpa-Tyr-Phe-Hgn-Asn-Cys-Pro-B(X)$_a$-Gly [SEQ ID NO. 10]; with disulfide bond between Mpa and Cys] with TFA salt; wherein B is Lys, X is Gly, and a is 3 was synthesized and purified using the general method described in the present Example. The HPLC analysis of this peptide shows a peak having a retention time of 21.355 mins and at 95% purity. The empirical formula was $C_{53}H_{75}N_{15}O_{15}S_2$ and the theoretical monoisotopic weight was 1226.4. The mass found in the LCMS [M+H]$^+$ was 1227.5 using the method described herein.

A peptide having the sequence [Mpa-Tyr-Phe-Hgn-Asn-Cys-Pro-B(X)$_a$-Gly [SEQ ID NO. 11]; with disulfide bond between Mpa and Cys] with TFA salt; wherein B is Lys, X is Gly, and a is 4 was synthesized and purified using the general method described in the present Example. The HPLC analysis of this peptide shows a retention time of 21.281 mins and at 91% purity. The empirical formula was $C_{55}H_{78}N_{16}O_{16}S_2$ and the theoretical monoisotopic weight was 1282.5. The mass found in the LCMS [M+H]$^+$ was 1283.5 using the method described herein.

A peptide having the sequence [Mpa-Tyr-Phe-Hgn-Asn-Cys-Pro-B(X)$_a$-Gly [SEQ ID NO. 12]; with disulfide bond between Mpa and Cys] with TFA salt; wherein B is Lys, X is Gly, and a is 5 was synthesized and purified using the general method described in the present Example. The HPLC analysis of the above peptide shows a retention time of 20.959 mins and at 93% purity. The empirical formula was $C_{57}H_{81}N_{17}O_{17}S_2$ and the theoretical monoisotopic weight was 1339.5. The mass found in the LCMS [M+H]$^+$ was 1340.5 using the method described herein.

A peptide having the sequence [Mpa-Tyr-Phe-Hgn-Asn-Cys-Pro-B(X)$_a$-Gly [SEQ ID NO. 13]; with disulfide bond between Mpa and Cys] with TFA salt; wherein B is Lys, X is Gly, and a is 6 was synthesized and purified using the general method described in the present Example. The HPLC analysis of the above peptide shows a retention time of 20.73 mins and at 90% purity. The empirical formula was $C_{59}H_{84}N_{18}O_{18}S_2$ and the theoretical monoisotopic weight was 1396.5. The mass found in the LCMS: $[M+H]^+=1397.5$ using method described herein.

A peptide having the sequence [Mpa-Tyr-Phe-Hgn-Asn-Cys-Pro-B(X)$_a$-Gly [SEQ ID NO. 14]; with disulfide bond between Mpa and Cys] with TFA salt; wherein B is Lys, X is Gly, and a is 7 was synthesized and purified using the general method described in the present Example. This HPLC analysis of the above peptide shows a retention time of 20.988 mins and at 89% purity. The empirical formula was $C_{61}H_{87}N_{19}O_{19}S_2$ and the theoretical monoisotopic weight was 1453.5. The mass found in the LCMS $[M+H]^+$ was 1454.5 using the method described herein.

A peptide having the sequence [Mpa-Tyr-Phe-Hgn-Asn-Cys-Pro-B(X)$_a$-Gly [SEQ ID NO. 15]; with disulfide bond between Mpa and Cys] with TFA salt; wherein B is Lys, X is Gly, and a is 8 was synthesized and purified using the general method described in the present Example. The HPLC analysis of the above peptide shows a retention time of 20.836 mins and at 87% purity. The empirical formula was $C_{63}H_{90}N_{20}O_{20}S_2$ and the theoretical monoisotopic weight was 1510.6. The mass found in the LCMS $[M+H]^+$ was 1511.6 using the method described herein.

A peptide having the sequence [Mpa-Tyr-Phe-Hgn-Asn-Cys-Pro-B(X)$_a$-Gly [SEQ ID NO. 16]; with disulfide bond between Mpa and Cys] with TFA salt; wherein B is Lys, X is Gly, and "a" is 9 was synthesized and purified using the general method described in the present Example. The HPLC analysis of the above peptide shows a retention time of 20.729 mins and at 86% purity. The empirical formula was $C_{65}H_{93}N_{21}O_{21}S_2$ and theoretical monoisotopic weight was 1567.6. The mass found in the LCMS $[M+H]^+$ was 1568.6 using the method described herein.

A peptide having the sequence [Mpa-Tyr-Phe-Hgn-Asn-Cys-Pro-B(X)$_a$-Gly [SEQ ID NO. 17]; with disulfide bond between Mpa and Cys] with TFA salt; wherein B is Dap; wherein "a" is 0 was synthesized and purified using the general method described in the present Example. The HPLC analysis of the above peptide shows a retention time of 20.981 mins and at 86% purity. The empirical formula was $C_{44}H_{60}N_{12}O_{12}S_2$ and the theoretical monoisotopic weight was 1012.4. The mass found in the LCMS $[M+H]^+$ was 1013.4 using the method described herein.

A peptide having the sequence [Mpa-Tyr-Phe-Hgn-Asn-Cys-Pro-B(X)$_a$-Gly [SEQ ID NO. 18]; with disulfide bond between Mpa and Cys] with TFA salt; wherein B is d-Lys; wherein "a" is 0 was synthesized and purified using the general method described in the present Example. The HPLC analysis of the above peptide shows a retention time of 21.382 mins and at 91% purity. The empirical formula was $C_{47}H_{66}N_{12}O_{12}S_2$ and the theoretical monoisotopic weight was 1054.4. The mass found in the LCMS $[M+H]^+$ was 1055.5 using the method described herein.

A peptide having the sequence [Mpa-Tyr-Phe-Hgn-Asn-Cys-Pro-B(X)$_a$-Gly [SEQ ID NO. 19]; with disulfide bond between Mpa and Cys] with TFA salt; wherein B is Lys; wherein "(X)" is 12-aminododecanoic acid, and "a" is 1 was synthesized and purified using the general method described in the present Example. The HPLC analysis of the above peptide shows a retention time of 31.354 mins and at 91% purity. The empirical formula was $C_{59}H_{89}N_{13}O_{13}S_2$ and the theoretical monoisotopic weight was 1251.6. The mass found in the LCMS $[M+H]^+$ was 1252.5 using the method described herein.

Example 2: Peptide Synthesis for Peptides of Formula (II) and (IV)

Formula (II) and Formula (IV) peptides were synthesized by solid phase peptide synthesis (SPPS) with Rink Amide Resin—ProTide (0.59 mmol/g) as the starting solid support (CEM, Matthews, NC) in Automated Microwave Peptide Synthesizer (LibertyBlue HT12, CEM, Matthews, NC). Fmoc protected amino acids were used including Fmoc-Gly-OH (Combi-Blocks, San Diego, CA), Fmoc-Lys(dde)-OH (Combi-Blocks, San Diego, CA), Fmoc-Pro-OH (Combi-Blocks, San Diego, CA), Fmoc-Cys(Mmt)-OH (Combi-Blocks, San Diego, CA), Fmoc-Asn(Trt)-OH, (Combi-Blocks, San Diego, CA) Fmoc-Gln(Trt)-OH (Combi-Blocks, San Diego, CA), Fmoc-Phe-OH (Combi-Blocks, San Diego, CA), Fmoc-Tyr(tBu)-OH (Combi-Blocks, San Diego, CA), MPA(Mmt)-OH (GL Biochem, Shanghai, China), Fmoc-Gly-Gly-OH (BLDPharm, Shanghai, China), Fmoc-L-Orn(Dde)-OH (BLDPharm, Shanghai, China), Fmoc-D-Orn(Dde)-OH (BLDPharm, Shanghai, China), Fmoc-D-Lys(Dde)-OH (BLDPharm, Shanghai, China), Fmoc-L-Ala-OH (BLDPharm, Shanghai, China), Fmoc-D-Ala-OH (BLDPharm, Shanghai, China), Fmoc-L-Glu (OtBu)-OH (BLDPharm, Shanghai, China), Fmoc-D-Glu (OtBu)-OH (BLDPharm, Shanghai, China), Fmoc-L-Asp (OtBu)-OH (BLDPharm, Shanghai, China), Fmoc-D-Asp (OtBu)-OH (BLDPharm, Shanghai, China), Fmoc-L-Lys (Boc)-OH (BLDPharm, Shanghai, China), Fmoc-D-Lys (Boc)-OH (BLDPharm, Shanghai, China), Fmoc-L-Orn (Boc)-OH (BLDPharm, Shanghai, China), and Fmoc-D-Orn (Boc)-OH (BLDPharm, Shanghai, China). Each amino acid was anchored sequentially onto the peptide resin using Fmoc chemistry, so that the linear protected peptide on resin was achieved. Next, the side chain of Lys was selectively deprotected in 2% hydrazine in DMF, followed by Fmoc chemistry again, leading to the protected branched peptide on resin. Then, the side chains of cysteine and 3-mercaptopropionic acid were selectively deprotected in 2% TFA in DCM, followed by on resin disulfide bond formation using N-chlorosuccinimide. The cyclized crude peptide was obtained by acidolysis with trifluoroacetic acid in the presence of carbocation scavengers and ether precipitation. Finally, the peptide was purified and characterized by reversed phase HPLC using the method in example 1 and then lyophilized as white powder. The mass of the peptide was determined by Agilent LCMS system using the same LCMS method in Example 1.

A peptide having the sequence [Mpa-Tyr-Phe-Gln-Asn-Cys-Pro-Lys(X)$_a$-Gly [SEQ ID NO. 20]; with disulfide bond between Mpa and Cys] with TFA salt; wherein X is Gly and a is 6 was synthesized and purified using the general method described in the present Example. The HPLC analysis of this peptide shows a retention time of 20.624 mins and at 96% purity. The empirical formula was $C_{58}H_{82}N_{18}O_{18}S_2$ and the theoretical monoisotopic weight was 1382.5. The mass found in the LCMS $[M+H]^+$ was 1383.5 using method described in Example 1.

A peptide having the sequence [Mpa-Tyr-Phe-Gln-Asn-Cys-Pro-Lys(X)$_a$-Gly [SEQ ID NO. 21]; with disulfide bond between Mpa and Cys] with TFA salt; wherein X is Gly and a is 7 was synthesized and purified using the general method described in the present Example. The HPLC analysis of the above peptide shows a retention time of 20.495 mins and at 95% purity. The empirical formula was $C_{60}H_{85}N_{19}O_{19}S_2$ and the theoretical monoisotopic weight was 1439.6. The mass found in the LCMS: [M+H]$^+$ was 1440.5 using method described in Example 1.

A peptide having the sequence [Mpa-Tyr-Phe-Gln-Asn-Cys-Pro-Lys(X)$_a$-Gly [SEQ ID NO. 22]; with disulfide bond between Mpa and Cys] with TFA salt; wherein X is Gly and a is 8 was synthesized and purified using the general method described in the present Example. The HPLC analysis of the above peptide shows the retention time of 21.121 mins and at 90% purity. The empirical formula was $C_{62}H_{88}N_{20}O_{20}S_2$ and the theoretical monoisotopic weight was 1496.6. The mass found in the LCMS [M+H]$^+$ was 1497.6 using the method described in Example 1.

The peptide having the sequence [Mpa-Tyr-Phe-Gln-Asn-Cys-Pro-Lys(X)$_a$-Gly [SEQ ID NO. 23]; with disulfide bond between Mpa and Cys] with TFA salt; wherein X is Gly and a is 9 was synthesized and purified using the general method described in the present Example. The HPLC analysis of the above peptide shows the retention time of 20.409 mins and at 93% purity. The empirical formula was $C_{64}H_{91}N_{21}O_{21}S_2$ and the theoretical monoisotopic weight was 1553.6. The mass found in the LCMS [M+H]$^+$ was 1554.6 using the method described in Example 1.

Example 3: Formula (I) Peptides where $(X)_A$ is $(Gly)_{0-9}$—Partial Agonists

Figure 2:
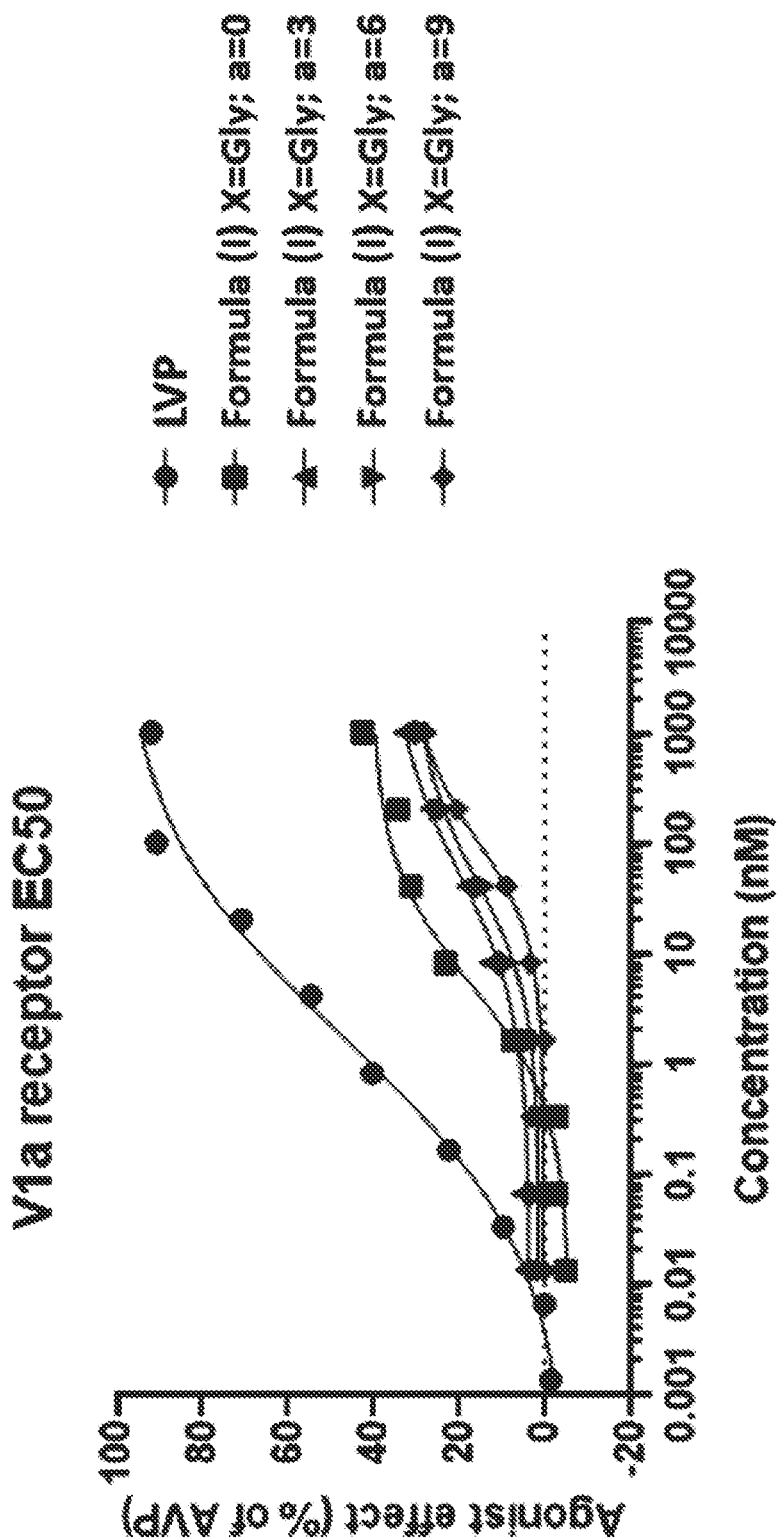
FIG. 2 is a graph showing the results of EC50 determination of a Formula (I) peptides [Mpa-Tyr-Phe-Hgn-Asn-Cys-Pro-Lys(X)$_a$-Gly [SEQ ID NO. 5]; with disulfide bond between Mpa and Cys] for V1a receptor. A Formula (I) peptide where "(X)$_a$" has X=Gly and a=0, 3, 6, or 9 has EC50 of 5.2, 53.5, 45.9, or 104.8 nM for V1a receptor (n=2). It is a partial V1a agonist, with 42.8, 32.9, 28.2, or 28.1% highest agonist effect compared with arginine vasopressin (AVP) which is the 100% control (n=2).

Peptides of Formula (I) include Mpa-Tyr-Phe-Hgn-Asn-Cys-Pro-Lys(X)$_a$-Gly-NH$_2$ [SEQ ID NO. 24]; where $(X)_a$ is a peptide with "a" residues and each residue X is independently selected from Gly, and a D- or L-amino acid version of Ala, Lys, Orn, Glu, and Asp, where "a" is 0-10. V1a Human Vasopressin GPCR Cell Based Agonist Calcium Flux Assay were conducted at Eurofins Cerep SA (France) on a fee for service basis. Human recombinant CHO cells expressing human V1 receptors were distributed in microplates. Intracellular calcium signal was detected by fluorimetry, and the signal was acquired before and after addition of a known agonist concentration. The following agonist concentrations were tested (nM); 0.0128, 0.064, 0.32, 1.6, 8, 40, 200, and 1,000. The results are expressed as a percent of 1,000 nM of AVP agonist response. All assays were performed in duplicate. Changes in fluorescence intensity reflected changes in the concentration of free cytosolic calcium. The standard reference agonist was AVP, and the maximum activity of the other agonist are expressed as percent of maximum AVP activity. The half-maximal effective concentration (EC50) was determined by a non-linear regression analysis of the concentration-response curves generated with mean replicate values using Hill equation curve fitting (Cerep, l'Evescault, France). FIG. 2 shows an example a graphical data and a summary of representative species of Formula (I), also summarized in Table 3. All the species are partial agonists.

TABLE 3

Peptide properties (Formula (I) peptides were partial agonists)

| Peptides (all with intramolecular disulfide bond) | Estimated V1a EC50 (nM); n = 2 | V1a Highest agonist effect (% of AVP); n = 2 |
| --- | --- | --- |
| Arginine Vasopressin (AVP) | 0.42 | 100 |
| Lysine vasopressin (LVP) | 1.65 | 92.1 |
| Mpa-Tyr-Phe-Hgn-Asn-Cys-Pro-Lys-Gly-NH2 [SEQ ID NO. 25] | 5.2 | 42.8 |
| Mpa-Tyr-Phe-Hgn-Asn-Cys-Pro-Lys(X)-Gly-NH2; X = Gly [SEQ ID NO. 8] | 25.3 | 40.3 |
| Mpa-Tyr-Phe-Hgn-Asn-Cys-Pro-Lys(X)$_a$-Gly-NH2; $(X)_a$ = (Gly)$_2$ [SEQ ID NO. 9] | 38.2 | 37.0 |
| Mpa-Tyr-Phe-Hgn-Asn-Cys-Pro-Lys(X)$_a$-Gly-NH2; $(X)_a$ = (Gly)$_3$ [SEQ ID NO. 10] | 53.5 | 32.9 |
| Mpa-Tyr-Phe-Hgn-Asn-Cys-Pro-Lys(X)$_a$-Gly-NH2; $(X)_a$ = (Gly)$_4$ [SEQ ID NO. 11] | 160.8 | 33.6 |
| Mpa-Tyr-Phe-Hgn-Asn-Cys-Pro-Lys(X)$_a$-Gly-NH2; $(X)_a$ = (Gly)$_5$ [SEQ ID NO. 12] | 50.1 | 29.6 |
| Mpa-Tyr-Phe-Hgn-Asn-Cys-Pro-Lys(X)$_a$-Gly-NH2; $(X)_a$ = (Gly)$_6$ [SEQ ID NO. 13] | 45.9 | 28.2 |
| Mpa-Tyr-Phe-Hgn-Asn-Cys-Pro-Lys(X)$_a$-Gly-NH2; $(X)_a$ = (Gly)$_7$ [SEQ ID NO. 14] | 30.9 | 26.1 |
| Mpa-Tyr-Phe-Hgn-Asn-Cys-Pro-Lys(X)$_a$-Gly-NH2; $(X)_a$ = (Gly)$_8$ [SEQ ID NO. 15] | 225.7 | 24.8 |
| Mpa-Tyr-Phe-Hgn-Asn-Cys-Pro-Lys(X)$_a$-Gly-NH2; $(X)_a$ = (Gly)$_9$ [SEQ ID NO. 16] | 104.8 | 28.1 |
| Mpa-Tyr-Phe-Hgn-Asn-Cys-Pro-Lys(X)$_a$-Gly-NH2; $(X)_a$ = (Gly)$_9$-Ac [SEQ ID NO. 26] | low potency >>10 µM* | 40 |

TABLE 3-continued

Peptide properties (Formula (I) peptides were partial agonists)

| Peptides (all with intramolecular disulfide bond) | Estimated V1a EC50 (nM); n = 2 | V1a Highest agonist effect (% of AVP); n = 2 |
|---|---|---|
| Mpa-Tyr-Phe-Hgn-Asn-Cys-Pro-Lys(X)$_a$-Gly-NH2; (X)$_a$ = Lauric acid [SEQ ID NO. 27] | low potency >>10 µM | inactive |
| Mpa-Tyr-Phe-Hgn-Asn-Cys-Pro-Lys(X)$_a$-Gly-NH2; (X)$_a$ = Ac [SEQ ID NO. 28] | low potency >>10 µM* | 30 |
| Mpa-Tyr-Phe-Hgn-Asn-Cys-Pro-Lys(X)$_a$-Gly-NH2; (X)$_a$ = Dap [SEQ ID NO. 29] | 1.34 µM | 7.5 |
| Mpa-Tyr-Phe-Hgn-Asn-Cys-Pro-Dap-Gly-NH2 [SEQ ID NO. 17] | low potency >>10 µM* | 3.5 (inactive in vitro) |
| Mpa-Tyr-Phe-Hgn-Asn-Cys-Pro-dLys-Gly-NH2 (note: dLys = D-Lys) [SEQ ID NO. 18] | low potency >>10 µM* | 0.20 (inactive in vitro) |
| Mpa-Tyr-Phe-Hgn-Asn-Cys-Pro-Lys(12-aminododecanoic acid)-Gly-NH2 [SEQ ID NO. 19] | low potency >>10 µM* | 2.5 (inactive in vitro) |

*Any activity below 5% at saturating concentration (i.e., >100 nM) is considered inactive in vitro but may get activated in vivo (i.e., essentially as a Pro-drug).

Example 4: Formula (II) Peptides, when (X)$_A$ is (Gly)$_6$ or (Gly)$_9$: A Partial Agonist (Table 4)

Figure 3:
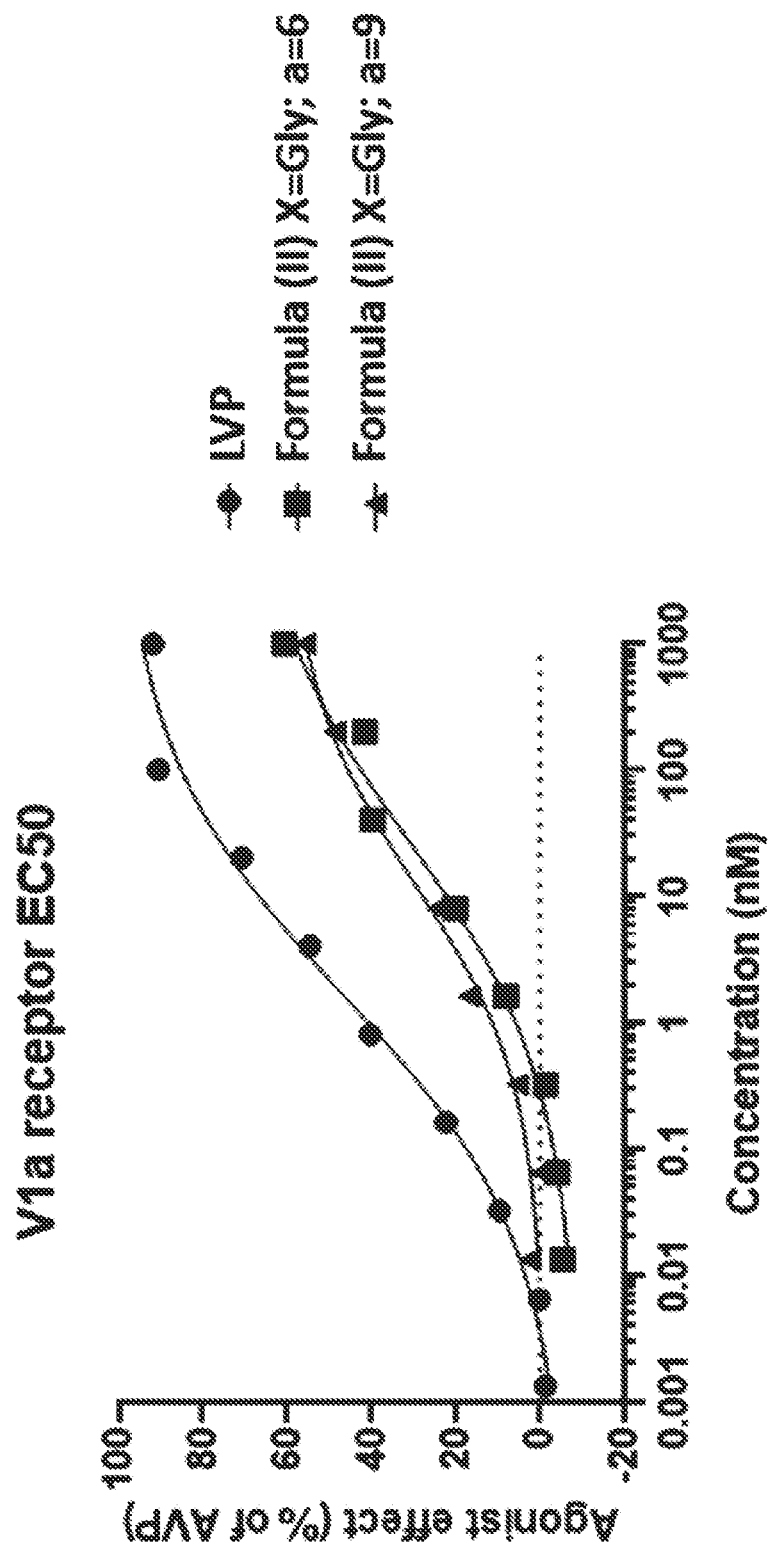
FIG. 3 is a graph of the EC50 of Formula (II) Peptide [Mpa-Tyr-Phe-Gln-Asn-Cys-Pro-Lys(X)$_a$-Gly [SEQ ID NO. 6]; with disulfide bond between Mpa and Cys]; for V1a receptor. A Formula (II) peptide where "(X)$_a$" has X=Gly and a=6 or 9, has EC50 of 27.3 nM or 12.6 nM for V1a receptor (n=2). It is a partial V1a agonist, with 60.9% or 55.9% highest agonist effect compared with arginine vasopressin (AVP) which is the 100% control (n=2).

V1a Human Vasopressin GPCR Cell Based Agonist Calcium Flux Assay were conducted using human recombinant CHO cells expressing human V1 receptor. Briefly, human recombinant CHO cells expressing human V1 receptor were distributed in microplates at 4.5×10$^4$ cells/well. The fluorescent probe (Fluo4 Direct, Invitrogen) mixed with probenicid in HBSS buffer (Invitrogen) complemented with 20 mM HEPES (Invitrogen) (pH 7.4) is then added into each well and equilibrated with the cells for 60 min at 37° C. then 15 min at 22° C. Thereafter, the assay plates are positioned in a microplate reader (CellLux, PerkinElmer) which is used for the addition of the test compound, reference agonist or HBSS buffer (basal control), and the measurements of changes in fluorescence intensity which varies proportionally to the free cytosolic Ca$^{2+}$ ion concentration. The following agonist concentrations were tested (nM), 0.0128, 0.064, 0.32, 1.6, 8, 40, 200, and 1,000. The results were expressed as a percent of 1,000 nM of AVP agonist response. All assays were performed in duplicate. Changes in fluorescence intensity reflected changes in the concentration of free cytosolic calcium. The standard reference agonist was AVP and the maximum activity of the other agonist were expressed as percent of maximum AVP activity. Referring to FIG. 3 and Table 4, the half-maximal effective concentration (EC50) was determined by non-linear regression analysis of the concentration-response curves generated with mean replicate values using Hill equation curve fitting (Cerep, l'Evescault, France).

TABLE 4

Peptide properties

| Peptides | Estimated V1a EC50 (nM); n = 2 | V1a Highest agonist effect (% of AVP); n = 2 |
|---|---|---|
| Arginine Vasopressin (AVP) | 0.42 | 100 |
| Lysine vasopressin (LVP) | 1.65 | 92.1 |
| Mpa-Tyr-Phe-Gln-Asn-Cys-Pro-Lys(X)$_a$-Gly-NH2; (X)$_a$ = (Gly)$_6$ [SEQ ID NO. 20] | 27.3 | 60.9 |
| Mpa-Tyr-Phe-Gln-Asn-Cys-Pro-Lys(X)$_a$-Gly-NH2; (X)$_a$ = (Gly)$_9$ [SEQ ID NO. 23] | 12.6 | 55.9 |

Example 5: Combination Therapy with Tolvaptan and with Terlipressin in Acute Diuretic Activity in Wistar Rats (Table 5)

In this study, Male Wistar Rats (~8 weeks; Envigo; Somerset, NJ) were fasted overnight (18 hours; free access to water) followed by treatment with saline at 20 ml/Kg via oral gavage to have a uniform hydration of all the animals. The animals were then treated with Terlipressin (Bachem, Torrance CA), Tolvaptan (Fisher Scientific, Waltham, MA) and combination of the two compounds at various concentrations administered subcutaneously (n=4). Test articles were Terlipressin 0.05 mg/Kg and 0.15 mg/Kg, Tolvaptan 0.3 mg/Kg, and 1.0 mg/Kg, Terlipressin 0.05 mg/Kg+Tolvaptan 0.3 mg/Kg, Terlipressin 0.05 mg/Kg+Tolvaptan 1.0 mg/Kg, Terlipressin 0.15 mg/Kg+Tolvaptan 0.3 mg/Kg, and Terlipressin 0.15 mg/Kg+1.0 mg/Kg. Furosemide (Fisher Scientific, Waltham, MA) was used as positive control and dosed at 20 mg/kg via oral gavage. Control dosed vehicle group (9% tween 80; Fisher Scientific, Waltham MA) administered subcutaneously was included and the resulting data was subtracted from individual test article data. After the dose, animals were placed in the metabolic cage (Tecniplast; Province of Varese, Italy) and urine was collected and measured at 2, 4 and 8 hours after the dosing of test articles. Urine volumes were divided by the body weight (pre-dose) times 100 to express in ml/100 g body weight. Table 4 shows that at low dose of subcutaneous tolvaptan (0.3 mg/Kg), a Terlipressin to Tolvaptan wt ratios of 1:2 to 1:6 combinations are preferable and have additive effect on total urine volume and comparable to the combine total urine volume when administered independently. A high dose of tolvaptan and a ratio of 1:7 to 1:20 have subtractive effect on total urine volume and is less than the combine total volume when administered independently. However, at any ratio, a tolvaptan dose of about 0.3 mg/Kg (i.e., 0.3±0.05 mg/Kg) administered in rats (allometrically equivalent to about 2-5 mg/human depending on weight) is an ideal dose that when combined with the composition of the present disclosure provides greater than 50% of the sum of individual diuretic effect administered alone. Low dose of 0.3 mg/Kg of subcutaneous tolvaptan is considered to be 13-fold below the effective safe human dose thus providing additional advantage to patients with liver disease. This can increase mean arterial blood pressure (MAP) which is a V1a effect caused by composition of the present disclosure while maintaining significant (at least 50% of the sum of individual diuretic effect administered alone) of both.

TABLE 5

Terlipressin to Tolvaptan wt ratios of 1:2 to 1:6 (but not other ratios) have additive effect on total urine volume and comparable to the combine total volume when administered independently, allowing for reduction of hepatotoxic tolvaptan dose.

| Test Articles | Tolvaptan: Test article ratio wt:wt | Average mL of Urine per 100 gram body weight 8 hours cumulative (n = 4) minus Vehicle group (Tween 80) of 0.92 mL (0.15; SEM; n = 4) |
|---|---|---|
| Terlipressin 0.05 | N/A | 0.70 (0.17) |
| Terlipressin 0.15 | N/A | 1.32 (0.23) |
| Tolvaptan 0.3 | N/A | 0.65 (0.16) |
| Tolvaptan 1.0 | N/A | 7.29 (0.46) |
| Terlipressin 0.05: Tolvaptan 0.3 W/W 1:6 | 1:6 | 1.41 (0.21) |
| Terlipressin 0.05: Tolvaptan 1.0 W/W 1:20 | 1:20 | 3.01 (0.19) |
| Terlipressin 0.15: Tolvaptan 0.3 W/W 1:2 | 1:2 | 1.84 (0.09) |
| Terlipressin 0.15: Tolvaptan 1.0 W/W 1:7 | 1:7 | 2.61 (0.09) |
| Furosemide 20 (Oral) | N/A | 1.73 (0.22) |

Example 6: Combination Therapy with Tolvaptan and with Peptides of Formula (II) and (IV) in Acute Diuretic Activity in Wistar Rats (Table 6)

In this study, Male Wistar Rats (~8 weeks; Envigo; Somerset, NJ) were fasted overnight (18 hours; free access to water) followed by treatment with saline at 20 ml/Kg via oral gavage to have a uniform hydration of all the animals. The animals were then treated with various concentrations of test articles administered subcutaneously (n=4) (Table 5). Control dosed vehicle group (9% tween 80; Fisher Scientific, Waltham MA) administered subcutaneously was included and the resulting data was subtracted from individual test article data. After the dose, animals were placed in the metabolic cage (Tecniplast; Province of Varese, Italy) and urine was collected and measured at 2, 4 and 8 hours after the dosing of test articles. Urine volumes were divided by the body weight (pre-dose) times 100 to express in ml/100 g body weight. Table 4 shows that at low dose of subcutaneous tolvaptan (0.3 mg/Kg), a Terlipressin to Tolvaptan wt ratios of 1:2 to 1:6 combinations are preferable and have additive effect on total urine volume and comparable to the combine total urine volume when administered independently. A high dose of tolvaptan and a ratio of 1:7 to 1:20 have subtractive effect on total urine volume and is less than the combine total volume when administered independently. However, at any ratio, a tolvaptan dose of about 0.3 mg/Kg (i.e., 0.3+0.05 mg/Kg) administered in rats (allometrically equivalent to about 2-7 mg/human depending on persons weight) is an ideal dose that when combined with the composition of the present disclosure provides greater than 50% of the sum of individual diuretic effect administered alone. Low dose of 0.3 mg/Kg of subcutaneous tolvaptan is considered to be 13-fold below the effective safe human dose thus providing additional advantage to patients with liver disease. This can increase mean arterial blood pressure (MAP) which is a V1a effect caused by composition of the present disclosure while maintaining significant (at least 50% of the sum of individual diuretic effect administered alone) of both.

TABLE 6

Tolvaptan at 0.3 mg/Kg in rats and several peptides of Formula (II) and (IV) in Acute Diuretic Activity in Wistar Rats.

| Test Articles | Tolvaptan: Formula II ratio wt:wt | Average 8 hours cumulative Urine Volume: mL per 100 gram body weight (SEM; n = 4) minus Tween 80 vehicle group |
|---|---|---|
| Tolvaptan; 0.3 mg/kg | N/A | 0.65 (0.16) |
| Mpa-Tyr-Phe-Gln-Asn-Cys-Pro-Lys-Gly-NH$_2$ [SEQ ID NO. 32]; 0.005 mg/kg | N/A | 0.80 (0.50) |
| Mpa-Tyr-Phe-Gln-Asn-Cys-Pro-Lys-Gly-NH$_2$ [SEQ ID NO. 32]; 0.015 mg/kg | N/A | 0.86 (0.28) |
| Mpa-Tyr-Phe-Gln-Asn-Cys-Pro-Lys-Gly-NH$_2$ [SEQ ID NO. 32]; 0.05 mg/kg | N/A | 0.74 (0.55) |

TABLE 6-continued

Tolvaptan at 0.3 mg/Kg in rats and several peptides of Formula (II) and (IV) in Acute Diuretic Activity in Wistar Rats.

| Test Articles | Tolvaptan: Formula II ratio wt:wt | Average 8 hours cumulative Urine Volume: mL per 100 gram body weight (SEM; n = 4) minus Tween 80 vehicle group |
|---|---|---|
| Mpa-Tyr-Phe-Gln-Asn-Cys-Pro-Lys(X)$_a$-Gly-NH$_2$; (X)$_a$ = (Gly)$_5$ [SEQ ID NO. 33]; 0.015 mg/kg | N/A | 1.11 (0.11) |
| Mpa-Tyr-Phe-Gln-Asn-Cys-Pro-Lys(X)$_a$-Gly-NH$_2$; (X)$_a$ = (Gly)$_5$ [SEQ ID NO. 33]; 0.05 mg/kg | N/A | 1.32 (0.09) |
| Mpa-Tyr-Phe-Gln-Asn-Cys-Pro-Lys(X)$_a$-Gly-NH$_2$; (X)$_a$ = (Gly)$_5$ [SEQ ID NO. 33]; 0.15 mg/kg | N/A | 1.85 (0.20) |
| Tolvaptan: 0.3 mg/kg + Mpa-Tyr-Phe-Gln-Asn-Cys-Pro-Lys-Gly-NH$_2$ [SEQ ID NO. 32]: 0.005 mg/kg | 1:60 | 0.97 (0.29) |
| Tolvaptan: 0.3 mg/kg + Mpa-Tyr-Phe-Gln-Asn-Cys-Pro-Lys-Gly-NH$_2$ [SEQ ID NO. 32]: 0.015 mg/kg | 1:20 | 1.43 (0.14) |
| Tolvaptan: 0.3 mg/kg + Mpa-Tyr-Phe-Gln-Asn-Cys-Pro-Lys-Gly-NH$_2$ [SEQ ID NO. 32]: 0.05 mg/kg | 1:6 | 0.48 (0.31) |
| Tolvaptan: 0.3 mg/kg + Mpa-Tyr-Phe-Gln-Asn-Cys-Pro-Lys(X)$_a$-Gly-NH$_2$; (X)$_a$ = (Gly)$_5$ [SEQ ID NO. 33]: 0.015 mg/kg | 1:20 | 0.88 (0.04) |
| Tolvaptan: 0.3 mg/kg + Mpa-Tyr-Phe-Gln-Asn-Cys-Pro-Lys(X)$_a$-Gly-NH$_2$; (X)$_a$-(Gly)$_5$ [SEQ ID NO. 33]: 0.05 mg/kg | 1:6 | 1.66 (0.18) |
| Tolvaptan: 0.3 mg/kg + Mpa-Tyr-Phe-Gln-Asn-Cys-Pro-Lys(X)$_a$-Gly-NH$_2$; (X)$_a$ = (Gly)$_5$ [SEQ ID NO. 33]: 0.15 mg/kg | 1:2 | 1.52 (0.04) |

Example 7: Compositions of the Present Disclosure have Much Higher Therapeutic Index than Other Known V$_2$a Agonists In this study, 8 to 10 weeks male Sprague-Dawley rats (Charles River; Wilmington, MA) under isoflurane anesthesia (n=3 or 6) were intravenously (IV) or subcutaneously (SC) injected or administered with various test articles. Prior to administration of test articles, the injection area was clipped free of fur, to allow for clear visualization of the dose site, and animal weight was measured and recorded. Animals were housed two per cage. After each injection animals were observed at least every 30 mins up to 8 hours and checked them the next day. The start and end time of the symptoms were recorded and summarized in Table 6. The definition for no-observed-effect level (NOEL) is the highest dose of test article where the animal showed no symptom at all within 24 hr after injection when compared to untreated control. The definition for no-observed-adverse-effect level (NOAEL) is the highest dose where the animal showed ear paleness after injection but not lethargy when compared to untreated control. The definition of Mild adverse effect is the lowest dose where the animal showed lethargy in addition to paleness of the ears when compared to untreated control. The definition of Marked Adverse effect is the lowest dose where the animal showed ataxia in addition to lethargy and paleness of the ears when compared to untreated control. Lethargy is when the animal eyes cannot fully open and is associated deep breathing and limited of movement even in the presence of human. Ataxia is when the animal showed mobility problem which is evident by animal laying on its side. After 24 hrs, none of four symptom classifications were observed indicating that the test articles and/or the drug activities were cleared/metabolized/degraded from the system/body.

TABLE 7

The compositions of the present disclosure have much higher therapeutic index than other known V1a agonists (*The last timepoint for observation. 24 hours later, the clinical signs were back to normal).

| Terlipressin (n = 3) | Dose mg/Kg I.V. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.005 | None observed | None observed | None observed | 10 |
| Highest dose with no-observed adverse effect level without lethargy (NOAEL) | 0.05 | observed (1.3 ± 0.05) | None observed | None observed | |
| Mild adverse effect (Lowest dose first showed Lethargy) | 0.15 | observed (2.82 ± 0.03) | observed (0.66 ± 0.02) | None observed | |
| Marked adverse effect (Lowest dose first showed Ataxia) | 1.5 | observed (3.56 ± 0.06) | observed (1.16 ± 0.06) | observed (0.58 ± 0.06) | |

| Mpa-Tyr-Phe-Hgn-Asn-Cys-Pro-Lys-Gly-NH2 [SEQ ID NO. 25]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None observed | None observed | None observed | 10 (More potent and has bioactivity 3x longer than terlipressin) |
| Highest dose with no-observed adverse effect level without lethargy (NOAEL) | 0.015 | observed (3.78 ± 0.05) | None observed | None observed | |
| Mild adverse effect (Lowest dose first showed Lethargy) | 0.05 | observed (5.66 ± 0.83) | observed (1.49 ± 0.37) | None observed | |
| Marked adverse effect (Lowest dose first showed Ataxia) | 0.15 | observed (4.9 ± 0.05) | observed (2.98 ± 0.07) | observed (0.62 ± 0.04) | |

| Mpa-Tyr-Phe-Hgn-Asn-Cys-Pro-Lys(X)$_a$-Gly-NH2; (X)$_a$ = (Gly)$_1$ [SEQ ID NO. 8]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None Observed | None Observed | None Observed | 10 |
| Highest dose with no-observed adverse effect level without lethargy (NOAEL) | 0.15 | Observed (6.20 ± 0.28) | None Observed | None Observed | |
| Mild adverse effect (Lowest dose first showed Lethargy) | 0.5 | Observed (>6.12)* | Observed (1.64 ± 0.10) | None Observed | |
| Marked adverse effect (Lowest dose first showed Ataxia) | 1.5 | Observed (>6.12)* | Observed (1.78 ± 0.21) | Observed (0.48 ± 0.06) | |

| Mpa-Tyr-Phe-Hgn-Asn-Cys-Pro-Lys(X)$_a$-Gly-NH2; (X)$_a$ = (Gly)$_2$ [SEQ ID NO. 9]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None Observed | None Observed | None Observed | 100 |
| Highest dose with no-observed adverse effect level without lethargy (NOAEL) | 0.15 | Observed (5.74 ± 0.45) | None Observed | None Observed | |

TABLE 7-continued

The compositions of the present disclosure have much higher therapeutic index than other known V1a agonists (*The last timepoint for observation. 24 hours later, the clinical signs were back to normal).

| | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Mild adverse effect (Lowest dose first showed Lethargy) | 0.5 | Observed (>6.04)* | Observed (1.70 ± 0.13) | None Observed | |
| Marked adverse effect (Lowest dose first showed Ataxia) | 1.5 | Observed (>5.99)* | Observed (1.79 ± 0.18) | Observed (0.43 ± 0.07) | |

| Mpa-Tyr-Phe-Hgn-Asn-Cys-Pro-Lys(X)$_a$-Gly-NH2; (X)$_a$ = (Gly)$_3$ [SEQ ID NO. 10]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None observed | None observed | None observed | 100 |
| Highest dose with no-observed adverse effect level without lethargy (NOAEL) | 0.15 | observed (5.65 ± 0.4) | None observed | None observed | |
| Mild adverse effect (Lowest dose first showed Lethargy) | 0.5 | observed (6.27 ± 0.13) | observed (2.07 ± 0.07) | None observed | |
| Marked adverse effect (Lowest dose first showed Ataxia) | 1.5 | observed (6.4 ± 0.07) | observed (0.25 ± 0.1) | observed (0.33 ± 0.11) | |

| Mpa-Tyr-Phe-Hgn-Asn-Cys-Pro-Lys(X)$_a$-Gly-NH2; (X)$_a$ = (Gly)$_4$ [SEQ ID NO. 11]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None Observed | None Observed | None Observed | 100 |
| Highest dose with no-observed adverse effect level without lethargy (NOAEL) | 0.15 | Observed (6.02 ± 0.06) | None Observed | None Observed | |
| Mild adverse effect (Lowest dose first showed Lethargy) | 0.5 | Observed (>6.85)* | Observed (1.49 ± 0.02) | None Observed | |
| Marked adverse effect (Lowest dose first showed Ataxia) | 1.5 | Observed (>6.93)* | Observed (1.11 ± 0.07) | Observed (0.41 ± 0.08) | |

| Mpa-Tyr-Phe-Hgn-Asn-Cys-Pro-Lys(X)$_a$-Gly-NH2; (X)$_a$ = (Gly)$_5$ [SEQ ID NO. 12]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None Observed | None Observed | None Observed | 100 |
| Highest dose with no-observed adverse effect level without lethargy (NOAEL) | 0.15 | Observed (5.79 ± 0.08) | None Observed | None Observed | |
| Mild adverse effect (Lowest dose first showed Lethargy) | 0.5 | Observed (>6.65)* | Observed (1.37 ± 0.11) | None Observed | |
| Marked adverse effect (Lowest dose first showed Ataxia) | 1.5 | Observed (>6.69)* | Observed (1.20 ± 0.06) | Observed (0.49 ± 0.06) | |

TABLE 7-continued

The compositions of the present disclosure have much higher therapeutic index than other known V1a agonists (*The last timepoint for observation. 24 hours later, the clinical signs were back to normal).

| Mpa-Tyr-Phe-Hgn-Asn-Cys-Pro-Lys(X)$_a$-Gly-NH2; (X)$_a$ = (Gly)$_6$ [SEQ ID NO. 13]; (n = 6) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.003 | None observed | None observed | None observed | 100 |
| Highest dose with no-observed adverse effect level without lethargy (NOAEL) | 0.3 | Observed (6.07 ± 0.08) | None observed | None observed | |
| Mild adverse effect (Lowest dose first showed Lethargy) | 0.5 | observed (6.23 ± 0.06) | observed (0.95 ± 0.23) | None observed | |
| Marked adverse effect (Lowest dose first showed Ataxia) | 5.0 | observed (>5.6)* | Observed (2.65 ± 0.45) | observed (0.74 ± 0.16) | |

| Mpa-Tyr-Phe-Hgn-Asn-Cys-Pro-Lys(X)$_a$-Gly-NH2; (X)$_a$ = (Gly)$_7$ [SEQ ID NO. 14]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None Observed | None Observed | None Observed | 100 |
| Highest dose with no-observed adverse effect level without lethargy (NOAEL) | 0.15 | Observed (5.86 ± 0.13) | None Observed | None Observed | |
| Mild adverse effect (Lowest dose first showed Lethargy) | 0.5 | Observed (>6.39)* | Observed (0.80 ± 0.14) | None Observed | |
| Marked adverse effect (Lowest dose first showed Ataxia) | 1.5 | Observed (>6.44)* | Observed (1.27 ± 0.02) | Observed (0.26 ± 0.23) | |

| Mpa-Tyr-Phe-Hgn-Asn-Cys-Pro-Lys(X)$_a$-Gly-NH2; (X)$_a$ = (Gly)$_8$ [SEQ ID NO. 15]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None Observed | None Observed | None Observed | 100 |
| Highest dose with no-observed adverse effect level without lethargy (NOAEL) | 0.15 | Observed (5.68 ± 0.06) | None Observed | None Observed | |
| Mild adverse effect (Lowest dose first showed Lethargy) | 0.5 | Observed (>6.17)* | Observed (0.60 ± 0.10) | None Observed | |
| Marked adverse effect (Lowest dose first showed Ataxia) | 1.5 | Observed (>6.19)* | Observed (1.17 ± 0.08) | Observed (0.22 ± 0.06) | |

| Mpa-Tyr-Phe-Hgn-Asn-Cys-Pro-Lys(X)$_a$-Gly-NH2; (X)$_a$ = (Gly)$_9$ [SEQ ID NO. 16]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.005 | None observed | None observed | None observed | 100 |

TABLE 7-continued

The compositions of the present disclosure have much higher therapeutic index than other known V1a agonists (*The last timepoint for observation. 24 hours later, the clinical signs were back to normal).

| | | | | | |
|---|---|---|---|---|---|
| Highest dose with no-observed adverse effect level without lethargy (NOAEL) | 0.5 | Observed (7.14 ± 0.11) | None observed | None observed | |
| Mild adverse effect (Lowest dose first showed Lethargy) | 1.5 | observed (>6.14)* | observed (0.72 ± 0.10) | None observed | |
| Marked adverse effect (Lowest dose first showed Ataxia) | 5.0 | observed (>6.99)* | Observed (1.39 ± 0.21) | Observed (0.42 ± 0.19) | |
| Mpa-Tyr-Phe-Hgn-Asn-Cys-Pro-Lys(X)$_a$-Gly-NH2 [SEQ ID NO. 28]; (X)$_a$ = Ac or acetyl; (n = 3) | Dose mg/Kg S.C. | Paleness (Duration, hrs; SD) | Lethargy (duration, hrs; SD) | Ataxia (duration, hrs; SD) | NOAEL/NOEL |
| Highest dose with no-observed effect level or paleness (NOEL) | 0.1 | None Observed | None Observed | None Observed | 3 |
| Highest dose with no-observed adverse effect level without lethargy (NOAEL) | 0.33 | Observed (2.83 ± 0.08) | None Observed | None Observed | |
| Mild adverse effect (Lowest dose first showed Lethargy) | 1 | Observed (4.83 ± 0.06) | Observed (0.29 ± 0.18) | Not Applicable | |
| Marked adverse effect (Lowest dose first showed Ataxia) | 3 | Observed (>6.64)* | Observed (2.42 ± 0) | Observed (0.19 ± 0.05) | |
| Mpa-Tyr-Phe-Hgn-Asn-Cys-Pro-D-Lys-Gly-NH2 [SEQ ID NO. 18]; (n = 3) | Dose mg/Kg S.C. | Paleness (Duration, hrs; SD) | Lethargy (duration, hrs; SD) | Ataxia (duration, hrs; SD) | NOAEL/NOEL |
| Highest dose with no-observed effect level or paleness (NOEL) | 0.005 | None Observed | None Observed | None Observed | 30 |
| Highest dose with no-observed adverse effect level without lethargy (NOAEL) | 0.15 | Observed (5.38 ± 0.79) | None Observed | None Observed | |
| Mild adverse effect (Lowest dose first showed Lethargy) | 0.5 | Observed (>5.84)* | Observed (0.29 ± 0.05) | Not observed | |
| Marked adverse effect (Lowest dose first showed Ataxia) | 1.5 | Observed (>6.17)* | Observed (2.11 ± 0.03) | Observed (0.14 ± 0.04) | |
| Mpa-Tyr-Phe-Hgn-Asn-Cys-Pro-Dap-Gly-NH2 (disulfide bond) [SEQ ID NO. 17]; (n = 3) | Dose mg/Kg S.C. | Paleness (Duration, hrs; SD) | Lethargy (duration, hrs; SD) | Ataxia (duration, hrs SD) | NOAEL/NOEL |
| Highest dose with no-observed effect level or paleness (NOEL) | 0.014 | None observed | None observed | None observed | 34 |
| Highest dose with no-observed adverse effect level without lethargy (NOAEL) | 0.478 | Observed (6.11 ± 0.07) | None observed | None observed | |
| Mild adverse effect (Lowest dose first showed Lethargy) | 4.78 | Observed (>5.92)* | Observed (0.68 ± 0.10) | None observed | |
| Marked adverse effect (Lowest dose first showed Ataxia) | >9.95 | Observed (>6.18)* | Observed (1.73 ± 0) | Not done | |

TABLE 7-continued

The compositions of the present disclosure have much higher therapeutic index than other known V1a agonists (*The last timepoint for observation. 24 hours later, the clinical signs were back to normal).

| Mpa-Tyr-Phe-Hgn-Asn-Cys-Pro-Orn-Gly-NH2 (disulfide bond) [SEQ ID NO. 30]; (n = 3) | Dose mg/Kg S.C. | Paleness (Duration, hrs; SD) | Lethargy (duration, hrs; SD) | Ataxia (duration, hrs SD) | NOAEL/NOEL |
|---|---|---|---|---|---|
| Highest dose with no-observed effect level or paleness (NOEL) | 0.0005 | None observed | None observed | None observed | Between 10 and 30 (Only 12 min lethargy at 30x dose) |
| Highest dose with no-observed adverse effect level without lethargy (NOAEL) | 0.005 | Observed (5.91 ± 0.08) | None observed | None observed | |
| Mild adverse effect (Lowest dose first showed Lethargy) | 0.015 | Observed (>4.82)* | Observed (0.19 ± 0.05) | None observed | |
| Marked adverse effect (Lowest dose first showed Ataxia) | 0.044 | Observed (>4.68)* | Observed (0.78 ± 0.08) | Observed (0.26 ± 0.02) | |

| Mpa-Tyr-Phe-Hgn-Asn-Cys-Pro-Dab-Gly-NH2 (disulfide bond [SEQ ID NO. 31]; (n = 3) | Dose mg/Kg S.C. | Paleness (Duration, hrs; SD) | Lethargy (duration, hrs; SD) | Ataxia (duration, hrs SD) | NOAEL/NOEL |
|---|---|---|---|---|---|
| Highest dose with no-observed effect level or paleness (NOEL) | 0.0005 | None observed | None observed | None observed | Between 10 and 30 (Only 12 min lethargy at 30x dose) |
| Highest dose with no-observed adverse effect level without lethargy (NOAEL) | 0.005 | Observed (>5.87)* | None observed | None observed | |
| Mild adverse effect (Lowest dose first showed Lethargy) | 0.015 | Observed (>4.57)* | Observed (0.20 ± 0.08) | None observed | |
| Marked adverse effect (Lowest dose first showed Ataxia) | 0.045 | Observed (>4.39)* | Observed (1.30 ± 0.03) | Observed (0.36 ± 0.08) | |

| Mpa-Tyr-Phe-Hgn-Asn-Cys-Pro-Lys(X)$_a$-Gly-NH2; (X)$_a$ = Ac or acetyl [SEQ ID NO. 28]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.1 | None Observed | None Observed | None Observed | 3 |
| Highest dose with no-observed adverse effect level without lethargy (NOAEL) | 0.33 | Observed (2.83 ± 0.08) | None Observed | None Observed | |
| Mild adverse effect (Lowest dose first showed Lethargy) | 1 | Observed (4.83 ± 0.06) | Observed (0.29 ± 0.18) | Not Applicable | |
| Marked adverse effect (Lowest dose first showed Ataxia) | 3 | Observed (>6.64)* | Observed (2.42 ± 0) | Observed (0.19 ± 0.05) | |

| Mpa-Tyr-Phe-Hgn-Asn-Cys-Pro-Lys(X)$_a$-Gly-NH2; (X)$_a$ = Lauric acid [SEQ ID NO. 27]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.1 | None Observed | None Observed | None Observed | 90 (dose too high means low potency) |

TABLE 7-continued

The compositions of the present disclosure have much higher therapeutic index than other known V1a agonists (*The last timepoint for observation. 24 hours later, the clinical signs were back to normal).

| | | | | | |
|---|---|---|---|---|---|
| Highest dose with no-observed adverse effect level without lethargy (NOAEL) | 9 | Observed (<4.25)* | None Observed | None Observed | |
| Mild adverse effect (Lowest dose first showed Lethargy) | >9 | Not Done | Not Done | Not Done | |
| Marked adverse effect (Lowest dose first showed Ataxia) | >9 | Not Done | Not Done | Not Done | |

| Mpa-Tyr-Phe-Hgn-Asn-Cys-Pro-Lys(12-aminododecanoic acid)-Gly-NH2 [SEQ ID NO. 19]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.014 | None Observed | None Observed | None Observed | 649 (Dose too high means low potency) |
| Highest dose with no-observed adverse effect level without lethargy (NOAEL) | 9.08 | Observed (<5.83)* | None Observed | None Observed | |
| Mild adverse effect (Lowest dose first showed Lethargy) | >9.08 | Not Done | Not Done | Not Done | |
| Marked adverse effect (Lowest dose first showed Ataxia) | >9.08 | Not Done | Not Done | Not Done | |

| Mpa-Tyr-Phe-Gln-Asn-Cys-Pro-Lys-Gly-NH2 [SEQ ID NO. 32]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0005 | None observed | None observed | None observed | 20 |
| Highest dose with no-observed adverse effect level or lethargy (NOAEL) | 0.01 | Observed (3.54 ± 0.11) | None observed | None observed | |
| Mild adverse effect (Lowest dose first showed Lethargy) | 0.03 | Observed (4.45 ± 0.26) | Observed (0.37 ± 0.08) | None observed | |
| Marked adverse effect (Lowest dose first showed Ataxia) | 0.1 | Observed (4.79 ± 0.08) | Observed (0.33 ± 0.07) | Observed (0.22 ± 0.02) | |

| Mpa-Tyr-Phe-Gln-Asn-Cys-Pro-Lys(X)$_a$-Gly-NH2; (X)$_a$ = (Gly)$_6$ [SEQ ID NO. 20]; (n = 3) | Dose mg/Kg S.C. | Paleness (Duration, hrs; SD) | Lethargy (duration, hrs; SD) | Ataxia (duration, hrs; SD) | NOAEL/NOEL |
|---|---|---|---|---|---|
| Highest dose with no-observed effect level or paleness (NOEL) | 0.0015 | None observed | None observed | None observed | 100 |
| Highest dose with no-observed adverse effect level without lethargy (NOAEL) | 0.15 | Observed (6.11 ± 0.09) | None observed | None observed | |
| Mild adverse effect (Lowest dose first showed Lethargy) | 0.5 | Observed (>5.46)* | Observed (0.27 ± 0.06) | None observed | |
| Marked adverse effect (Lowest dose first showed Ataxia) | 5.0 | Observed (>6.76)* | Observed (0.91 ± 0.11) | Observed (0.21 ± 0.06) | |

TABLE 7-continued

The compositions of the present disclosure have much higher therapeutic index than other known V1a agonists (*The last timepoint for observation. 24 hours later, the clinical signs were back to normal).

| Mpa-Tyr-Phe-Gln-Asn-Cys-Pro-Lys(X)$_a$-Gly-NH2; (X)$_a$ = (Gly)$_9$ [SEQ ID NO. 23]; (n = 3) | Dose mg/Kg S.C. | Paleness (Duration, hrs; SD) | Lethargy (duration, hrs; SD) | Ataxia (duration, hrs SD) | NOAEL/NOEL |
|---|---|---|---|---|---|
| Highest dose with no-observed effect level or paleness (NOEL) | 0.0015 | None observed | None observed | None observed | 333 |
| Highest dose with no-observed adverse effect level without lethargy (NOAEL) | 0.5 | Observed (>5.09)* | None observed | None observed | |
| Mild adverse effect (Lowest dose first showed Lethargy) | 1.5 | Observed (6.23 ± 0.05) | Observed (0.29 ± 0.02) | None observed | |
| Marked adverse effect (Lowest dose first showed Ataxia) | 5.0 | Observed (>6.46)* | Observed (1.08 ± 0.03) | Observed (0.28 ± 0.01) | |

Example 8. Acute Diuretic Activity of the Combination of a Peptide of Formula (I) and Tolvaptan Through Subcutaneous Injection in Wistar Rats (Table 8)

Referring to Table 8: This study showed that at 4 and 8 hours, the combination of V2 antagonist, such as Tolvaptan (Tol), with a peptide of Formula (I) (Mpa-YFhomoQNCPK(GGGGGG)G-NH2 [SEQ ID NO. 13]; Mpa and C are disulfide bonded; represented as TA-1) given 2 hours later showed a significant increase in urine volume compared with vehicle group, and the combination showed a synergistic/additive effect of the two drugs. Dosing the drugs separately and especially dosing Tolvaptan first would be the best way to combine a peptide of Formula (I) and lower Tolvaptan at lower dose than currently use or prescribed to reach the same or higher therapeutic efficacy. Such lower therapeutic dose of Tolvaptan will mitigate known hepatotoxicity risk for many patients. For this study, the animal room temperatures were set to maintain 20 to 22° C. A 14-hour light, 10-hour dark cycle was implemented unless interrupted by study procedures. Approximately 45 minutes prior to testing the diuretic effects of various test articles, male Wistar rats (~8 weeks from Charles River Laboratory; n=4 per group) were dosed with saline at 20 ml/Kg via oral gavage (PO) to normalize the water content between animals. The following test articles and combinations were subcutaneously administrated: Group 1—Vehicle (9% Tween 80); Group 2—TA-1 alone; Group 3—Tolvaptan (Tol) alone; Group 4—TA-1 0.08 mg/kg+Tol 0.3 mg/kg administered together; Group 5—TA-1 0.08 mg/kg at time 0 followed by Tol 0.3 mg/kg after 2 hr; Group 6—Tol 0.3 mg/kg at time 0 followed by TA-1 0.08 mg/kg after 2 hr. Urine was collected and cumulative volume measured at various times after dosing.

TABLE 8

Dosing a Formula 1, represented by TA-1, after V2 antagonist (Tol) showed diuretic synergy when V2 antagonist is administered first.

| Test articles | 4 hr cumulative per 100 g body weight (SEM) | 8 hr cumulative per 100 g body weight (SEM) |
|---|---|---|
| Vehicle (9% Tween 80) | 0.3 (0.1) | 0.7 (0.1) |
| TA-1 0.08 mg/Kg only | 0.9 (0.2) | 1.2 (0.2) |
| Tol 0.3 mg/Kg only | 1.2 (0.3) | 2.2 *(0.3) |
| TA-1 0.08 mg/kg + Tol 0.3 mg/kg together | 1.0 (0.2) | 1.2 (0.2) |
| TA-1 0.08 mg/kg + Tol 0.3 mg/kg after 2 hr | 1.1 (0.2) | 1.3 (0.3) |
| Tol 0.3 mg/kg + TA-1 0.08 mg/kg after 2 hr | 3.4 ****(0.7) | 3.7 ****(0.7) |

Statistical analysis was performed with one way ANOVA in GraphPad Prism 8 compared with vehicle group (*P < 0.05,  P < 0.01, * P < 0.001, ****P < 0.0001).

Example 9. Telemetric Evaluation of the Effect of MPA-YFHOMOQNCPK(GGGGGG)G-NH$_2$ [Seq Id No. 13] and Terlipressin on Portal Vein Pressure in Rats with Bile Duct Ligation Referring to Table 9, a peptide of Formula (I) (at 12 ug/kg dose) is more effective in providing a sustain drop in portal pressure compared to Terlipressin (at 41 ug/kg dose). For this study, animals (Sprague Dawley rats (240-300 g at surgery from Charles River Laboratory) were maintained at room temperatures (20 to 22° C.) with 14-hour light, 10-hour dark cycle when not performing study procedures. The mean portal vein pressure (MPVP) reduction efficacy of a peptide of Formula (I) (Mpa-YFhomoQNCPK (GGGGGG)G-NH$_2$ [SEQ ID NO. 13]; Mpa and C are disulfide bonded; represented as TA-1) was compared to terlipressin in telemetered male with Bile Duct Ligation (BDL) and Sham surgery. On Study Day 1, rats received bile duct ligation surgery and telemetry implantation. The BDL group (n=4) had two stands of silk suture tightened and tied to occlude the bile duct; the sham group (n=3) had sutures loosely tied around the bile duct so that no occlusion occurred. After recovery from surgery, all rats had their portal vein pressure monitored continuously via telemetry until Day 22. Vehicle was administered subcutaneously on Day 14; a peptide of Formula (I) was administered at different concentrations subcutaneously on Day 15 to 19, and Day 23; Terlipressin was administered through intravenous bolus into a lateral tail vein on Day 20 and 21. All animals were dosed under manual restraint. Systolic portal vein pressure and diastolic portal vein pressure were measured to calculate the Mean Portal Vein Pressure (MPVP); MPVP was analyzed by averaging 5 minute intervals for the first 4 hours after dose and thereafter averaging 1 hour intervals after dose until 24 hours. Time zero (TO) was calculated using the average of 45 minutes to 15 minutes prior to dosing.

Telemetric evaluation of Mpa-YFhomoQNCPK (GGGGGG)G-NH2 [SEQ ID NO. 13] and Terlipressin on portal vein pressure in rats with bile duct ligation. The animal room temperatures were set to maintain 20 to 22° C. A 14-hour light, 10-hour dark cycle was implemented unless interrupted by study procedures. Efficacy was assessed by evaluating mean portal vein pressure (MPVP) at different concentrations of Formula 1 and Terlipressin in telemetered male Sprague Dawley rats (240-300 g at surgery from Charles River Laboratory) with Bile Duct Ligation (BDL) and Sham surgery. On Study Day 1, rats received bile duct ligation surgery and telemetry implantation. The BDL group (n=4) had two stands of silk suture tightened and tied to occlude the bile duct; the sham group (n=3) had sutures loosely tied around the bile duct so that no occlusion occurred. After recovery from surgery, all rats had their portal vein pressure monitored continuously via telemetry until Day 22. Vehicle was administered subcutaneously on Day 14; Formula 1 was administered at different concentrations subcutaneously on Day 15 to 19, and Day 23; Terlipressin was administered through intravenous bolus into a lateral tail vein on Day 20 and 21. All animals were dosed under manual restraint. Systolic portal vein pressure and diastolic portal vein pressure were measured to calculate the Mean Portal Vein Pressure (MPVP); MPVP was analyzed by averaging 5 minute intervals for the first 4 hours after dose and thereafter averaging 1 hour intervals after dose until 24 hours. Time zero (TO) was calculated using the average of 45 minutes to 15 minutes prior to dosing.

TABLE 9

Formula 1 (12 ug/kg) is more effective in providing a sustain drop in portal pressure compared to Terlipressin (41 ug/kg)
Percent decrease (%) in Mean Portal Vein Pressure (MPVP) from BDL baseline prior to treatment

| Test Article | Concentration (μg/kg) | 0 | 1 | 4 | 7 | 20 |
|---|---|---|---|---|---|---|
| BDL Formula 1 n = 4 | 12 | 0 | 5 (7.39) | −30.5 (7.12) | −10.5 (14.79) | −29.75 (5.0) |
| BDL Terlipressin n = 4 | 41 | 0 | −23 (21.0) | 11.3 (20.3) | 10.8 (7.7) | 7.3 (13.03) |

Data Displayed as Percent Change (SEM)

Day 13 MPVP: Portal pressure of BDL animals=22.2 mmHg (SEM:6.45); Portal pressure of Sham Animals=14.08 mmHg (SEM:1.51)

Example 10. Assays for Binding/Activity Against Various Receptors and/or Targets to Evaluate Specificity and Safety The inhibition assays for receptor binding, channel uptake activity, and enzyme activity (Safetyscreen87) were conducted on a fee for service basis at Eurofins Cerep SA (France) with various conditions appropriate for each receptor/enzyme/channel. In each experiment and if applicable, the respective reference compound was tested concurrently with the test compounds, and the data were compared with historical values determined at Eurofins. The experiment was accepted in accordance with Eurofins validation Standard Operating Procedure. Each test compound was tested in duplicates and the mean value was reported. Compound binding was calculated as a % inhibition of the binding of a radioactively labeled ligand specific for each target. Compound enzyme inhibition effect was calculated as a % inhibition of control enzyme activity (each receptors result is not shown here). Results showing an inhibition or stimulation higher than 50% are considered to represent significant effects of the test compounds. Fifty percent is the most common cut-off value and the any test articles that does not exceed 50% threshold in any of the 87 off-target proteins that are critical for drug safety is considered safe.

In general, for competitive binding assay, cell membrane homogenates were prepared from appropriate cell lines. Radiolabeled ligand was added the homogenate in the absence or presence of test compounds (10 μM) and incubated for appropriate time at appropriate temperature. Non-specific binding was determined with appropriate control. Following incubation, the samples were filtered rapidly under vacuum through glass fiber filters (Perkin Elmer; Waltham, MA) and rinsed several times with ice-cold buffer using a 96-sample cell harvester (Perkin Elmer; Waltham, MA). The filters are dried then counted for radioactivity in a scintillation counter using a scintillation cocktail (Perkin Elmer; Waltham, MA). The results are expressed as a percent inhibition of the control radioligand specific binding.

For Enzyme and Uptake Assay, the test compounds (10 μM), reference compound or water (as control) are mixed with enzyme in a buffer. The reaction is initiated by adding appropriate substrate solutions, then the mixture was incubated for compound appropriate duration at appropriate temperature. The fluorescence (related to enzyme activity) was measured using a microplate reader (Envision, Perkin Elmer; Waltham, MA). An identical plate without enzyme was prepared at the same time to verify background fluorescence or compound interference with the fluorometric detection method at appropriate wavelengths. The enzyme activity is determined by subtracting the signal measured without enzyme from the measured with enzyme. The results were expressed as a percent inhibition of the control enzyme activity.

Formula (I) Peptides wherein $(X)_a$ is $(Gly)_{0-9}$ showed similar safety profile as lysine vasopressin (LVP) using 10 μM, which is 280 folds higher than predicted highest plasma level (50 ng/mL) for therapeutic efficacy in related receptors. The Formula (I) Peptides showed no significant effects (>50% inhibition will be significant) on these receptors except V1a receptor as expected. Safetyscreens87 panels' list includes: mGluR5 (h) (agonist radioligand), 5-HT transporter (h) (antagonist radioligand), 5-HT1A (h) (agonist radioligand), 5-HT1B (h) (antagonist radioligand), 5-HT2A (h) (agonist radioligand), 5-HT2B (h) (agonist radioligand), 5-HT2C (h) (antagonist radioligand), 5-HT3 (h) (antagonist radioligand), A1 (h) (antagonist radioligand), A2A (h) (agonist radioligand), ACE (h), acetylcholinesterase (h), adenosine transporter (antagonist radioligand), alpha 1A (h) (antagonist radioligand), alpha 1B (h) (antagonist radioligand), alpha 1D (h) (antagonist radioligand), alpha 2A (h) (antagonist radioligand), alpha 2B (h) (antagonist radioligand), AMPA (agonist radioligand), AR(h) (agonist radioligand), AT1 (h) (antagonist radioligand), ATPase (Na+/K+), B2 (h) (agonist radioligand), beta 1 (h) (agonist radioligand), beta 2 (h) (antagonist radioligand), BZD (central) (agonist radioligand), Ca2+channel, (L, dihydropyridine site) (antagonist radioligand), Ca2+ channel (L, diltiazem site) (benzothiazepines) (antagonist radioligand), Ca2+ channel (L, verapamil site) (phenylalkylamine) (antagonist radioligand), Ca2+ channel (N) (antagonist radioligand), cathepsin G (h), CB1 (h) (agonist radioligand), CB2 (h) (agonist radioligand), CCK1 (CCKA) (h) (agonist radioligand), CCK2 (CCKB) (h) (agonist radioligand), CCR1 (h) (agonist radioligand), Cl— channel (GABA-gated) (TBOB site) (antagonist radioligand), COX1(h), COX2(h), CXCR2 (IL-8B) (h) (agonist radioligand), CysLT1 (LTD4) (h) (agonist radioligand), D1 (h) (antagonist radioligand), D2L (h) (antagonist radioligand), D2S (h) (agonist radioligand), delta (DOP) (h) (agonist radioligand), dopamine transporter (h) (antagonist radioligand), Estrogen ER alpha (h) (agonist radioligand), ETA (h) (agonist radioligand), GABA transporter (antagonist radioligand), GABAA1 (h) (alpha 1, beta 2, gamma 2) (agonist radioligand), glycine (strychnine-insensitive) (antagonist radioligand), glycine (strychnine-sensitive) (antagonist radioligand), GR (h) (agonist radioligand), H1 (h) (antagonist radioligand), H2 (h) (antagonist radioligand), IRK (h) (InsR), kainate (agonist radioligand), kappa (h) (KOP) (agonist radioligand), KV channel (antagonist radioligand), Lck kinase (h), M1 (h) (antagonist radioligand), M2 (h) (antagonist radioligand), M3 (h) (antagonist radioligand), M4 (h) (antagonist radioligand), MAO-A (antagonist radioligand), MAO-B (h) recombinant enzyme, MC1 (agonist radioligand), MC4 (h) (agonist radioligand), mu (MOP) (h) (agonist radioligand), N muscle-type (h) (antagonist radioligand), N neuronal alpha 4beta 2 (h) (agonist radioligand), Na+ channel (site 2) (antagonist radioligand), NK1 (h) (agonist radioligand), NMDA (antagonist radioligand), norepinephrine transporter (h) (antagonist radioligand), PAF (h) (agonist radioligand), PCP (antagonist radioligand), PDE3A (h), PDE4D2 (h), PKCalpha (h), Potassium Channel hERG (human)-[3H] Dofetilide, PPARgamma (h) (agonist radioligand), PR (h) (agonist radioligand), RARalpha (h) (agonist radioligand), V1a (h) (agonist radioligand), and Y1 (h) (agonist radioligand).

By example and without limitation, embodiments are disclosed according to the following enumerated paragraphs:

A1. A composition, comprising:
a V1a partial agonist peptide of Formula (A)

(A)
[SEQ ID NOS. 1-2]
[Mpa-Tyr-Phe-Z-Asn-Cys-Pro-B(X)$_a$-Gly-NH$_2$]

or a pharmaceutically effective salt thereof,
wherein:
the Mpa and Cys residues are covalently connected with a disulfide bond,
Z is Hgn or Gln;
wherein when Z is Hgn [SEQ ID NO. 1]:
B is any one of L-Lys, D-Lys, L-Orn, D-Orn, L-Dab, D-Dab, L-Dap, or D-Dap, and X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is an integer from 0 to 10 (e.g., from 0 to 1, from 1 to 2, from 1 to 3, from 1 to 10, from 1 to 6, from 4 to 10, or from 6 to 10), or X is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is an integer from 1 to 3;

wherein when Z is Gln [SEQ ID NO. 2]:
B is any one of L-Lys, D-Lys, L-Orn, D-Orn, L-Dab, D-Dab, L-Dap, or D-Dap, and X is an amino acid residue, wherein the amino acid residue is independently selected at each occurrence from Gly, L-Ala, D-Ala, L-Lys, D-Lys, L-Orn, D-Orn, L-Glu, D-Glu, L-Asp, and D-Asp, and a is an integer from 6 to 10, or X is a moiety derived from a non-alpha primary amino group-containing $C_{3-12}$ fatty acid (e.g., $C_{3-6}$, $C_{3-10}$, $C_{4-12}$, $C_{4-6}$, $C_{4-10}$, $C_{6-10}$, $C_{8-10}$, or $C_{10-12}$ fatty acid), and a is an integer from 1 to 3; and wherein the composition has a therapeutic index of at least 20 (e.g., at least 30, at least 40, at least 50, at least 60, at least 70, at least 80, at least 90, or at least 100).

A2. The composition of Paragraph A1, wherein Z is Hgn and B is Lys.

A3. The composition of Paragraph A1 or Paragraph A2, wherein Z is Hgn, X is Gly, and a is 0, 1, 2, 3, 4, 5, 6, 7, 8, 9, or 10.

A4. The composition of any one of the preceding Paragraphs, wherein Z is Hgn, X is Gly, and a is 6, 7, 8, 9, or 10.

A5. The composition of Paragraph A1, wherein Z is Gln and B is L-Lys.

A6. The composition of Paragraphs A1 or A5, wherein Z is Gln, B is L-Lys, X is Gly, and a is 6, 7, 8, 9, or 10.

A7. The composition of Paragraph A1, wherein Z is Hgn and B is D-Lys.

A8. The composition of Paragraph A1, wherein Z is Hgn and B is L-Orn.

A9. The composition of Paragraph A1, wherein Z is Hgn and B is D-Orn.

A10. The composition of Paragraph A1, wherein Z is Hgn and B is L-Dab.

A11. The composition of Paragraph A1, wherein Z is Hgn and B is D-Dab.

A12. The composition of Paragraph A1, wherein Z is Hgn and B is L-Dap.

A13. The composition of Paragraph A1, wherein Z is Hgn and B is D-Dap.

A14. The composition of any one of the preceding Paragraphs, further comprising a pharmaceutically acceptable excipient,
wherein the pharmaceutically acceptable excipient optionally comprises a buffer comprising a buffering pH of from 3.5 to 6.5, and
wherein the buffer is optionally selected from an acetate buffer, a citrate buffer, a succinate buffer, a histidine buffer, or any combination thereof.

A15. A method of treating a subject, comprising:
administering to a subject in need thereof a therapeutically effective dose of a composition of any one of the preceding Paragraphs,
wherein the subject has a condition selected from liver fibrosis, cirrhosis, portal hypertension, ascites, esophageal varices, fundal varices, bleeding, arterial hypotension, hepatorenal syndrome, and any combination thereof, or
  wherein the subject has liver fibrosis; or
  wherein the subject has cirrhosis; or
  wherein the subject has portal hypertension; or
  wherein the subject has ascites; or
  wherein the subject has refractory ascites; or
  wherein the subject has esophageal varices; or
  wherein the subject has gastric varices in the fundal region; or
  wherein the subject has bleeding varices; or
  wherein the subject has arterial hypotension; or wherein the subject has hepatorenal syndrome.

A16. The method of Paragraphs A15, administering to a subject in need thereof a therapeutically effective dose of a composition of any one of Paragraphs A2 to A6.

A17. The method of Paragraph A15, wherein Z is Hgn, B is L-Lys, and X is Gly.

A18. The method of Paragraph A17, wherein a is 6.

A19. The method of Paragraph A15, wherein Z is Gln and B is L-Lys.

A20. The method of any one of Paragraphs A15 to A19, wherein the subject has cirrhosis and portal hypertension.

A21. The method of any one of Paragraphs A15 to A20, wherein the subject has portal hypertension with a hepatic venous pressure gradient of 5 mm Hg and greater.

A22. The method of any one of Paragraphs A15 to A21, wherein the subject has clinically significant portal hypertension with a hepatic venous pressure gradient of 10 mm Hg and greater.

A23. The method of any one of Paragraphs A15 to A22, wherein the subject has ascites.

A24. The method of any one of Paragraphs A15 to A23, wherein the subject has refractory ascites.

A25. The method of any one of Paragraphs A15 to A24, wherein the subject has varices.

A26. The method of any one of Paragraphs A15 to A25, wherein the subject has variceal bleeding.

A27. The method of any one of Paragraphs A15 to A26, wherein the subject has a mean arterial pressure of below 95 mm Hg (e.g., below 90 mm Hg, below 85 mm Hg, below 80 mm Hg, below 75 mm Hg, or below 70 mm Hg).

A28. The method of any one of Paragraphs A15 to A27, wherein administration comprises parenteral administration.

A29. The method of any one of Paragraphs A15 to A28, wherein administration comprises intravenous administration.

A30. The method of any one of Paragraphs A15 to A28, wherein administration comprises subcutaneous administration.

A31. The method of any one of Paragraphs A15 to A28, wherein administration comprises slow infusion.

A32. The method of any one of Paragraphs A15 to A30, wherein administration comprises bolus administration.

A33. The method of any one of Paragraphs A15 to A30 and A32, wherein administration comprises a frequency of three times or less a day (e.g., administration of once every 8 hours, administration of once every 12 hours, or administration of once every 24 hours).

A34. The method of Paragraph A33, wherein the administration occurs only during daylight hours of between 6:00 and 18:00 (24 hour clock) at a frequency of once every 4 to 6 hours, and wherein administration does not occur at night between 18:00 and 6:00 (24 hour clock).

A35. The method of any one of Paragraphs A15 to A34, further comprising administering a V2 antagonist.

A36. The method of Paragraph A35, wherein the V2 antagonist is administered within 1 to 8 hours, preferably 1 to 3 hours, before or after administration of the V1a partial agonist, preferably before administration of the V1a partial agonist.

A37. A method of treating a subject, comprising:
  administering to a subject in need thereof a therapeutically effective dose of a pharmaceutical composition comprising a peptide of Formula (B), administered within 1 to 8 hours, preferably 1 to 3 hours, before or after administration of a therapeutically effective dose of a V2 antagonist, preferably after administration of a therapeutically effective dose of the V2 antagonist, wherein the peptide of Formula (B) is
  a V1a agonist peptide of Formula (B)

(B)
[SEQ ID NOS. 3-4]
[X'-Tyr-Phe-Gln-Asn-Cys-Pro-Lys(Z)$_d$-Gly-NH$_2$]

or a pharmaceutically acceptable salt thereof,
wherein:
  X' is (U)$_c$-Cys or Mpa,
  wherein when X' is (U)$_c$-Cys and (Z)$_d$ is absent [SEQ ID NO. 3],
    the 2 Cys residues are covalently connected with a disulfide bond;
  U is an amino acid residue and at each occurrence, is independently selected from Gly, L-Ala, D-Ala, L-Lys, D-Lys, L-Orn, D-Orn, L-Glu, D-Glu, L-Asp, and D-Asp, and c is an integer of from 0 to 10; and
  wherein when X' is Mpa [SEQ ID NO. 4],
    the Mpa and Cys residues are covalently connected with a disulfide bond,
  Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and d is an integer from 0 to 5,
  wherein the subject has a condition selected from liver fibrosis, cirrhosis, portal hypertension, ascites, esophageal varices, fundal varices, bleeding, arterial hypotension, hepatorenal syndrome, and any combination thereof; or
    wherein the subject has liver fibrosis; or
    wherein the subject has cirrhosis; or
    wherein the subject has portal hypertension; or
    wherein the subject has esophageal varices; or
    wherein the subject has fundal varices; or
    wherein the subject has bleeding varices; or
    wherein the subject has arterial hypotension; or
    wherein the subject has hepatorenal syndrome.

A38. The method of Paragraph A37, wherein the V1a agonist peptide of Formula (B) is a V1a agonist peptide of Formula (III)

(III)
[SEQ ID NO. 7]
[(U)$_c$-Cys-Tyr-Phe-Gln-Asn-Cys-Pro-Lys-Gly-NH$_2$]

or a pharmaceutically effective salt thereof,
wherein:
  the 2 Cys residues are covalently connected with a disulfide bond,
  U is an amino acid residue and at each occurrence, is independently selected from Gly, L-Ala, D-Ala, L-Lys, D-Lys, L-Orn, D-Orn, L-Glu, D-Glu, L-Asp, and D-Asp, and
  c is an integer of from 0 to 10.

A39. The method of Paragraph A37, wherein the V1a agonist peptide of Formula (B) is a V1a agonist peptide of Formula (IV)

(IV)
[SEQ ID NO. 4]
[Mpa-Tyr-Phe-Gln-Asn-Cys-Pro-Lys(Z)$_d$-Gly-NH$_2$]

or a pharmaceutically effective salt thereof,
wherein:
the Mpa and Cys residues are covalently connected with a disulfide bond,
Z is an amino acid residue and at each occurrence, is independently selected from Gly, D-Ala, L-Ala, D-Lys, L-Lys, D-Orn, L-Orn, D-Glu, L-Glu, D-Asp, and L-Asp, and
d is an integer from 0 to 5.

A40. The method of any one of Paragraphs A35 to A39, wherein the V2 antagonist comprises mozavaptan, tolvaptan, tolvaptan phosphate ester, satavaptan, lixivaptan, conivaptan, RWJ-351647, VP-343, VP-393, [PmP1, D-Ile2, Ile4, Arg8, Ala9] vasopressin, [PmP1, D-Ile2, Ile4, Arg8] vasopressin, [PmP1, D-Ile2, Ile4, Arg8, Ala9] vasopressin-(1-8)-OH, or any combination thereof.

A41. The method of any one of Paragraphs A35 or A40, wherein the V2 antagonist is tolvaptan, optionally administered parenterally at a dose of from 1 µg/kg to 300 µg/kg (e.g., from 1 µg/kg to 200 µg/kg, or from 1 µg/kg to 100 µg/kg).

A42. The method of any one of Paragraphs A35 to A41, wherein the subject is human, and the V2 antagonist is tolvaptan, optionally administered parenterally at a dose of from 2 mg to 7 mg.

A43. The method of any one of Paragraphs A38 and A40 to A42, wherein the pharmaceutical composition comprises the V1a agonist peptide of Formula (III), or a pharmaceutically acceptable salt thereof, wherein U is Gly and c is 3; wherein the V2 antagonist comprises tolvaptan; and wherein the dose weight ratio of the V1a agonist peptide to tolvaptan is from 1:6 to 1:2.

A44. The method of any one of Paragraphs A15 to A43, wherein V1a partial agonist or V1a agonist is administered at a dose less than 150 nmol/dose/Kg (e.g., less than 140 nmol/dose/Kg, less than 130 nmol/dose/Kg, less than 120 nmol/dose/Kg, less than 110 nmol/dose/Kg, less than 100 nmol/dose/Kg, less than 90 nmol/dose/Kg, less than 80 nmol/dose/Kg, less than 70 nmol/dose/Kg, or less than 50 nmol/dose/Kg).

While illustrative embodiments have been illustrated and described, it will be appreciated that various changes can be made therein without departing from the spirit and scope of the invention.

SEQUENCE LISTING

```
<160> NUMBER OF SEQ ID NOS: 35

<210> SEQ ID NO 1
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as any one
      of L-Lysine, D-Lysine, L-Ornithine, D-Ornithine, L-Diaminobutyric
      acid, D-Diaminobutyric acid, L-Diaminopimelic acid, [cont.]
<220> FEATURE:
<221> NAME/KEY: MISC_FEATURE
<222> LOCATION: (7)..(7)
<223> OTHER INFORMATION: [cont.] or D-Diaminopimelic acid, and wherein
      from 0 to 10 amino acid residues selected independently at each
      occurrence from Gly, L-Ala, D-Ala, L-Lys, D-Lys, L-Orn, D-Orn,
      L-Glu, D-Glu, [cont.]
<220> FEATURE:
<221> NAME/KEY: MISC_FEATURE
<222> LOCATION: (7)..(7)
<223> OTHER INFORMATION: [cont] L-Asp, and D-Asp is attached to the R
      group of the amino acid; or attached to the R group of the amino
      acid is from 1 to 3 moieties selected independently at each
      [cont.]
<220> FEATURE:
<221> NAME/KEY: MISC_FEATURE
<222> LOCATION: (7)..(7)
<223> OTHER INFORMATION: [cont.] occurrence from a moiety derived from a
      non-alpha primary amino group-containing a C3-12 fatty acid

<400> SEQUENCE: 1
```

```
Xaa Phe Xaa Asn Cys Pro Xaa Gly
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (7)..(7)
<223> OTHER INFORMATION: Wherein X at position 7 is defined as any one
      of L-Lysine, D-Lysine, L-Ornithine, D-Ornithine, L-Diaminobutyric
      acid, D-Diaminobutyric acid, L-Diaminopimelic acid, [cont.]
<220> FEATURE:
<221> NAME/KEY: MISC_FEATURE
<222> LOCATION: (7)..(7)
<223> OTHER INFORMATION: [cont.] or D-Diaminopimelic acid, and wherein
      from 0 to 10 amino acid residues selected independently at each
      occurrence from Gly, L-Ala, D-Ala, L-Lys, D-Lys, L-Orn, D-Orn,
      L-Glu, D-Glu, [cont.]
<220> FEATURE:
<221> NAME/KEY: MISC_FEATURE
<222> LOCATION: (7)..(7)
<223> OTHER INFORMATION: [cont] L-Asp, and D-Asp is attached to the R
      group of the amino acid; or attached to the R group of the amino
      acid is from 1 to 3 moieties selected independently at each
      [cont.]
<220> FEATURE:
<221> NAME/KEY: MISC_FEATURE
<222> LOCATION: (7)..(7)
<223> OTHER INFORMATION: [cont.] occurrence from a moiety derived from a
      non-alpha primary amino group-containing a C3-12 fatty acid

<400> SEQUENCE: 2

Xaa Phe Gln Asn Cys Pro Xaa Gly
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as Cys with
      from 0 to 10 amino acid residues selected independently at each
      occurrence from Gly, L-Ala, D-Ala, L-Lys, D-Lys, L-Orn, D-Orn,
      L-Glu, D-Glu, L-Asp, and D-Asp attached to R group

<400> SEQUENCE: 3

Xaa Tyr Phe Gln Asn Cys Pro Lys Gly
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
```

```
<220> FEATURE:
<221> NAME/KEY: MISC_FEATURE
<222> LOCATION: (7)..(7)
<223> OTHER INFORMATION: Wherein X at position 7 is defined as Lys with
      from 0 to 5 amino acid residues selected independently at each
      occurrence from Gly, L-Ala, D-Ala, L-Lys, D-Lys, L-Orn, D-Orn,
      L-Glu, D-Glu, L-Asp and D-Asp attached to R group

<400> SEQUENCE: 4

Xaa Phe Gln Asn Cys Pro Xaa Gly
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      0, 3, 6, or 9 Gly residues attached to R group

<400> SEQUENCE: 5

Xaa Phe Xaa Asn Cys Pro Xaa Gly
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (7)..(7)
<223> OTHER INFORMATION: Wherein X at position 7 is defined as Lys with
      6 or 9 Gly residues attached to R group

<400> SEQUENCE: 6

Xaa Phe Gln Asn Cys Pro Xaa Gly
1               5

<210> SEQ ID NO 7
<211> LENGTH: 10
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as 0 to 10
      amino acid residues selected independently at each occurrence from
      Gly, L-Ala, D-Ala, L-Lys, D-Lys, L-Orn, D-Orn, L-Glu, D-Glu,
      L-Asp, and D-Asp
```

```
<400> SEQUENCE: 7

Xaa Cys Tyr Phe Gln Asn Cys Pro Lys Gly
1               5                   10

<210> SEQ ID NO 8
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      Gly attached to R group

<400> SEQUENCE: 8

Xaa Phe Xaa Asn Cys Pro Xaa Gly
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      2 Gly residues attached to R group

<400> SEQUENCE: 9

Xaa Phe Xaa Asn Cys Pro Xaa Gly
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
```

```
<221> NAME/KEY: MISC_FEATURE
<222> LOCATION: (7)..(7)
<223> OTHER INFORMATION: Wherein X at position 7 is defined as Lys with
      3 Gly residues attached to R group

<400> SEQUENCE: 10

Xaa Phe Xaa Asn Cys Pro Xaa Gly
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      4 Gly residues attached to R group

<400> SEQUENCE: 11

Xaa Phe Xaa Asn Cys Pro Xaa Gly
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      5 Gly residues attached to R group

<400> SEQUENCE: 12

Xaa Phe Xaa Asn Cys Pro Xaa Gly
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
```

```
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      6 Gly residues attached to R group

<400> SEQUENCE: 13

Xaa Phe Xaa Asn Cys Pro Xaa Gly
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      7 Gly residues attached to R group

<400> SEQUENCE: 14

Xaa Phe Xaa Asn Cys Pro Xaa Gly
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      8 Gly residues attached to R group

<400> SEQUENCE: 15

Xaa Phe Xaa Asn Cys Pro Xaa Gly
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      9 Gly residues attached to R group

<400> SEQUENCE: 16

Xaa Phe Xaa Asn Cys Pro Xaa Gly
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as
      diaminopimelic acid

<400> SEQUENCE: 17

Xaa Phe Xaa Asn Cys Pro Xaa Gly
1               5

<210> SEQ ID NO 18
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine

<400> SEQUENCE: 18

Xaa Phe Xaa Asn Cys Pro Lys Gly
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      12 aminododecanoic acid attached to R group

<400> SEQUENCE: 19

Xaa Phe Xaa Asn Cys Pro Xaa Gly
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (7)..(7)
<223> OTHER INFORMATION: Wherein X at position 7 is defined as Lys with
      6 Gly residues attached to R group

<400> SEQUENCE: 20

Xaa Phe Gln Asn Cys Pro Xaa Gly
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (7)..(7)
<223> OTHER INFORMATION: Wherein X at position 7 is defined as Lys with
      7 Gly residues attached to R group

<400> SEQUENCE: 21

Xaa Phe Gln Asn Cys Pro Xaa Gly
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
```

```
<221> NAME/KEY: MISC_FEATURE
<222> LOCATION: (7)..(7)
<223> OTHER INFORMATION: Wherein X at position 7 is defined as Lys with
      8 Gly residues attached to R group

<400> SEQUENCE: 22

Xaa Phe Gln Asn Cys Pro Xaa Gly
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (7)..(7)
<223> OTHER INFORMATION: Wherein X at position 7 is defined as Lys with
      9 Gly residues attached to R group

<400> SEQUENCE: 23

Xaa Phe Gln Asn Cys Pro Xaa Gly
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      0 to 10 amino acid residues selected independently at each
      occurrence from Gly, L-Ala, D-Ala, L-Lys, D-Lys, L-Orn, D-Orn,
      L-Glu, D-Glu, L-Asp, and D-Asp attached to R group

<400> SEQUENCE: 24

Xaa Phe Xaa Asn Cys Pro Xaa Gly
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
``` homoglutamine

<400> SEQUENCE: 25

Xaa Phe Xaa Asn Cys Pro Lys Gly
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      9 Gly residues attached to R group and the distal Gly residue is
      acetylated

<400> SEQUENCE: 26

Xaa Phe Xaa Asn Cys Pro Xaa Gly
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      lauric acid attached to R group

<400> SEQUENCE: 27

Xaa Phe Xaa Asn Cys Pro Xaa Gly
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)

```
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      acetyl moiety attached to R group

<400> SEQUENCE: 28

Xaa Phe Xaa Asn Cys Pro Xaa Gly
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Lys with
      diaminopimelic acid attached to R group

<400> SEQUENCE: 29

Xaa Phe Xaa Asn Cys Pro Xaa Gly
1               5

<210> SEQ ID NO 30
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
      mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
      homoglutamine
<220> FEATURE:
<221> NAME/KEY: MISC_FEATURE
<222> LOCATION: (7)..(7)
<223> OTHER INFORMATION: Wherein X at position 7 is defined as Orn

<400> SEQUENCE: 30

Xaa Phe Xaa Asn Cys Pro Xaa Gly
1               5

<210> SEQ ID NO 31
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
``` mercaptopropionic acid derivatized to a Tyr residue
<220> FEATURE:
<221> NAME/KEY: MISC_FEATURE
<222> LOCATION: (3)..(3)
<223> OTHER INFORMATION: Wherein X at position 3 is defined as
    homoglutamine
<220> FEATURE:
<221> NAME/KEY: MISC_FEATURE
<222> LOCATION: (7)..(7)
<223> OTHER INFORMATION: Wherein X at position 7 is defined as
    diaminopimelic acid

<400> SEQUENCE: 31

Xaa Phe Xaa Asn Cys Pro Xaa Gly
1               5

<210> SEQ ID NO 32
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
    mercaptopropionic acid derivatized to a Tyr residue

<400> SEQUENCE: 32

Xaa Phe Gln Asn Cys Pro Lys Gly
1               5

<210> SEQ ID NO 33
<211> LENGTH: 8
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as
    mercaptopropionic acid derivatized to a Tyr residue
<220> FEATURE:
<221> NAME/KEY: MISC_FEATURE
<222> LOCATION: (7)..(7)
<223> OTHER INFORMATION: Wherein X at position 7 is defined as Lys with
    5 Gly residues attached to R group

<400> SEQUENCE: 33

Xaa Phe Gln Asn Cys Pro Xaa Gly
1               5

<210> SEQ ID NO 34
<211> LENGTH: 6
<212> TYPE: PRT
<213> ORGANISM: Artificial sequence
<220> FEATURE:
<223> OTHER INFORMATION: Synthetic

<400> SEQUENCE: 34

Cys Arg Ala Val Lys Tyr
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic

```
<400> SEQUENCE: 35

Asp Asp Ala Val Pro
1               5
```

The embodiments of the invention in which an exclusive property or privilege is claimed are as follows:

1. A peptide comprising Formula (A):

(A)
[Mpa-Tyr-Phe-Z-Asn-Cys-Pro-B(X)$_a$-Gly-NH$_2$], or a pharmaceutically effective salt thereof,
wherein:
the Mpa and Cys residues are covalently connected with a disulfide bond;
Z is Hgn;
B is L-Lys, D-Lys, L-Dap, D-Dap, L-Orn, D-Orn, L-Dab, or D-Dab;
X is independently selected at each occurrence from Gly, L-Ala, D-Ala, L-Lys, D-Lys, L-Orn, D-Orn, L-Glu, D-Glu, L-Asp, and D-Asp; and
a is an integer from 0 to 9.

2. The peptide of claim 1, wherein B is L-Lys.

3. The peptide of claim 1, wherein B is L-Lys and X is Gly.

4. The peptide of claim 1, wherein B is L-Lys, X is Gly, and a is 6, 7, 8, or 9.

5. The peptide of claim 1, wherein B is D-Lys, L-Orn, D-Orn, L-Dab, D-Dab, L-Dap, or D-Dap.

6. The peptide of claim 1, wherein the peptide has a therapeutic index of at least 20.

7. A composition comprising a peptide of claim 1 and a pharmaceutically acceptable excipient.

8. The composition of claim 7, wherein the pharmaceutically acceptable excipient comprises a buffer having a buffering pH of from 3.5 to 6.5.

9. The composition of claim 8, wherein the buffer is selected from an acetate buffer, a citrate buffer, a succinate buffer, a histidine buffer, or any combination thereof.

10. A method of treating a subject in need thereof, comprising:
administering to the subject a therapeutically effective dose of a peptide of claim 1,
wherein the subject has a condition selected from liver fibrosis, cirrhosis, portal hypertension, ascites, esophageal varices, fundal varices, bleeding, arterial hypotension, hepatorenal syndrome, or any combination thereof.

11. The method of claim 10, wherein B is L-Lys.

12. The method of claim 10, wherein B is L-Lys and X is Gly.

13. The method of claim 12, wherein a is 6.

14. The method of claim 10, wherein the subject has cirrhosis and portal hypertension.

15. The method of claim 10, wherein the subject has portal hypertension with a hepatic venous pressure gradient of 5 mm Hg and greater or has clinically significant portal hypertension with a hepatic venous pressure gradient of 10 mm Hg or greater.

16. The method of claim 10, wherein the subject has ascites or refractory ascites.

17. The method of claim 10, wherein the subject has varices or variceal bleeding.

18. The method of claim 10, wherein the subject has a mean arterial pressure of below 95 mm Hg.

19. The method of claim 10, wherein administration comprises parenteral administration, intravenous administration, subcutaneous administration, slow infusion, or bolus administration.

20. The method of claim 10, wherein the peptide is administered at a frequency of three times or less per day.

21. The method of claim 20, wherein the peptide is administered only during daylight hours from 6:00 to 18:00 at a frequency of once every 4 to 6 hours, and wherein administration does not occur at night from 18:00 to 6:00.

22. The method of claim 10, further comprising administering a V2 antagonist.

23. The method of claim 22, wherein the V2 antagonist is administered within 1 to 8 hours before or after administration of the V1a partial agonist.

24. A peptide comprising SEQ ID NO: 13.

25. A peptide comprising SEQ ID NO: 25.

* * * * *